(12) United States Patent
Kobayashi et al.

(10) Patent No.: US 11,364,297 B2
(45) Date of Patent: *Jun. 21, 2022

(54) PHOTOSENSITIZING ANTIBODY-FLUOROPHORE CONJUGATES

(71) Applicant: The United States of America, as represented by the Secretary, Department of Health and Human Services, Bethesda, MD (US)

(72) Inventors: Hisataka Kobayashi, Laurel, MD (US); Peter Choyke, Rockville, MD (US)

(73) Assignee: THE UNITED STATES OF AMERICA, as represented by the Secretary, Department of Health and Human Services, Bethesda, MD (US)

( * ) Notice: Subject to any disclaimer, the term of this patent is extended or adjusted under 35 U.S.C. 154(b) by 122 days.

This patent is subject to a terminal disclaimer.

(21) Appl. No.: 16/694,761

(22) Filed: Nov. 25, 2019

(65) Prior Publication Data

US 2020/0085950 A1 Mar. 19, 2020

Related U.S. Application Data

(60) Continuation of application No. 14/868,040, filed on Sep. 28, 2015, now Pat. No. 10,537,641, which is a division of application No. 14/126,060, filed as application No. PCT/US2012/044421 on Jun. 27, 2012, now Pat. No. 9,358,306, which is a continuation-in-part of application No. 13/180,111, filed on Jul. 11, 2011, now Pat. No. 8,524,239.

(60) Provisional application No. 61/363,079, filed on Jul. 9, 2010.

(51) Int. Cl.
| | | |
|---|---|---|
| *A61K 31/704* | (2006.01) |
| *A61K 39/395* | (2006.01) |
| *A61K 41/00* | (2020.01) |
| *A61K 49/16* | (2006.01) |
| *A61K 47/68* | (2017.01) |
| *C07K 16/28* | (2006.01) |
| *C07K 16/30* | (2006.01) |
| *C07K 16/32* | (2006.01) |
| *A61K 45/06* | (2006.01) |
| *G01N 33/50* | (2006.01) |
| *A61K 49/00* | (2006.01) |
| *A44C 15/00* | (2006.01) |
| *A41D 13/00* | (2006.01) |
| *A61K 39/00* | (2006.01) |

(52) U.S. Cl.
CPC .......... *A61K 45/06* (2013.01); *A61K 31/704* (2013.01); *A61K 41/0071* (2013.01); *A61K 47/6803* (2017.08); *A61K 47/6869* (2017.08); *A61K 49/0032* (2013.01); *A61K 49/0058* (2013.01); *C07K 16/2863* (2013.01); *C07K 16/30* (2013.01); *C07K 16/3069* (2013.01); *C07K 16/32* (2013.01); *G01N 33/5011* (2013.01); *A41D 13/0002* (2013.01); *A41D 2400/32* (2013.01); *A44C 15/00* (2013.01); *A61K 2039/505* (2013.01); *C07K 2317/24* (2013.01); *C07K 2317/73* (2013.01); *C07K 2317/77* (2013.01)

(58) Field of Classification Search
CPC .......... A61K 49/0058; A61K 2039/505; A61K 41/0071; A61K 47/6803; A61K 49/0036; C07K 16/2863; C07K 16/32; A61N 5/062
See application file for complete search history.

(56) References Cited

U.S. PATENT DOCUMENTS

| | | |
|---|---|---|
| 2,915,392 A | 12/1959 | Pedersen |
| 5,196,005 A | 3/1993 | Doiron et al. |
| 5,494,793 A | 2/1996 | Schindele et al. |
| 6,344,050 B1 | 2/2002 | Chen |

(Continued)

FOREIGN PATENT DOCUMENTS

| | | |
|---|---|---|
| CN | 102585003 | 7/2012 |
| CN | 103781495 A | 5/2014 |

(Continued)

OTHER PUBLICATIONS

Sasikumar et al., Small-Molecule Immune Checkpoint Inhibitors Targeting PD-1/PD-L1 and Other Emerging Checkpoint PathwaysBioDrugs, 2018: 32:481-497.*

(Continued)

*Primary Examiner* — Hong Sang
(74) *Attorney, Agent, or Firm* — Klarquist Sparkman, LLP

(57) ABSTRACT

The present disclosure relates to compositions and methods of killing cells. In particular examples, the method includes contacting a cell having a cell surface protein with a therapeutically effective amount of an antibody-IR700 molecule, wherein the antibody specifically binds to the cell surface protein, such as a tumor-specific antigen on the surface of a tumor cell. The cell is subsequently irradiated, such as at a wavelength of 660 to 740 nm at a dose of at least 1 J cm$^{-2}$. The cell is also contacted with one or more therapeutic agents (such as an anti-cancer agent), for example about 0 to 8 hours after irradiating the cell, thereby killing the cell. Also provided are methods of imaging cell killing in real time, using fluorescence lifetime imaging. Also provided are wearable devices that include an article of clothing, jewelry, or covering; and an NIR LED incorporated into the article, which can be used with the disclosed methods.

12 Claims, 24 Drawing Sheets

(19 of 24 Drawing Sheet(s) Filed in Color)

(56) References Cited

U.S. PATENT DOCUMENTS

| | | | |
|---|---|---|---|
| 6,534,041 B1 | 3/2003 | Licha et al. | |
| 7,005,518 B2 | 2/2006 | Peng et al. | |
| 7,498,029 B2 | 3/2009 | Hasan et al. | |
| 8,524,239 B2* | 9/2013 | Kobayashi | A61N 5/062 424/178.1 |
| 8,623,354 B2 | 1/2014 | Brown et al. | |
| 9,358,306 B2 | 6/2016 | Kobayashi et al. | |
| 9,538,306 B2* | 1/2017 | Nakamura | H04S 1/00 |
| 10,537,641 B2* | 1/2020 | Kobayashi | A61K 47/6803 |
| 10,538,590 B2* | 1/2020 | Kobayashi | A61K 49/0032 |
| 11,013,803 B2 | 5/2021 | Kobayashi et al. | |
| 2001/0044124 A1 | 11/2001 | Bacus | |
| 2004/0120949 A1 | 6/2004 | Adolf et al. | |
| 2005/0147612 A1 | 7/2005 | Yayon | |
| 2005/0157292 A1 | 7/2005 | Saitoh et al. | |
| 2006/0188509 A1* | 8/2006 | Derynck | A61P 13/08 424/155.1 |
| 2006/0231107 A1 | 10/2006 | Glickman et al. | |
| 2007/0020272 A1 | 1/2007 | Hasan | |
| 2007/0133086 A1 | 6/2007 | Wilhelm et al. | |
| 2008/0073566 A1 | 3/2008 | Frangioni | |
| 2008/0095699 A1 | 4/2008 | Zheng et al. | |
| 2008/0095950 A1 | 4/2008 | Hall-Goulle et al. | |
| 2008/0253960 A1 | 10/2008 | Zheng et al. | |
| 2010/0215575 A1 | 8/2010 | O'Neill et al. | |
| 2010/0255057 A1 | 10/2010 | Hyde et al. | |
| 2011/0082412 A1 | 4/2011 | Hyde et al. | |
| 2011/0288234 A1 | 11/2011 | Pandey et al. | |
| 2012/0010558 A1 | 1/2012 | Kobayashi et al. | |
| 2012/0070377 A1 | 3/2012 | Yahioglu et al. | |
| 2012/0070853 A1 | 3/2012 | Johansen et al. | |
| 2012/0122094 A1 | 5/2012 | May et al. | |
| 2013/0287688 A1 | 10/2013 | Jain et al. | |
| 2013/0336995 A1 | 12/2013 | Kobayashi et al. | |
| 2014/0120119 A1 | 5/2014 | Kobayashi et al. | |
| 2014/0309578 A1 | 10/2014 | Anvari | |
| 2015/0140022 A1 | 5/2015 | Barth et al. | |
| 2015/0343060 A1 | 12/2015 | Kovar et al. | |
| 2015/0343084 A1 | 12/2015 | Dilley | |
| 2015/0374819 A1 | 12/2015 | Kovar | |
| 2016/0228568 A1 | 8/2016 | de los Pinos et al. | |
| 2016/0256564 A2 | 9/2016 | Kobayashi et al. | |
| 2017/0122853 A1 | 5/2017 | Kobayashi et al. | |
| 2018/0113246 A1 | 4/2018 | Rose et al. | |
| 2018/0113247 A1 | 4/2018 | Rose et al. | |
| 2018/0236076 A1 | 8/2018 | Kobayashi et al. | |
| 2018/0239074 A1 | 8/2018 | Rose et al. | |
| 2018/0250405 A1 | 9/2018 | Biel et al. | |
| 2019/0015510 A1 | 1/2019 | Makings et al. | |
| 2020/0095331 A1 | 3/2020 | Kobayashi et al. | |
| 2021/0010914 A1 | 1/2021 | Kobayashi et al. | |
| 2021/0079112 A1 | 3/2021 | Kobayashi et al. | |

FOREIGN PATENT DOCUMENTS

| | | |
|---|---|---|
| CN | 104203286 A | 12/2014 |
| DE | 197 17 904 A1 | 10/1998 |
| EP | 1512963 A1 | 3/2005 |
| EP | 2731626 B1 | 12/2018 |
| JP | 2003-284757 A | 10/2003 |
| JP | 2003-344284 A | 12/2003 |
| JP | 2006-515892 A | 6/2006 |
| JP | 2006-517230 A | 7/2006 |
| JP | 2007-155752 A | 6/2007 |
| JP | 2014-523907 A | 9/2014 |
| WO | WO 2000/062807 A1 | 10/2000 |
| WO | WO 2001057495 | 8/2001 |
| WO | WO 2003/011106 A2 | 2/2003 |
| WO | WO 2003/032900 A2 | 4/2003 |
| WO | WO 2003/083811 A1 | 10/2003 |
| WO | WO 2004/038378 A2 | 5/2004 |
| WO | WO 2004/067038 A1 | 8/2004 |
| WO | WO 2004/071571 A1 | 8/2004 |
| WO | WO 2005099689 | 10/2005 |
| WO | WO 2006/092598 A2 | 9/2006 |
| WO | WO 2007/070680 A2 | 6/2007 |
| WO | WO 2008/005942 A2 | 1/2008 |
| WO | WO 2008/120134 A1 | 10/2008 |
| WO | WO 2008152424 | 12/2008 |
| WO | WO 2009038776 | 3/2009 |
| WO | WO 2009/079024 A1 | 6/2009 |
| WO | WO 2009092062 | 7/2009 |
| WO | WO 2009/107139 A1 | 9/2009 |
| WO | WO 2010/047611 A1 | 4/2010 |
| WO | WO 2010/085651 A1 | 7/2010 |
| WO | WO 2010121163 | 10/2010 |
| WO | WO 2011/014726 A1 | 2/2011 |
| WO | WO 201103 8006 | 3/2011 |
| WO | WO 2011025950 | 3/2011 |
| WO | WO 2011/123742 A1 | 10/2011 |
| WO | WO 2012076631 | 6/2012 |
| WO | WO 2012082118 | 6/2012 |
| WO | WO 2013/009475 A1 | 1/2013 |
| WO | WO 2013044156 | 3/2013 |
| WO | WO 2014/084394 A1 | 6/2014 |
| WO | WO 2014089247 | 6/2014 |
| WO | WO 2014127365 | 8/2014 |
| WO | WO 2014168950 | 10/2014 |
| WO | WO 2015057692 | 4/2015 |
| WO | WO 2015187651 | 12/2015 |
| WO | WO 2015187677 | 12/2015 |
| WO | WO 2016/022896 A1 | 2/2016 |
| WO | WO 2017027247 A1 | 2/2017 |
| WO | WO 2017031363 | 2/2017 |
| WO | WO 2017031367 A1 | 2/2017 |
| WO | WO 2018080952 | 5/2018 |
| WO | WO 2018156815 | 8/2018 |
| WO | WO 2019009941 | 1/2019 |

OTHER PUBLICATIONS

Wooldridge et al.., "Immunostimulatory Oligodeoxynucleotides Containing CpG Motifs Enhance the Efficacy of Monoclonal Antibody Therapy of Lymphoma," *Blood* 89:2994-2998, 1997.

Ishii et al., "Defucosylated Humanized Anti-CCR4 Monoclonal Antibody KW-0761 as a Novel Immunotherapeutic Agent for Adult T-cell Leukemia/Lymphoma," *Clin Cancer Res.* 16:1520-1531, 2010.

Ito et al., "Combination photoimmunotherapy with monoclonal antibodies recognizing different epitopes of human epidermal growth factor receptor 2: an assessment of phototherapeutic effect based on fluorescence molecular imaging," *Oncotarget* 7:14143-14152, 2016.

Rosas-Arellano et al., "A simple solution for antibody signal enhancement in immunofluorescence and triple immunogold assays," *Histochem Cell Biol.* 146:421-430, 2016.

Clinical Trial Identifier NCT02422979, first posted on Apr. 22, 2015. Last updated on Sep. 20, 2019.

Doane et al., "Observation and Photophysical Characterization of Silicon Phthalocyanine J-Aggregate Dimers in Aqueous Solutions," *Chem Eur J.* 20:8030-8039, 2014.

Maawy et al., "Photoimmunotherapy lowers recurrence after pancreatic cancer surgery in orthotopic nude mouse models," *J Surg Res.* 197:5-11, 2015.

Nagaya et al., "Near infrared photoimmunotherapy of B-cell lymphoma," *Mol Oncol.* 10:1404-1414, 2016.

Sanchez-Barcelo et al., "Recent Patents on Light Based Therapies: Photodynamic Therapy, Photothermal Therapy and Photoimmunotherapy," *Recent Patents on Endocrine, Metabolic & Immune Drug Discovery* 8:1-8, 2014.

Serebrovskaia et al., "Genetically Encoded Photoimmunosensitizer," *Bioorg. Khim.* 37:137-144, 2011 (English Abstract Only).

Supplementary materials from Sugiyama et al., "Anti-CCR4 mAb selectively depletes effector-type FoxP3+CD4+ regulatory T cells, evoking antitumor immune responses in humans," *Proc Natl Acad Sci. USA* 110:17945-17950, 2013. (5 pages).

Yoon et al., "Advance in Photosensitizers and Light Delivery for Photodynamic Therapy," *Clin Endosc.* 46:7-23, 2013.

Zhang et al., "Target-selective phototherapy using a ligand-based photosensitizer for type 2 cannabinoid receptor," *Chem Biol.* 21:338-344, 2014 (with 7 pages of Supplementary Materials).

(56) References Cited

OTHER PUBLICATIONS

Zhang et al., "Tumor mitochondria-targeted photodynamic therapy with a translocator protein (TSPO)-specific photosensitizer," *Acta Biomater.* 28:160-170, 2015 (with 6 pages of Supplementary Materials).
Zinn et al., "IND-Directed Safety and Biodistribution Study of Intravenously Injected Cetuximab-IRDye800 in Cynomolgus Macaques." *Mol Imaging Biol.* 17:49-57, 2015.
Ali et al., "Dynamic fluorescent imaging with indocyanine green for monitoring the therapeutic effects of photoimmunotherapy," *Contrast Media Mol Imaging* 9(4):276-282, 2014.
Amoury et al., "Photoimmunotheranostic agents for triple-negative breast cancer diagnosis and therapy that can be activated on demand," *Oncotarget* 7(34):54925-54936, 2016.
Anonymous, "Anodyne: Tratamento com tecnologia MIRE," Forumenfermagem-Projecto Feridas, Jan. 24, 2011, XP002686605, retrieved from the internet: URL:http://forumenfermagem.org/feridas/?s=anodyne, retrieved on Nov. 7, 2012.
Anonymous, "Near Infrared Light for the Treatment of Painful Peripheral Neuropathy," U.S. National Institutes of Health, Aug. 2, 2012, XP002686617, retrieved from the internet: URL:http://www.clinicaltrials.gov/ct2/show/NCT00125268, retrieved on Nov. 7, 2011.
Anonymous, "Near IR Signature Management for Combat Clothing and Equipment," Australian Government Department of Defence, DSTO, Apr. 7, 2005, XP002686606, retrieved from the internet: URL:http://www.dsto.defence.gov.au/reserach/3214/?print=true, retrieved on Nov. 6, 2012.
Ballou et al., "Tumor Labeling in Vivo Using Cyanine-Conjugated Monoclonal Antibodies," *Cancer Immunol. Immunother.* 41:257-263, 1995.
Baolin et al., Practical Pathophysiology, Qing Dao Ocean University Press, Dec. 1995. (see English translation of CN201280043973.2 Notification of Reexamination (pp. 5-6) for relevance).
Barrett et al., "In vivo Diagnosis of Epidermal Growth Factor Receptor Expression using Molecular Imaging with a Cocktail of Optically Labeled Monoclonal Antibodies," *Clin Cancer Res.* 13:6639-6648, 2007.
Carcenac et al., "Internalisation enhances photo-induced cytotoxicity of monoclonal antibody-phthalocyanine conjugates." *Br J. Cancer* 85:1787-1793, 2001.
Carter et al., "Identification and Validation of Cell Surface Antigens for Antibody Targeting in Oncology," *Endocr Relat Cancer* 11:659-687, 2004.
Chen et al., "Tumor vascular permeabilization by vascular-targeting photosensitization: effects, mechanism, and therapeutic implications," *Clin Cancer Res.* 12:917-923, 2006.
Chiarello, K., "In between the light and the dark: developments in Photosensitive Pharmaceuticals," *Pharmaceutical Technology*, pp. 48-54, Dec. 2004.
Chopra, "IRDye 700DX-Labeled annexin V," Molecular Imaging and Contrast Agent Database (MICAD) [Internet]. Bethesda (MD): National Center for Biotechnology Information (US); 2004-2013. Oct. 27, 2009 [updated Dec. 17, 2009].
Davis et al., "Nanoparticle Therapeutics: An Emerging Treatment Modality for Cancer," *Nat Rev Drug Dis.* 7:771-782, 2008.
De Boer et al., "A standardized light-emitting diode device for photoimmunotherapy," *J Nucl Med.* 55(11):1893-1898, 2014.
De Boer et al., "Biodistribution Study of Intravenously Injected Cetuximab-IRDye700DX in Cynomolgus Macaques," *Mol Imaging Biol.* 18(2):232-242, 2016.
Del Governatore et al., "Experimental Photoimmunotherapy of Hepatic Metastases of Colorectal Cancer with a 17.1 A chlorine$_{e6}$ Immunoconjugate," *Cancer Res.* 60:4200-4205, 2000.
Denis et al., "Synthesis, bioanalysis and biodistribution of photosensitizer conjugates for photodynamic therapy," *Bioanalysis* 5:1099-1114, 2013.
Dixit et al., "Transferrin Receptor-Targeted Theranostic Gold Nanoparticles for Photosensitizer Delivery in Brain Tumors," *Nanoscale*, 7(5):1782-1790, 2015.

Duska et al., Combination Photoimmunotherapy and Cisplatin: Effects on Human Ovarian Cancer Ex Vivo, *J Nat Cancer Inst.* 97:1557-1563, 1999.
Gajewski et al., "The P815 Mastocytoma Tumor Model," *Curr Protoc Immunol.* 43:20.4.1-20.4.18, 2001.
Gao et al., "In vivo Cancer Targeting and Imaging With Semiconductor Quantum Dots," *Nat Biotechnol.* 22:969-976 and 5 pages of supplemental notes, 2004.
Gleysteen et al." Fluorescently labeled cetuximab to evaluate head and neck cancer response to treatment," *Cancer Biol Ther.* 6:e1-e5, 2007.
Greish, Khaled, "Enhanced permeability and retention of macromolecular drugs in solid tumors: a royal gate for targeted anticancer nanomedicines," *J Drug Target.* 15:457-464, 2007.
Hanaoka et al., "Glypican-3 targeted human heavy chain antibody as a drug carrier for hepatocellular carcinoma therapy," *Mol Pharm.* 12(6):2151-2157, 2015.
Hanaoka et al., "Photoimmunotherapy of hepatocellular carcinoma-targeting Glypican-3 combined with nanosized albumin-bound paclitaxel," *Nanomedicine (Lond).* 10(7):1139-1147, 2015.
Heukers et al., "Nanobody-photosensitizer conjugates for targeted photodynamic therapy," *Nanomedicine* 10:1441-1451, 2014.
Hiroshima et al., "Photoimmunotherapy Inhibits Tumor Recurrence After Surgical Resection on a Pancreatic Cancer Patient-Derived Orthotopic Xenograft (PDOX) Nude Mouse Model," *Ann Surg Oncol.* 22 Suppl 3:S1469-S1474, 2015.
Iqbal et al., "Phthalocyanine-Biomolecule Conjugated Photosensitizers for Targeted Photodynamic Therapy and Imaging," *Curr Drug Metab.* 16(9):816-832, 2015.
Ishida et al., "Trastuzumab-Based Photoimmunotherapy Integrated with Viral HER2 Transduction Inhibits Peritoneally Disseminated HER2-Negative Cancer," *Mol Cancer Ther.* 15(3):402-411, 2016.
Ito et al., "Molecular targeted photoimmunotherapy for HER2-positive human gastric cancer in combination with chemotherapy results in improved treatment outcomes through different cytotoxic mechanisms," *BMC Cancer* 16:37, 2016.
Jia et al., "Cannabinoid CB2 receptor as a new phototherapy target for the inhibition of tumor growth," *Mol Pharm.* 11(6):1919-1929, 2014.
Jing et al., "Imaging and Selective Elimination of Glioblastoma Stem Cells with Theranostic Near-Infrared-Labeled CD133-Specific Antibodies," *Theranostics* 6(6):862-874, 2016.
Kijanka et al., "Optical imaging of pre-invasive breast cancer with a combination of VHHs targeting CAIX and HER2 increases contrast and facilitates tumour characterization," *EJNMMI Res.* 6(1):14, 2016.
Kines et al., "HPV Based Photodynamic Therapy: A New Approach for Anti-Cancer Therapy," *J. Immunol.* 192(1): Supplement 206.8, 2014.
Kirveliene et al., "Schedule-Dependent Interaction Between Doxorubicin And mTHPC-Mediated Photodynamic Therapy In Murine Hepatoma In Vitro And In Vivo," *Cancer Chemother. Pharmacol.* 57:65-72, 2005.
Kishimoto et al., "Evaluation of oxygen dependence on in vitro and in vivo cytotoxicity of photoimmunotherapy using IR-700-antibody conjugates," *Free Radic Biol Med.* 85:24-32, 2015.
Kobayashi, "Near infrared photoimmunotherapy: A new cancer therapy kills cancer cells with exposure of harmless near infrared light," Poster Presentation, at NEST Conference, Tokyo, Japan, Apr. 2018.
Kobayashi, "Activatable Fluorescent Imaging Probes for Cancer Detection and Diagnosis," Abstract presented at the American Chemical Society meeting in San Francisco, 2014.
Kovar et al., "A Systematic Approach to the Development of Fluorescent Contrast Agents for Optical Imagining of Mouse Cancer Models," *Anal. Biochem.* 367:1-12, 2007.
Licor, "High Photostability of IRDye® 700DX," Retrieved on Aug. 23, 2018. Retrieve on https://www.licor.com/bio/products/reagents/irdye/700dx/photostability.html.
Li-Cor, "IRDye® Infrared Dyes: Advancing Discovery with Infrared Imaging," 2010.
Maawy et al., "Near infra-red photoimmunotherapy with anti-CEA-IR700 results in extensive tumor lysis and a significant decrease in

(56) References Cited

OTHER PUBLICATIONS tumor burden in orthotopic mouse models of pancreatic cancer," *PLoS One* 10(3):e0121989, 2015.

Maya et al., "Synthesis, Aggregation Behavior and Nonlinear Absorption Properties of Lead Phthalocyanines Substituted with Siloxane Chains," *J Materials Chem.* 13:1603-1613, 2003.

McHugh et al., "The role of suppressor T cells in regulation of immune responses," J Allergy Clin Immunol. 110:693-702, 2002.

Mitchell et al., "Comparison of Two Infrared Devices in Their Effectiveness in Reducing Symptoms Associated with RLS," Physiother. Theory Prac., 2011, XP002686651, retrieved from the internet: URL:http://www.ncbi.nlm.nih.gov.pubmed/20950168, retrieved on Nov. 8, 2012.

Mitchell et al., "Comparison of Two Infrared Devices in Their Effectiveness in Reducing Symptoms Associated with RLS," *Physiother. Theory Pract.* 27:352-359, 2011.

Mitsunaga et al., "Abstract 3618: Target-Specific Photo-Activatable Immunotherapy (PIT) for Cancer Based on a Monoclonal Antibody-Photosensitizer Conjugate," in *Proceedings of the 102nd Annual Meeting of the American Association for Cancer Research*; Apr. 2-6, 2011; Orlando, FL. Philadelphia (PA): AACR; Cancer Res. 71:3618,2011.

Mitsunaga et al., "Immediate in vivo target-specific cancer cell death after near infrared photoimmunotherapy," *BMC Cancer.* 12:345, 2012.

Mitsunaga et al., "Cancer Cell-Selective in Vivo Near Infrared Photomimmunotherapy Targeting Specific Membrane Molecules," *Nat. Med.* 17:1685-1691, 2011.

Mitsunaga et al., "Near-Infrared Theranostic Photoimmunotherapy (PIT): Repeated Exposure of Light Enhances the Effect of Immunoconjugate," *Bioconjug. Chem.* 23:604-609, 2012.

Moore et al., "Photoimmunotherapy of residual disease after incomplete surgical resection in head and neck cancer models," *Cancer Med.* 5(7): 1526-1534, 2016.

Nagaya et al., "Host Immunity Following Near-Infrared Photoimmunotherapy Is Enhanced with PD-1 Checkpoint Blockade to Eradicate Established Antigenic Tumors," *Cancer Immunol Res.* 7:401-413, 2019.

Nagaya et al., "Improved micro-distribution of antibody-photon absorber conjugates after initial near infrared photoimmunotherapy (NIR-PIT)," *J Control Release* 232:1-8, 2016.

Nagaya et al., "Near infrared photoimmunotherapy targeting bladder cancer with a canine anti-epidermal growth factor receptor (EGFR) antibody," *Oncotarget* 9:19026-19038,2018.

Nagaya et al., "Near Infrared Photoimmunotherapy Targeting EGFR Positive Triple Negative Breast Cancer: Optimizing the Conjugate-Light Regimen," *PLoS One* 10(8):e0136829, 2015.

Nagaya et al., "Near infrared photoimmunotherapy with an anti-mesothelin antibody," *Oncotarget* 7(17):23361-23369, 2016.

Nagaya et al., "Near infrared photoimmunotherapy with avelumab, an anti-programmed death-ligand 1 (PD-L1) antibody," *Oncotorget* 8:8807-8817, 2017.

Nagaya et al., "Syngeneic Mouse Models of Oral Cancer Are Effectively Targeted by Anti-CD44-Based NIR-PIT," *Mol Cancer Res.* 15:1667-1677, 2017.

Nakajima et al., "Improving the Efficacy of Photoimmunotherapy (PIT) Using a Cocktail of Antibody Conjugates in a Multiple Antigen Tumor Model," *Theranostics* 3:357-365, 2013.

Nakajima et al., "Real-time monitoring of in vivo acute necrotic cancer cell death induced by near infrared photoimmunotherapy using fluorescence lifetime imaging," *Cancer Res.* 72(18):4622-4628, 2012.

Nakajima et al., "The effects of conjugate and light dose on photo-immunotherapy induced cytotoxicity," *BMC Cancer* 30;14:389, 2014.

Nakamura et al., "MR imaging biomarkers for evaluating therapeutic effects shortly after near infrared photoimmunotherapy," *Oncotarget* 7(13):17254-17264, 2016.

Nowis et al., "The influence of photodynamic therapy on the immune response," *Photodiagnosis Photodyn Ther.* 2:283-298, 2005.

Ogawa et al., "In vivo Molecular Imaging of Cancer with a Quenching Near-Infrared Fluorescent Probe Using Conjugates of Monoclonal Antibodies and Indocyanine Green," *Cancer Res.* 69:1268-1272, 2009.

Peng et al., "Phthalocyanine Dye As An Extremely Photostable And Highly Fluorescent Near-Infrared Labeling Reagent," *Proceedings of SPIE* 6097:60970E-1-60970E-12, 2006.

Rosenthal et al., "In Vivo Detection of Head and Neck Cancer Orthotopic Xenografts by Immunofluorescence," *Laryngoscope* 116:1636-1641, 2006.

Sano et al., "Acute cytotoxic effects of photoimmunotherapy assessed by 18F-FDG PET," *J Nucl Med.* 54(5):770-775, 2013.

Sano et al., "The effect of photoimmunotherapy (PIT) followed by liposomal daunorubicin in a mixed tumor model: A demonstration of the super-enhanced permeability and retention (SUPR) effect after PIT," *Mol Cancer Ther.* 13(2):426-432, 2014.

Sano et al., "Markedly Enhanced Permeability and Retention Effects Induced by Photo-Immunotherapy of Tumors," ACS Nano. 7:717-724, 2013, including 19 pages of supporting information).

Sato et al., "Photoimmunotherapy: comparative effectiveness of two monoclonal antibodies targeting the epidermal growth factor receptor," *Mol Oncol.* 8(3):620-632, 2014.

Sato et al., "Photoinduced Ligand Release from a Silicon Phthalocyanine Dye Conjugated with Monoclonal Antibodies: A Mechanism of Cancer Cell Cytotoxicity after Near-Infrared Photoimmunotherapy," *ACS Cent Sci.* 4:1559-1569, 2018.

Sato et al., "Spatially selective depletion of tumor-associated regulatory T cells with near-infrared photoimmunotherapy," *Sci Transl Med.* 8:352ra110, 2016.

Sato et al., "Comparative effectiveness of light emitting diodes (LEDs) and Lasers in near infrared photoimmunotherapy," *Oncotarget* 7(12):14324-14335, 2016.

Sato et al., "Near infrared photoimmunotherapy for lung metastases," *Cancer Lett.* 365(1):112-121, 2015.

Sato et al., "Near infrared photoimmunotherapy in the treatment of disseminated peritoneal ovarian cancer," *Mol Cancer Ther.* 14(1):141-150, 2015.

Sato et al., "Near infrared photoimmunotherapy in the treatment of pleural disseminated NSCLC: preclinical experience," *Theranostics* 5(7):698-709, 2015.

Sato et al., "Photoimmunotherapy of gastric cancer peritoneal carcinomatosis in a mouse model," *PLoS One* 9(11):e113276, 2014.

Sato et al., "Selective cell elimination in vitro and in vivo from tissues and tumors using antibodies conjugated with a near infrared phthalocyanine," *RSC Adv.* 5(32):25105-25114, 2015.

Savellano et al., "Multiepitope HER2 Targeting Enhances Photoimmunotherapy of HER2-Overexpressing Cancer Cells with Pyropheophorbide-a Immunoconjugates," *Cancer Res.* 65:6371-6379, 2005.

Scully et al., "Application Of Fluorescence Lifetime Imaging Microscopy To The Investigation Of Intracellular PDT Mechanisms," *Bioimaging* 5:9-18, 1997.

Serebrovskaya et al., "Targeting Cancer Cells by Using an Antireceptor Antibody-Photosensitizer Fusion Protein," *Proc Nat Acad Sci.* 106:9221-9225, 2009.

Shimoyama et al., "Viral transduction of the HER2-extracellular domain expands trastuzumab-based photoimmunotherapy for HER2-negative breast cancer cells," *Breast Cancer Res Treat.* 149(3):597-605, 2015.

Shirasu et al., "Potent and specific antitumor effect of CEA-targeted photoimmunotherapy," *Int J Cancer.* 135(11):2697-710, 2014.

Snyder et al., "Photodynamic therapy: a means to enhanced drug delivery to tumors," *Cancer Res.* 63:8126-8131, 2003.

Soukos et al., "Epidermal Growth Factor Receptor-Targeted Immunophotodiagnosis and Photoimmunotherapy of Oral Precancer in Vivo," *Cancer Res.* 61:4490-4496, 2001.

Steele et al., "Suppressor deletion therapy: selective elimination of T suppressor cells in vivo using a hematoporphyrin conjugated monoclonal antibody permits animals to reject syngeneic tumor cells," *Cancer Immunol Immunother.* 26:125-131, 1988.

(56) References Cited

OTHER PUBLICATIONS

Sugiyama et al., "Anti-CCR4 mAb selectively depletes effector-type FoxP3+CD4+ regulatory T cells, evoking antitumor immune responses in humans," *Proc Natl Acad Sci. USA* 110:17945-17950, 2013.
Supplementary materials from Mitsunaga et al., "Cancer Cell-Selective in Vivo Near Infrared Photoimmunotherapy Targeting Specific Membrane Molecules," *Nat. Med.* 17:1685-1691, 2011.
Van Dongen et al., "Photosensitizer-Antibody Conjugates for Detection and Therapy of Cancer," *Adv Drug Deliv Rev.* 56:31-52, 2004.
Van Driel et al., "EGFR targeted nanobody-photosensitizer conjugates for photodynamic therapy in a pre-clinical model of head and neck cancer," *J Control Release* 229:93-105, 2016.
Von Felbert et al., "A specific photoimmunotheranostics agent to detect and eliminate skin cancer cells expressing EGFR," *J Cancer Res Clin Oncol.* 142(5):1003-1011, 2016.
Vrouenraets et al., "Targeting of Aluminum (III) Phthalocyanine Tetrasulfonate by Use of Internalizing Monoclonal Antibodies: Improved Efficacy in Photodynamic Therapy," *Cancer Res.* 61:1970-1975, 2001.
Waite and Roth, "Nanoscale drug delivery systems for enhanced drug penetration into solid tumors: current progress and opportunities," *Crit Rev Biomed Eng.* 40:21-41, 2012.
Wang et al., "Theranostic Agents for Photodynamic Therapy of Prostate Cancer by Targeting Prostate-Specific Membrane Antigen," *Mol Cancer Ther.* 15(8):1834-1844, 2016.
Watanabe et al., "Photoimmunotherapy Targeting Prostate-Specific Membrane Antigen: Are Antibody Fragments as Effective as Antibodies? ," *J Nucl Med.* 56:140-144, 2015.
Wessels et al., "Advances in cellular, subcellular, and nanoscale imaging in vitro and in vivo," *Cytometry A*:77:667-676, 2010.
Xu et al., "Antibody Conjugated Magnetic Iron Oxide Nanoparticles for Cancer Cell Separation in Fresh Whole Blood," *Biomaterials* 32:9758-9765, 2011.
Zhu et al., "Visualization of $P53_{264-272}$/HLA-A*0201 Complexes Naturally Presented on Tumor Cell Surface by a Multimeric Soluble Single-Chain T Cell Receptor," *J. Immunol.* 176:3223-3232, 2006.
Zuluaga et al., "Combination of Photodynamic Therapy With Anti-Cancer Agents," *Curr. Med. Chem.* 15:1655-1673, 2008.
CN 201280043973.2 First Office Action dated Nov. 24, 2014, with English translation (19 pages).
CN 201280043973.2 Office Action dated Feb. 22, 2016 for Application No. 201280043973.2 (with English translation).
CN 201280043973.2 Reexamination Notification dated Nov. 17, 2016, with English translation.
CN 201280043973.2 Second Office Action dated Aug. 12, 2015, with English translation (15 pages).
EP12738664.7 Examination Report dated Jul. 6, 2016.
JP 2014520202 Final Official Action dated Sep. 28, 2016, with English translation.
JP 2014-520202 Office Action dated Feb. 3, 2016, with English translation.
PCT/US2012/044421 International Search Report and Written Opinion dated Nov. 26, 2012 (18 pages). (Discloses/discusses relevance of "Anonymous, 'Anodyne: Tratamento . . . '").
PCT/US2015/044168 International Search Report and Written Opinion dated Oct. 19, 2016 (11 pages).
PCT/US2016/045090 International Search Report and Written Opinion dated Oct. 11, 2016 (12 pages).
PCT/US2019/026488 International Search Report and Written Opinion dated Jun. 26, 2019 (15 pages).
SG 2013091822 Search Report and Written Opinion dated Mar. 20, 2015 (9 pages).
SG 2013091822 Written Opinion dated Nov. 11, 2015 (10 pages).
Onizuka et al., "Tumor Rejection by in Vivo Administration of Anti-CD25 (Interleukin-2 Receptor α) Monoclonal Antibody," *Cancer Res.* 59:3128-3133, 1999.
Marabelle et al., "Depleting tumor-specific Tregs at a single site eradicates disseminated tumors," *J Clin Invest.* 123:2441-2463, 2013.
Maruoka et al., "Combined CD44- and CD25-targeted Near-Infrared Photoimmunotherapy to Selectively Kill Cancer and Regulatory T cells in Syngeneic Mouse Cancer Models," *Cancer Immunol Res.* 8:345-355, 2020.
Dougherty et al., "Photodynamic Therapy," *J Natl Cancer Inst.* 90:889-905, 1998.
Agostinis et al., "Photodynamic Therapy of Cancer: An Update," *CA Cancer J Clin.* 61(4): 250-281, 2011.
Bartl et al., "Emissivity of aluminium and its importance for radiometric measurement," Measurement of Physical Quantities, 31-36, 2004.
BIO Clinica, vol. 19, p. 398-403, 2004 (in Japanese, with concise description in English).
Busch et al., "Increasing Damage to Tumor Blood Vessels during Motexafin Lutetium-PDT through Use of Low Fluence Rate," *Radiat Res.* 174(3):331-340, 2010.
Chauhan et al., "Angiotensin inhibition enhances drug delivery and potentiates chemotherapy by decompressing tumour blood vessels," *Nat Commun.* 4:2516, 2013 (11 pages).
Dolmans et al., "Targeting Tumor Vasculature and Cancer Cells in Orthotopic Breast Tumor by Fractionated Photosensitizer Dosing Photodynamic Therapy," *Cancer Res.* 62(15):4289-4294, 2002.
Houston et al., "Quality analysis of in vivo near-infrared fluorescence and conventional gamma images acquired using a dual-labeled tumor-targeting probe," *J Biomed. Optics* 10:054010-1 to 054010-11, 2005.
Kabolizadeh et al., "The role of cetuximab in the management of head and neck cancers," *Exp Opin Biol Ther.* 12(4):517-528, 2012.
Lee et al., "Peptides and Peptide Hormones for Molecular Imaging and Disease Diagnosis," *Chem Rev.* 110(5):3087-3111, 2010.
Li et al., "Structural basis for inhibition of the epidermal growth factor receptor by cetuximab," *Cancer Cell* 7(4):301-311, 2005.
Master et al., "A Cell-targeted Photodynamic Nanomedicine Strategy for Head & Neck Cancers," *Mol Pharm.* 10:1988-1997, 2013.
Medical Sci Digest., 2004, vol. 30, p. 545-548 (In Japanese, with concise description in English).
New Pharmacology (New Yakurigaku), Nankodo Co., Ltd., 2012, the third impression of the revised sixth edition, p. 558-559 (4 pages). (In Japanese, with translation).
Peng et al., "A nonfluorescent, broad-range quencher dye for Förster resonance energy transfer assays," *Anal Biochem.* 388(2):220-228, 2009.
Sekkat et al., "Like a bolt from the Blue: Phthalocyanines in Biomedical Optics," *Molecules* 17:98-144, 2012.
Sharman et al., "Targeted Photodynamic Therapy Via Receptor-Mediated Delivery Sytems," *Adv Drug Deliv Rev.* 56(1):53-76, 2004.
Turner et al., "Administration of substances to laboratory animals: routes of administration and factors to consider," *J Am Assoc Lab Anim Sci.* 50(5):600-613, 2011.
Van Cutsem et al., "Cetuximab and chemotherapy as initial treatment for metastatic colorectal cancer," *N Engl J Med.* 360:1408-1417, 2009.
Van Cutsem et al., "Intrapatient cetuximab dose escalation in metastatic colorectal cancer according to the grade of early skin reactions: the randomized EVEREST study," *J Clin Oncol.* 30(23):2861-2868, 2012.
Wollina, "Cetuximab in non-melanoma skin cancer," *Exp Opin Biol Ther.* 12(7):949-956, 2012.
Dancey et al., "Phase I Trial of the 131I-Labelled Anti-CD25 Antibody Basiliximab in the Treatment of Patients with Relapsed or Refractor Lymphoma," *Blood* 110:648, 2007.
Kuhn et al., "The Role of Interleukin-2 Receptor Alpha in Cancer," *Frontiers in Bioscience* 10:1462-1474, 2005.
Simpson et al., "Fc-dependent depletion of tumor-infiltrating regulatory T cells co-defines the efficacy of anti-CTLA-4 therapy against melanoma," *J Exp Med.* 210:1695-1710, 2013.

* cited by examiner

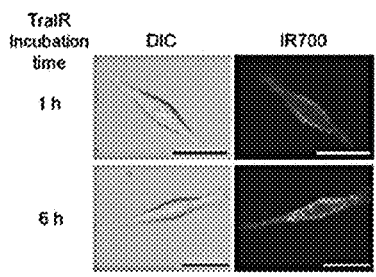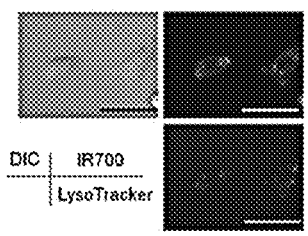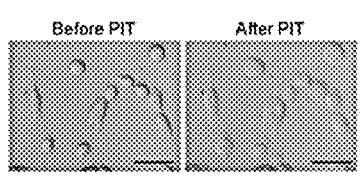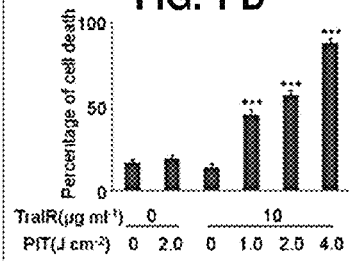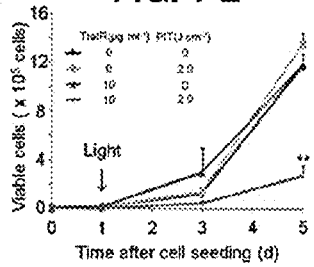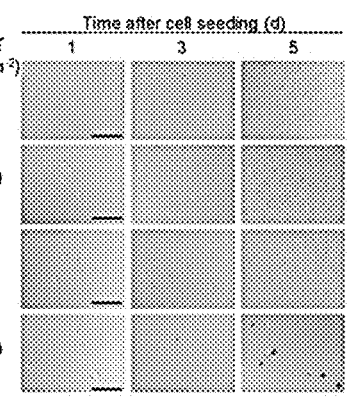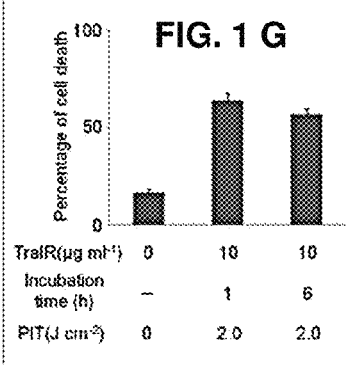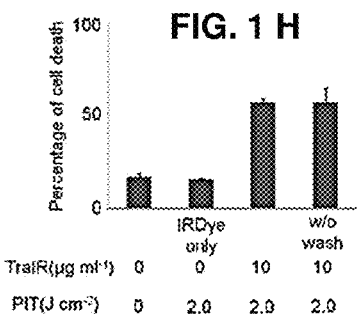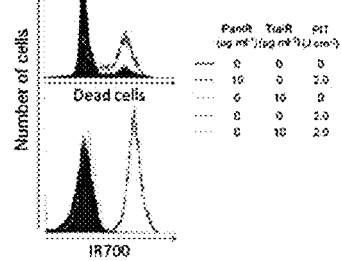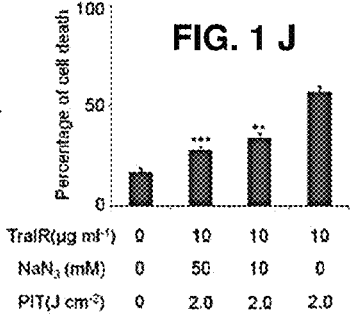

FIG. 6 A
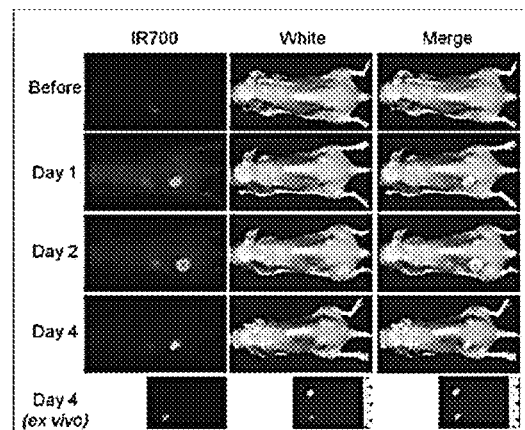
FIG. 6 B
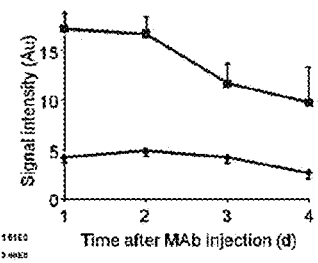
FIG. 6 C
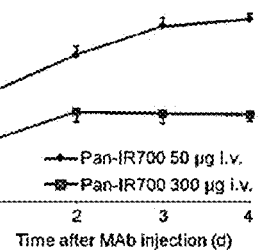
FIG. 6 D
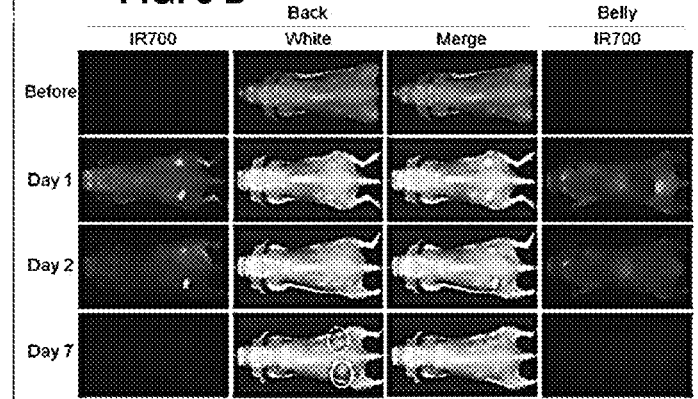
FIG. 6 E
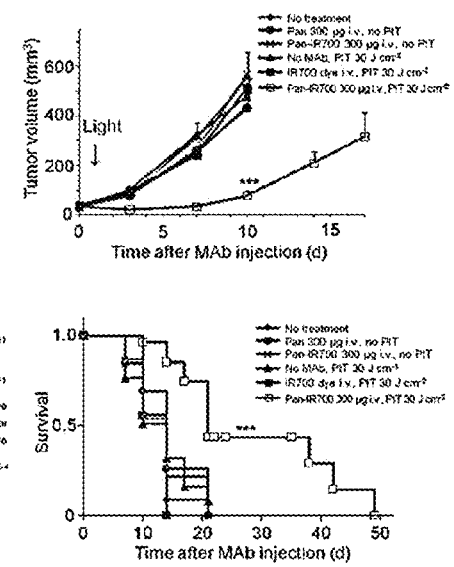
FIG. 6 F
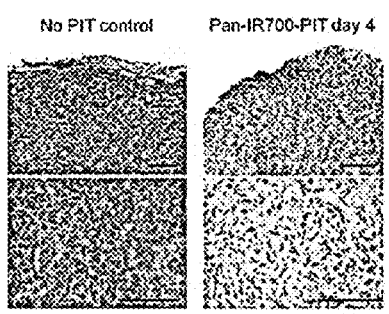
FIG. 6 G

FIG. 7
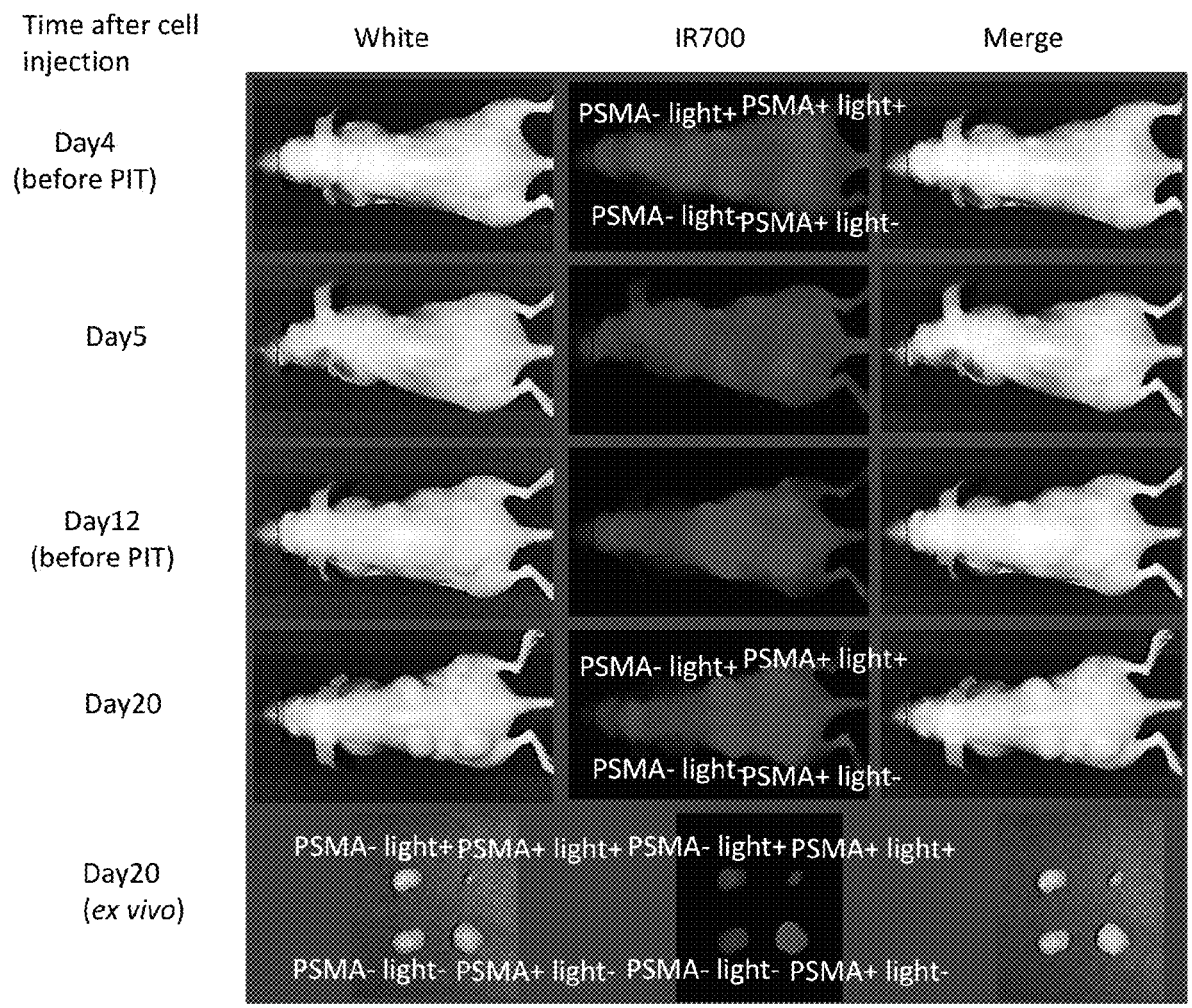
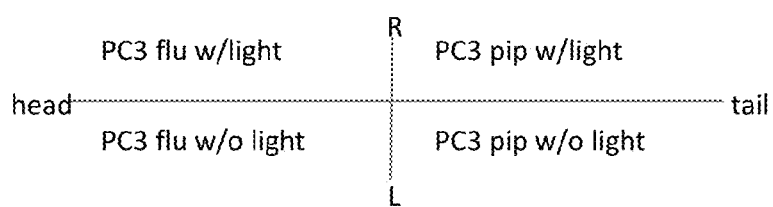

FIG. 9 A
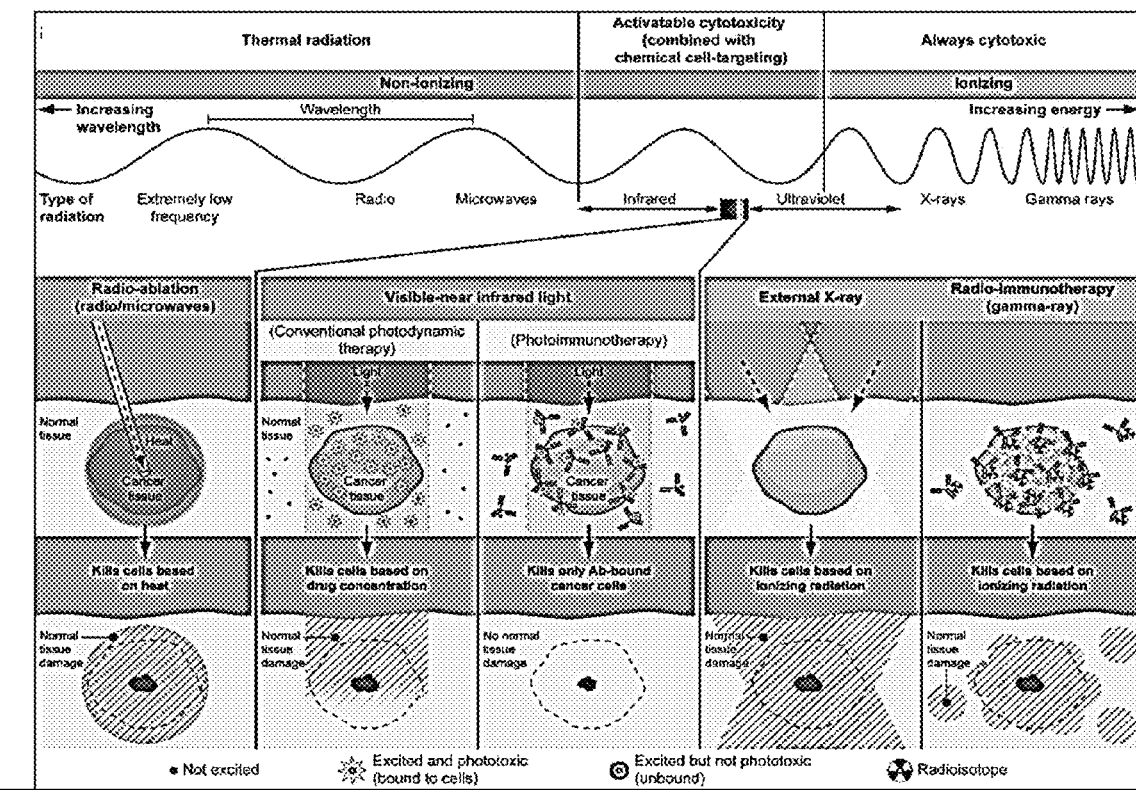
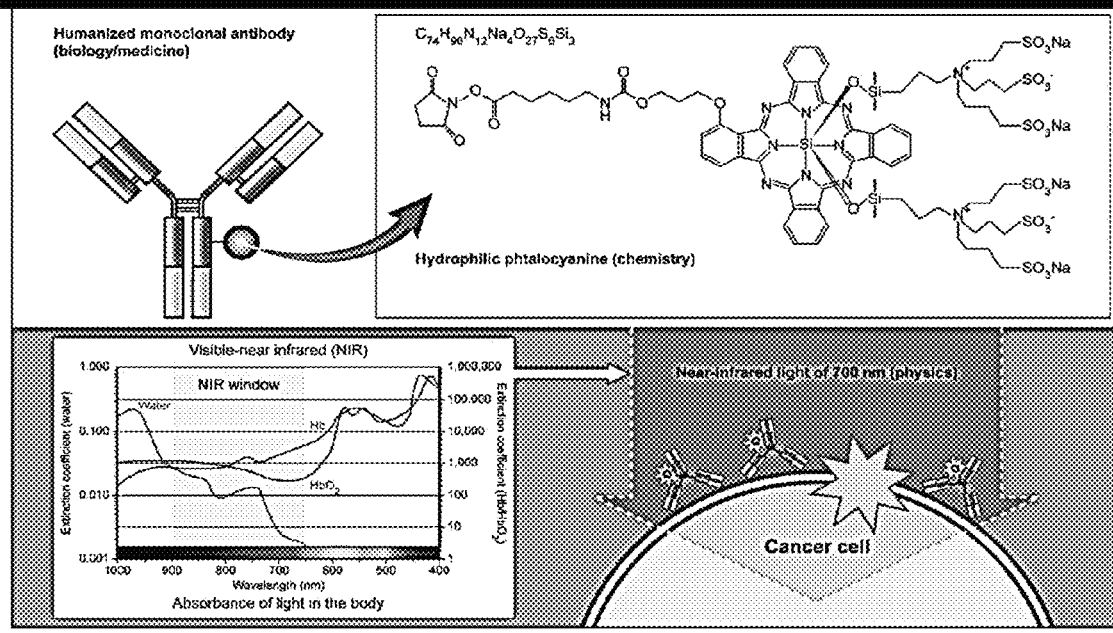
FIG. 9 B

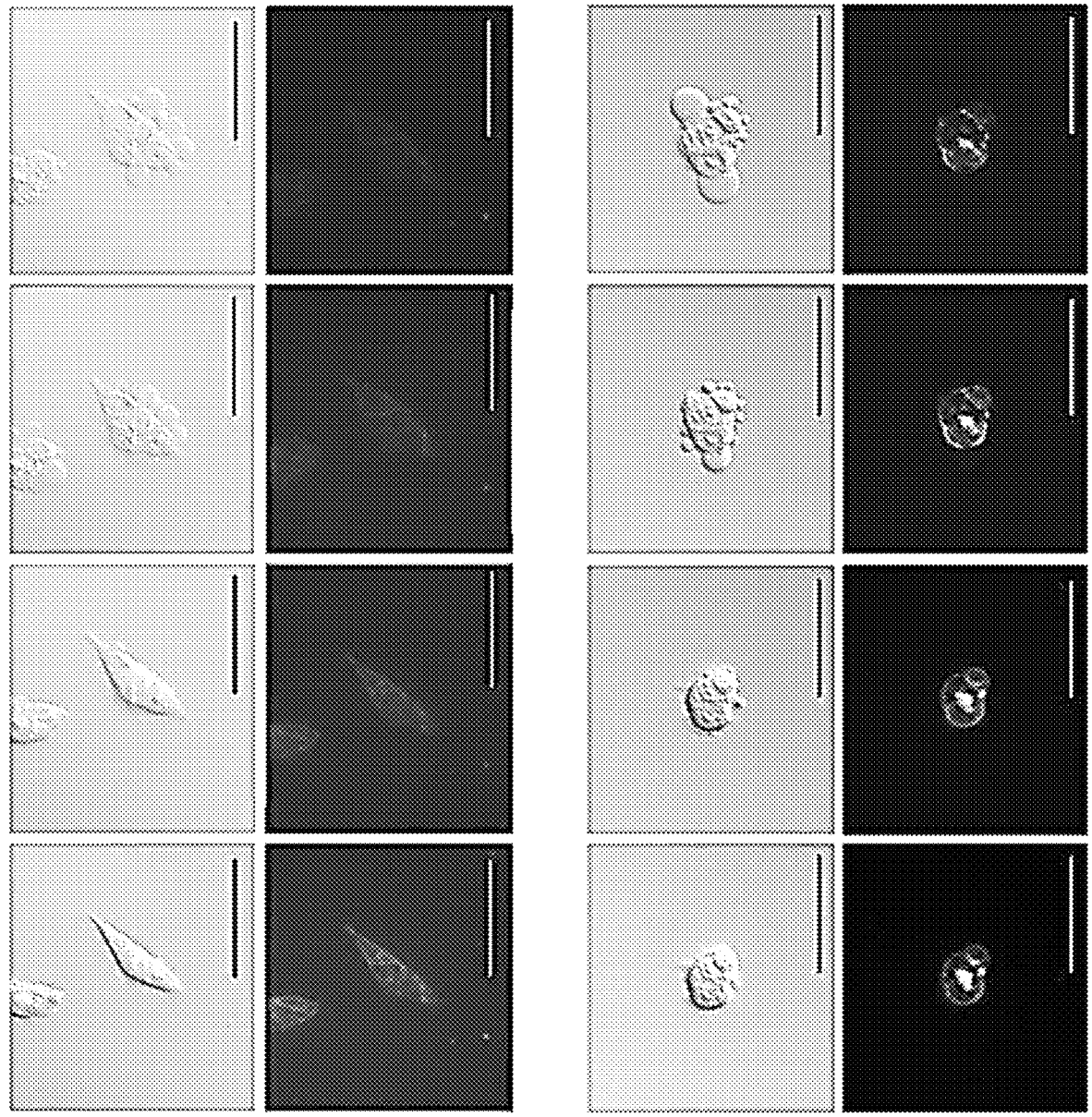

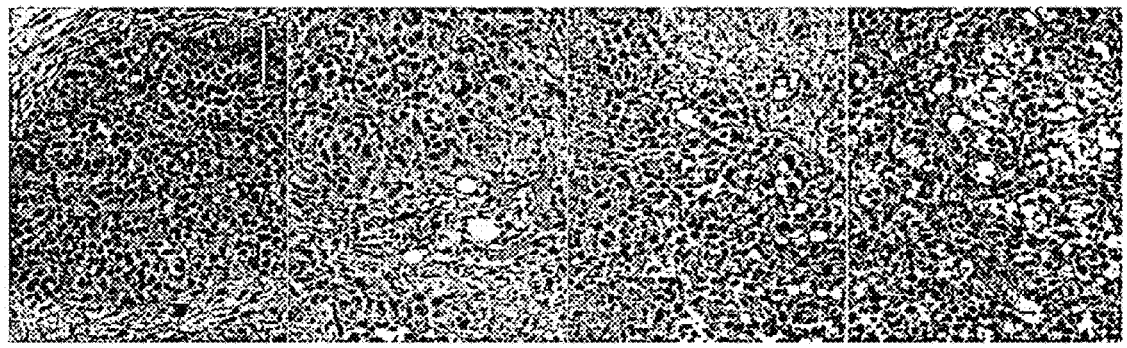
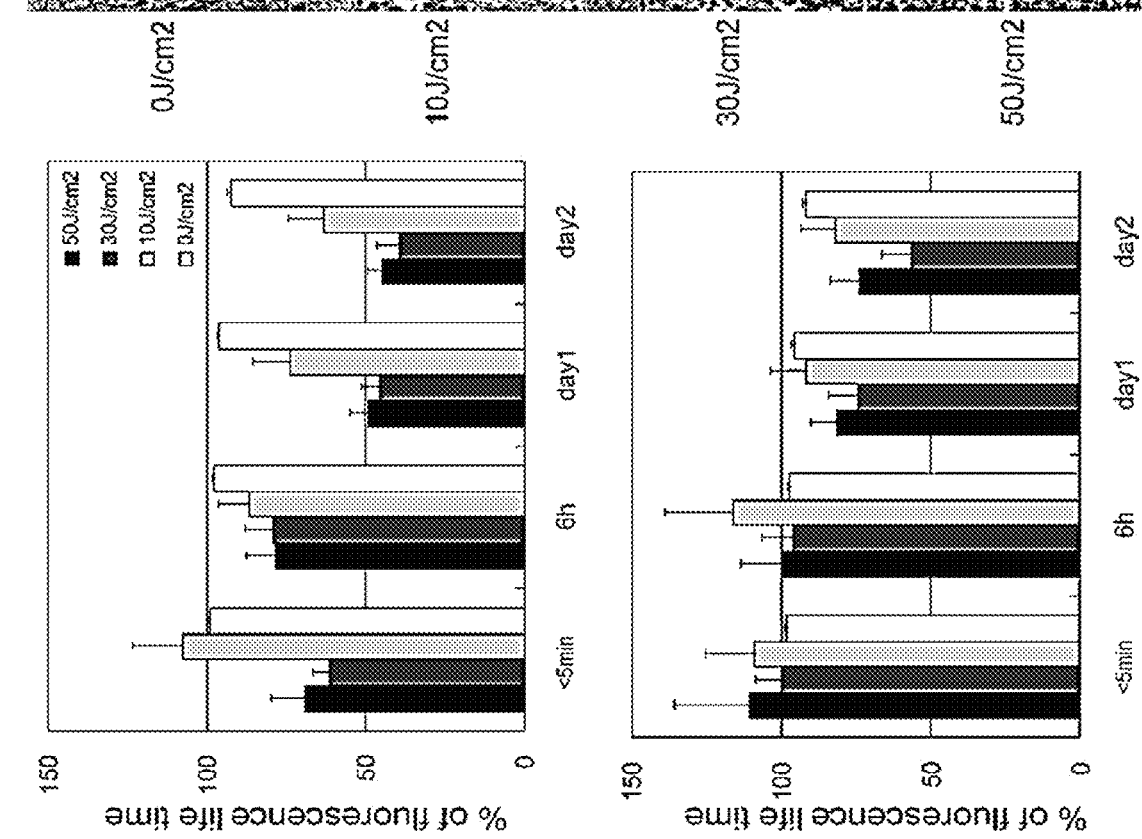
FIG. 13 A
FIG. 13 B
FIG. 13 C

FIG. 15B
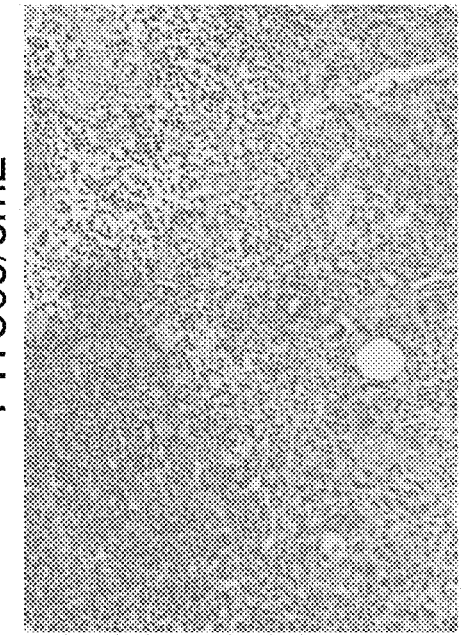
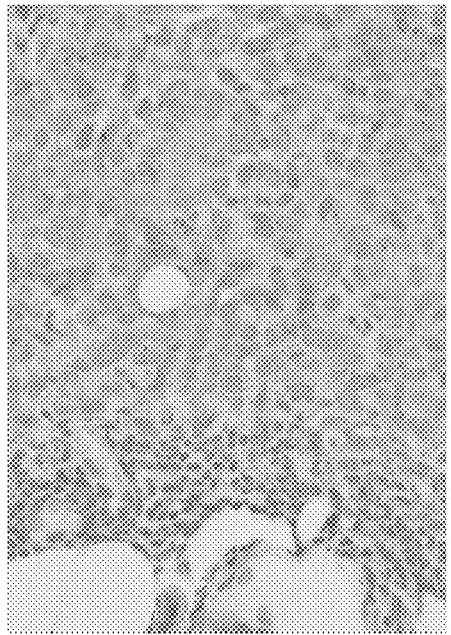
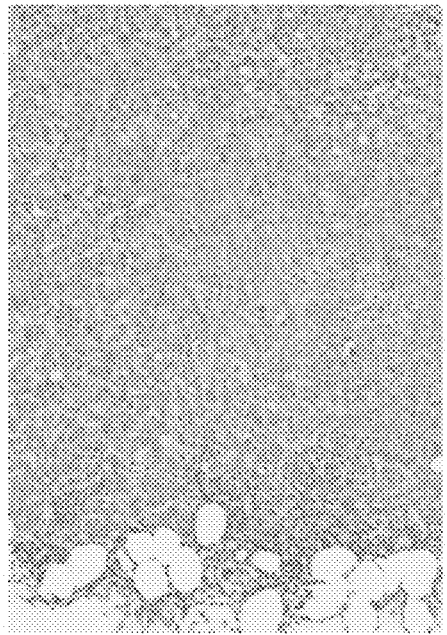

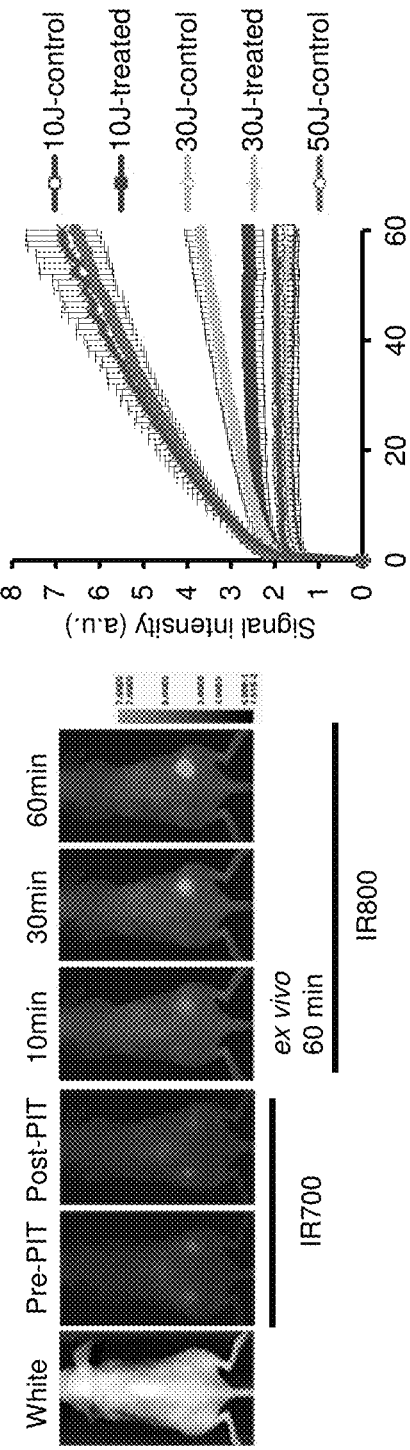
FIG. 16 A
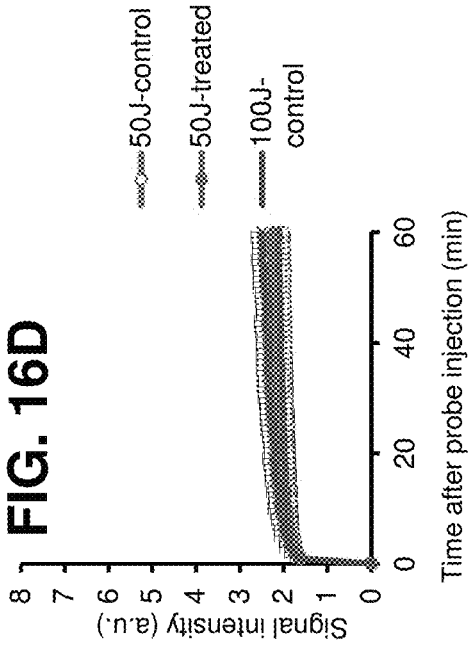
FIG. 16B
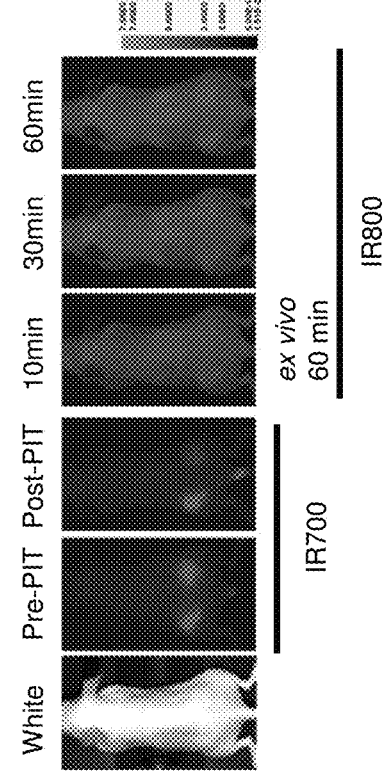
FIG. 16 C
FIG. 16D

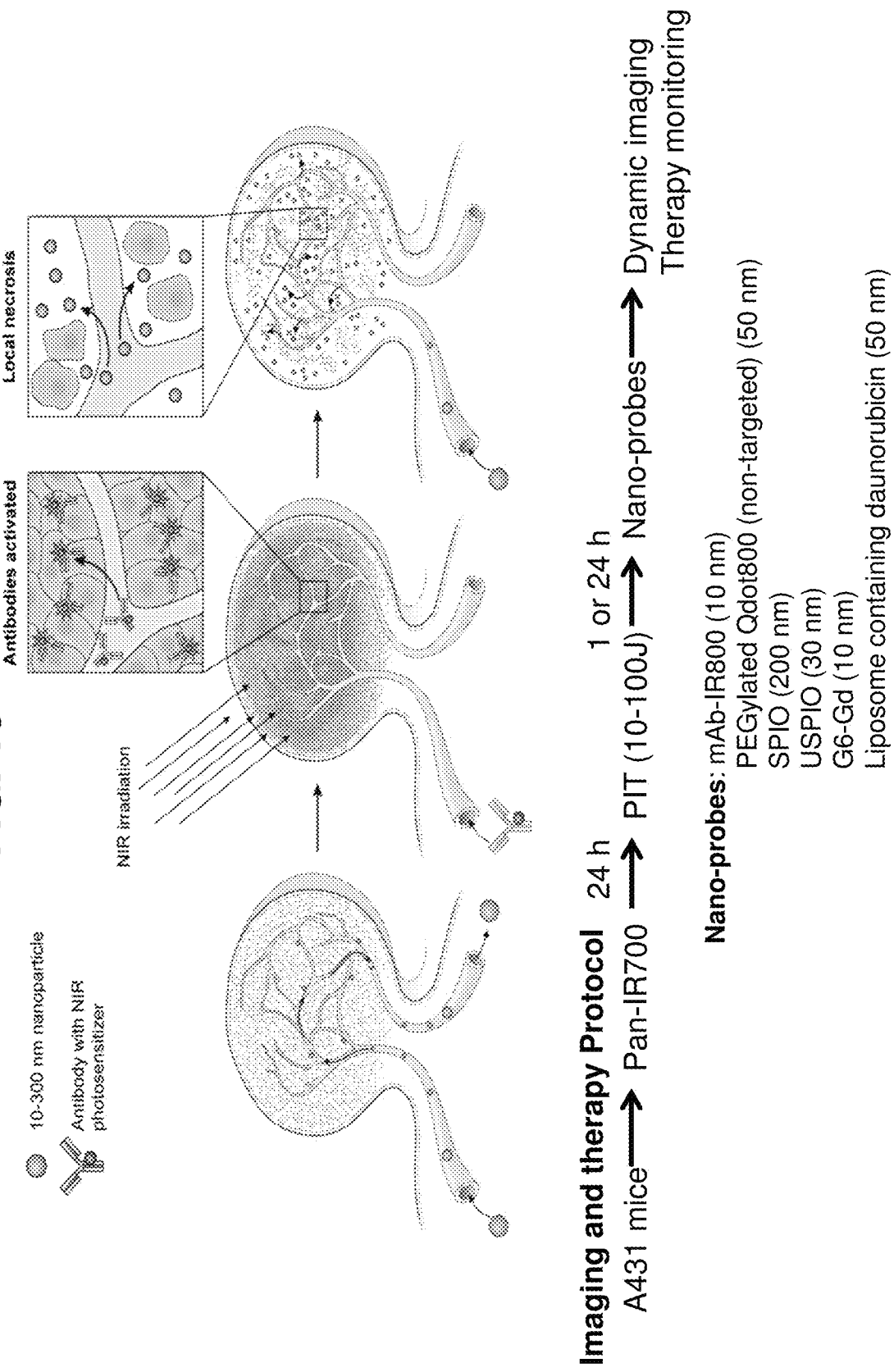

PHOTOSENSITIZING ANTIBODY-FLUOROPHORE CONJUGATES

CROSS-REFERENCE TO RELATED APPLICATIONS

This application is a continuation of U.S. Ser. No. 14/868,040 filed Sep. 28, 2015, which is a divisional of U.S. Ser. No. 14/126,060 filed Dec. 13, 2013, now U.S. Pat. No. 9,358,306, which is the U.S. National Stage of International Application No. PCT/US2012/044421, filed Jun. 27, 2012, which was published in English under PCT Article 21(2), which is a continuation-in-part of U.S. application Ser. No. 13/180,111 filed Jul. 11, 2011, now U.S. Pat. No. 8,524,239, which claims priority to U.S. Provisional Application No. 61/363,079, filed Jul. 9, 2010, all herein incorporated by reference.

FIELD OF THE DISCLOSURE

This application relates to antibody-IR700 conjugates, and methods of their use to kill cells that specifically bind to the antibody following irradiation with infrared (NIR) light. Also provided are devices that incorporate NIR light emitting diodes (LEDs) that can also be used with the disclosed conjugates and methods.

BACKGROUND

Cancer was responsible for about 13% of all human deaths in 2007. Although there are several therapies for cancer, there remains a need for therapies that effectively kill the tumor cells while not harming non-cancerous cells.

In order to minimize the side effects of conventional cancer therapies, including surgery, radiation and chemotherapy, molecular targeted cancer therapies have been developed. Among the existing targeted therapies, monoclonal antibodies (MAb) therapy have the longest history, and to date, over 25 therapeutic MAbs have been approved by the Food and Drug Administration (FDA) (Waldmann, *Nat Med* 9:269-277, 2003); Reichert et al., *Nat Biotechnol* 23:1073-1078, 2005). Effective MAb therapy traditionally depends on three mechanisms: antibody-dependent cellular cytotoxicity (ADCC), complement-dependent cytotoxicity (CDC), and receptor blockade and requires multiple high doses of the MAb. MAbs have also been used at lower doses as vectors to deliver therapies such as radionuclides (Goldenberg et al., *J Clin Oncol* 24, 823-834, 2006) or chemical or biological toxins (Pastan et al., *Nat Rev Cancer* 6:559-565, 2006). Ultimately, however, dose limiting toxicity relates to the biodistribution and catabolism of the antibody conjugates.

Conventional photodynamic therapy (PDT), which combines a photosensitizing agent with the physical energy of non-ionizing light to kill cells, has been less commonly employed for cancer therapy because the current non-targeted photosensitizers are also taken up in normal tissues, thus, causing serious side effects, although the excitation light itself is harmless in the near infrared (NIR) range (FIG. 9).

SUMMARY OF THE DISCLOSURE

Provided herein are antibody-IR700 molecules and methods of their use for killing a target cell, such as a tumor cell. In particular examples the methods are specific in that non-target cells, such as normal cells, are not killed in significant numbers (such as less than 1% of normal cells are killed), but the target cells are. In particular examples the method includes contacting a cell having a cell surface protein with a therapeutically effective amount of an antibody-IR700 molecule, wherein the antibody (or other specific binding agent) specifically binds to the cell surface protein. Specific non-limiting examples of antibody-IR700 molecules include Panitumumab-IR700, Trastuzumab-IR700, and HuJ591-IR700. The cell is irradiated at a wavelength of 660 to 740 nm, such as 660 to 710 nm (for example, 680 nm) at a dose of at least 1 J cm$^{-2}$ (such as at least 50 J cm$^{-2}$). The method also includes contacting the cell with one or more therapeutic agents (such as an anti-cancer agent), for example within about 8 hours after irradiating the cell, thereby killing the cell. Such methods can further include detecting the cell with fluorescence lifetime imaging (FLT), for example about 0 to 48 hours after irradiating the cell, thereby permitting detection of cell killing in real-time.

Also provided are methods of detecting cell killing in real-time. Such methods can include contacting a cell comprising a cell surface protein with a therapeutically effective amount of one or more antibody-IR700 molecules as described above, irradiating the cell at a wavelength of 660 to 740 nm and at a dose of at least 30 J cm$^{-2}$ (such as a dose sufficient to shorten IR700 FLT by at least 25% for example 30 to 50 J cm$^{-2}$), and detecting the cell with fluorescence lifetime imaging about 0 to 48 hours (such as at least 6 hours) after irradiating the cell, thereby detecting the cell killing in real-time.

Any target cell can be killed (and in some examples detected in real-time) with the disclosed antibody-IR700 molecules and methods, for example by using one or more antibodies that binds to one or more proteins on the target cell surface (such as a receptor), wherein the protein(s) on the target cell surface is not significantly found on non-target cells (such as normal healthy cells) and thus the antibody will not significantly bind to the non-target cells. In one example the cell surface protein is a tumor-specific protein, such as HER1, HER2, or PSMA.

In some examples, the cell to be killed is present in a subject. In such examples, the method can include administering a therapeutically effective amount of the antibody-IR700 molecule to the subject and irradiating the subject, for example irradiating a tumor in the subject. In some examples, the method can further include selecting a subject with a tumor that expresses a cell surface protein that can specifically bind to the antibody-IR700 molecule.

Also provided are devices, such as those that can be worn by a patient. Such devices can include an article of clothing, jewelry, or a covering, and a near infrared (NIR) light emitting diode (LED) that is incorporated into the article of clothing, jewelry, or covering. Such devices can further include power and/or cooling sources. This permits the patient to wear the device (or be covered by the device) for extended periods of time, thus permitting treatment of tumor cells present in the blood or circulatory system. Methods of using the device are also provided.

The foregoing and other features of the disclosure will become more apparent from the following detailed description of a several embodiments which proceeds with reference to the accompanying figures.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 1A is a digital image showing the labeling of cells with a Trastuzumab-IR700 conjugate (Tra-IR700) at 4° C. for 1 hour or 37° C. for 6 hours. Light images also shown. Scale bar, 30 μm.

FIG. 1B is a digital image showing the lysosomal localization of Tra-1R700 6 h after incubation. Scale bar, 50 μm.

FIG. 1C is a digital image showing is a digital image showing before and after incubation with Tra-IR700 at 37° C. for 6 hours followed by photoimmunotherapy (PIT). Scale bar, 50 μm.

FIG. 1D is a bar graph showing the irradiation dose dependent and target specific cell death in response to Tra-1R700 mediated PIT. Data are means±s.e.m. (n=at least 4, ***P<0.001 vs. non treatment control, Student's t test).

FIG. 1E is a bar graph showing the long term growth inhibition in response to Tra-1R700 mediated PIT. Data are means±s.e.m. (n=3, **P<0.01 vs. non treatment control, Student's t test).

FIG. 1F is a digital image showing the microscopic observation of growth inhibition in response to TraIR700 mediated PIT. Scale bar, 100 μm FIG. 1G is a bar graph showing that internalization of Tra-1R700 was not required for phototoxic cell death. Data are means±s.e.m. (n=3).

FIG. 1H is a bar graph showing that target specific membrane binding of Tra-1R700 only induced phototoxic cell death. Data are means±s.e.m. (n=3).

FIG. 1I is a graph showing that HER2 negatively expressing A431 cells did not show phototoxic effects with Tra-1R700 mediated PIT (n=3).

FIG. 1J is a bar graph showing sodium azide ($NaN_3$) concentration dependent inhibition of phototoxic cell death induced by Tra-1R700 mediated PIT. Data are means±s.e.m. (n=3, *P<0.001, P<0.01 vs. 2.0 J cm-2 PIT treatment without NaN3 control, Student's t test). DIC: differential interference contrast. PanIR: Pan-1R700.

FIG. 7 is a digital image showing the biodistribution of J591-1R700. PC3-PIP tumors were selectively visualized with IR700 fluorescence after J591-1R700 injection (100 μg). Right side of the tumor was irradiated with near infrared (NIR) light on days 4, 12, and 13 while left side of the tumor was covered with black tape.

Tumor shrinkage was confirmed on day 5.

Figure 8:
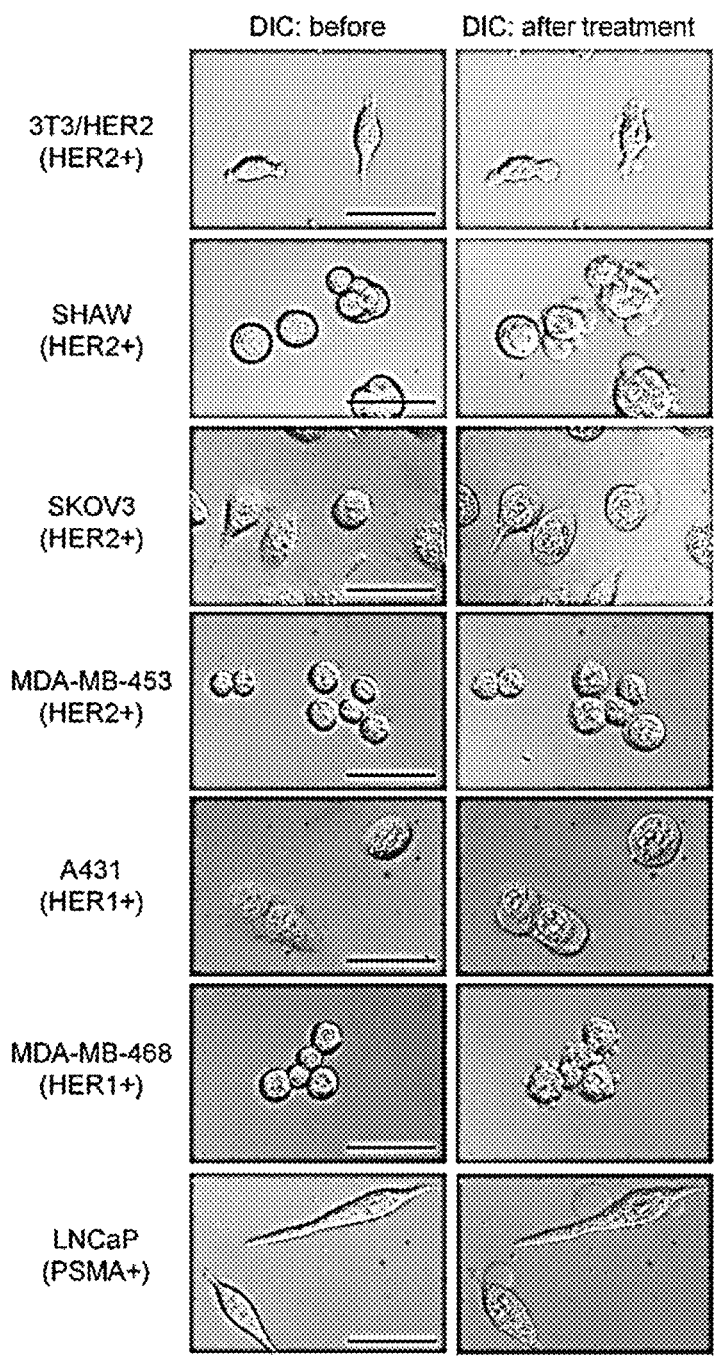

FIG. 8 is a digital image showing the microscopic observation of before and after PIT for various cells in the presence of with Tra-1R700 for HER2+ cells, Pan-IR700 for HER1+ cells, and huJ591-1R700 for PSMA+ cells. Scale bar, 50 μm. DIC: differential interference contrast.

FIG. 9A is a schematic drawing showing a schema for explaining selective cancer therapy with PIT in the context of other physical cancer therapies employing electro-magnetic wave irradiation. Although other physical cancer therapies induce different types of damages in the normal tissue, PIT dedicatedly damages cancer cells without damaging normal cells or tissues.

FIG. 9B is a schematic drawing showing a schema for explaining photo-physical, chemical and biological basis of PIT. Humanized antibodies are employed as a delivery vehicle because of its highest binding specificity, greatest in vivo target delivery, low immunogenecity among the clinically applicable targeting reagents. A hydrophilic phtalocyanine is employed as an activatable cytotoxic "Nano-dynamite" reagent because of its great absorption of near infrared light of 700 nm and strong cytotoxicity induced only when associating with the cell membrane. Near infrared light of 700 nm is employed as an initiator for activating cytotoxicity because of its high energy among non-harmful non-ionizing photons and great in vivo tissue penetration.

FIGS. 10A-D. Samples of 1R700-conjugated Panitumumab (Pan-1R700) at concentrations of 2.5, 5, 20, and 40 jag/mL were prepared by diluting with PBS. (A) Fluorescence intensity image of Pan-IR700 solution: Fluorescence intensities were decreased according to decrease of concentration of Pan-1R700. (B) Fluorescence lifetime (FLT) image of Pan-1R700 solution: The FLT at various concentrations of Pan-1R700 solutions was almost the same value, 3.56+/−0.081 ns; 3.62 (2.5 pg/mL), 3.58 (5 pg/mL), 3.44 (20 pg/mL), 3.60 ns (40 pg/mL). (C) LED light-irradiation for A431 cell pellets changes FLTs. A431 cell line incubated with Pan-IR700 for 24 hours were treated with PIT at doses of 0, 8, 15 and 30 J/cm². FLT shortened to 3.09, 2.94 and 2.85 ns, compared with 3.28 ns before light exposure. These represented shortenings of 9.1, 10.1 and 13.1%, respectively. (D) FLT of A431 pellets depends on the incubation time with Pan-IR700. FLT values escalate with incubation time with Pan-IR700. FLT changes from 2.98 ns (1 hour) to 3.42 ns (24 hours).

FIG. 11 is a digital image showing serial fluorescence (lower) and differential interference contrast (DIC) microscopic images (upper) of A431 cells, which were pre-incubated with Pan-IR700 (10 jig/m0 at 37° C. for 24 h, 5, 15, 60 and 90 sec after start exposing NIR light. Pan-IR700 gradually internalized into cytoplasm in A431 cells after bound to cell membrane up to 24 h post-injection. Morphological changes on DIC become severer by exposing more dose of NIR light. Scale bars, 50 μm.

FIGS. 12A-D. Comparison with FLTs of irradiated tumors (dark gray bar) and non-irradiated tumors (bright gray bar). (A) FLT images before and after PIT at the dose of 10, 30, 50 J/cm² in the same mouse which was inoculated with A431 cells on both sides of the mouse dorsum. Right-sided tumor was treated by PIT whereas the left was covered. FLTs of A431 tumors treated with PIT with 50 J/cm² (B), 30 J/cm² (C) and 10 J/cm², (D) were plotted. PIT with the NIR light dose of 30 and 50 J/cm² demonstrated significant (P<0.05) shortenings in FLT immediately, compared with non-irradiated tumors. However, FLT did not significantly shorten at a low dose of 10 J/cm². Transient prolongations of FLTs were observed at 6 hours after PIT likely due to uptake by reactive macrophages. Mann-Whitney's U test was used for the statistical analysis.

FIGS. 13A-C. (A) FLT in PIT treated tumors with 50 and 30 J/cm² shortened significantly (p<0.01) compared with no treatment control (0 J/cm²) (control). FLTs were immediately shortened to 69.1+/−10.9% and 61.5+15.1% by PIT with 50 and 30 J/cm2, respectively. A431 tumors irradiated with only 10 J/cm² showed no significant shortening of FLT immediately after PIT. FLT shortened by only 7.7% at 48 hours after PIT compared with no treatment control. (B) FLT of non-irradiated tumors in PIT treated mice shortened slightly more than that in the untreated mice over time, but these changes were not significant. Student's t test was used for the statistical analysis. (C) Histological specimens of A431 tumors, which were treated with PIT at 0, 10, 30, and 50 J/cm², are shown. All specimens are stained with Hematoxylin and Eosin. Microscopic evaluation of treated tumors revealed various degrees of necrosis and micro-hemorrhage with clusters of healthy or damaged tumor cells after PIT. Necrotic damage was diffuse and intense and fewer surviving tumor cells are seen, when 30 and 50 J/cm² of NIR light was administered. In contrast, when only 10 J/cm² of NIR light was administered, necrotic cell damage was found in only limited areas within the tumor while substantial amounts of healthy cancer foci remained. Scale indicates 50 μm.

Figure 14:
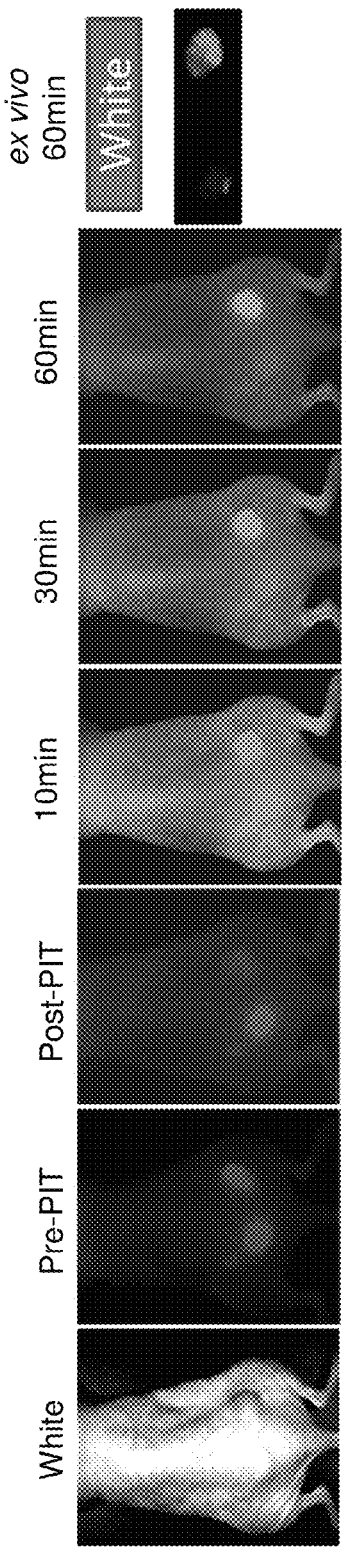
Figure 14C:
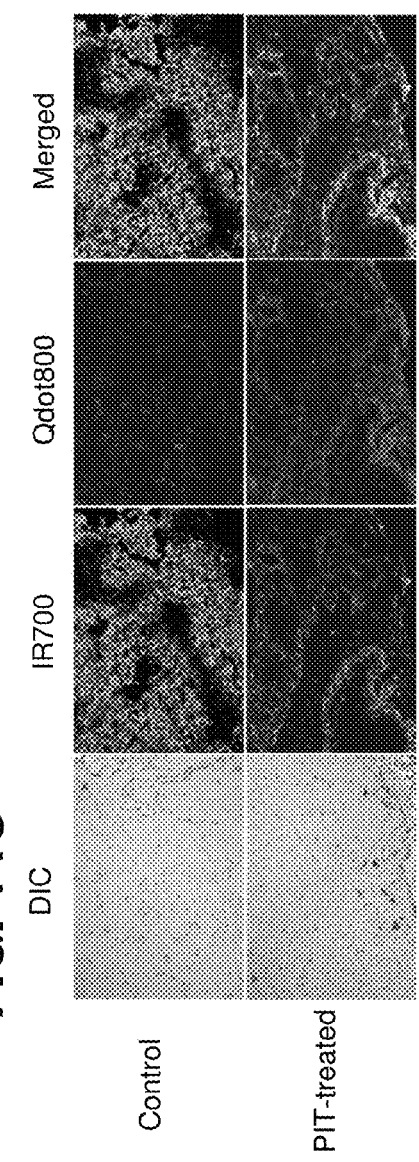
Figure 14B:
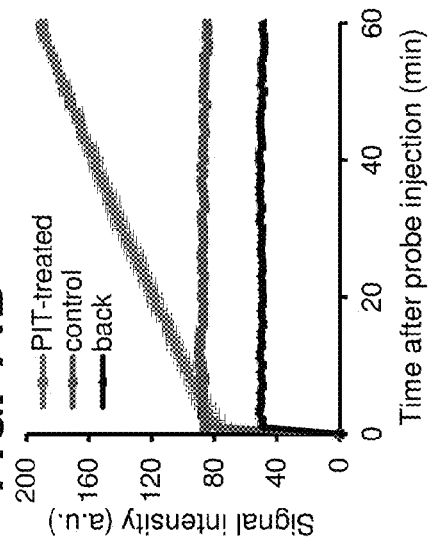

FIG. 14A-C. A. The dynamic images of PEGylated Qdot800 after PIT. A431 mice were injected with Pan-IR700, and 24 h later, NIR light (50 J/cm2) were irradiated to the right side tumor. Qdot800 was administered 1 hour after PIT treatment. Only the right sided tumor was clearly shown within 10 minutes. B. Time-signal intensity curves in the PIT-treated tumor (green; top), control tumor (blue; middle), and back (black; bottom). C. Fluorescence microscopy. IR700 signal shows the survived A431 cells. Qdot800 was broadly distributed in the PIT-treated tumor tissues and co-localization of IR700 and Qdot800 was partially observed, whereas, the signals of Qdot800 in control tumors were localized in the vicinity of main blood vessels.

Figure 15A:
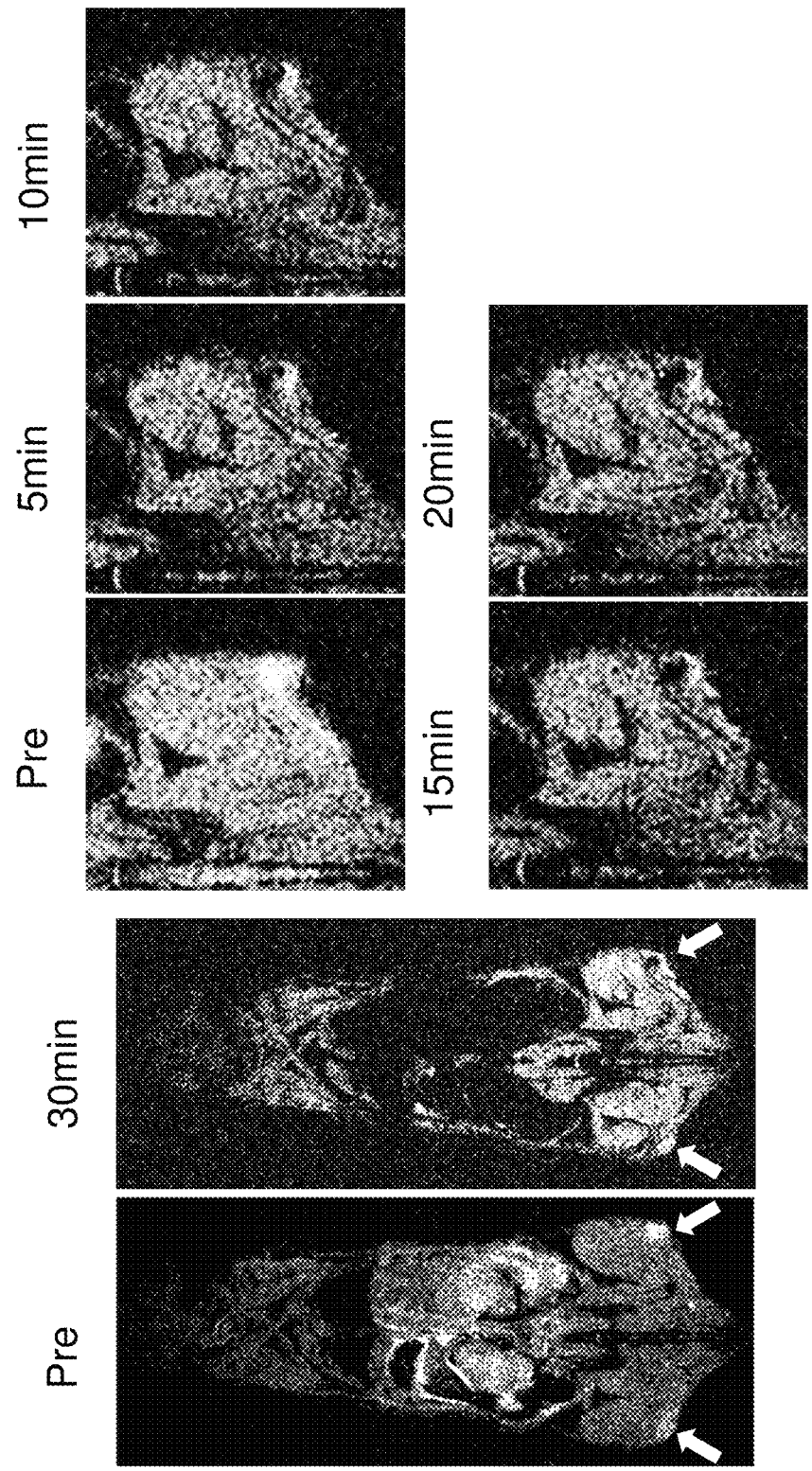

FIGS. 15A-15B. A. The dynamic images of SPIO after PIT. A431 mice were injected with Pan-IR700, and 24 h later, NIR light (50 J/cm2) were irradiated to the right side tumor. SPIO was administered 1 h after PIT treatment. Only the right-sided tumor was clearly shown up within 5 min. B. Prucian blue staining and HE staining.

FIGS. 16A-16D. A. The dynamic images of Pan-IR800 after PIT. A431 mice were injected with Pan-IR700, and 24 h later, NIR light (50 J/cm2) were irradiated to the right side tumor. Pan-IR800 was administered 1 h after PIT treatment. Only the right sided tumor was clearly shown up within 10 min. B. Pan-IR800 can be quickly accumulated in the PIT-treated tumors in dependent on irradiated light dose. Signal was not observed in the control tumors. C and D. 24 h after PIT, Pan-IR800 cannot be taken up by the tumor, likely because basement of blood vessels was repaired (intrestitaial pressure was recovered) or blood flow was stopped.

FIGS. 17A-F. A-C The dynamic images of daunorubicin containing liposome after PIT. A431 mice were injected with Pan-IR700, and 24 h later, NIR light (50 J/cm2) were irradiated to the right side tumor. Daunorubicin containing liposome was administered 1 h after PIT treatment. Only the right sided tumor was clearly shown up within 30 min. D. Fluorescence microscopic studies. IR700 signal shows the survived A431 cells. Daunorubicin containing liposome was broadly distributed in the PIT-treated tumor tissues and co-localization of IR700 and Qdot800 was partially observed, whereas, the signals of Qdot800 in control tumors were localized in the vicinity of main blood vessels. E. The combination therapy combined PIT with liposomes containing daunorubicin significantly suppressed tumor growth and (F) prolonged survival time of A431 bearing mice.

FIG. 18 provides a schematic drawing showing an exemplary method for treating tumors using PIT and chemotherapeutics, which can include imaging of the tumor.

Figure 19A:
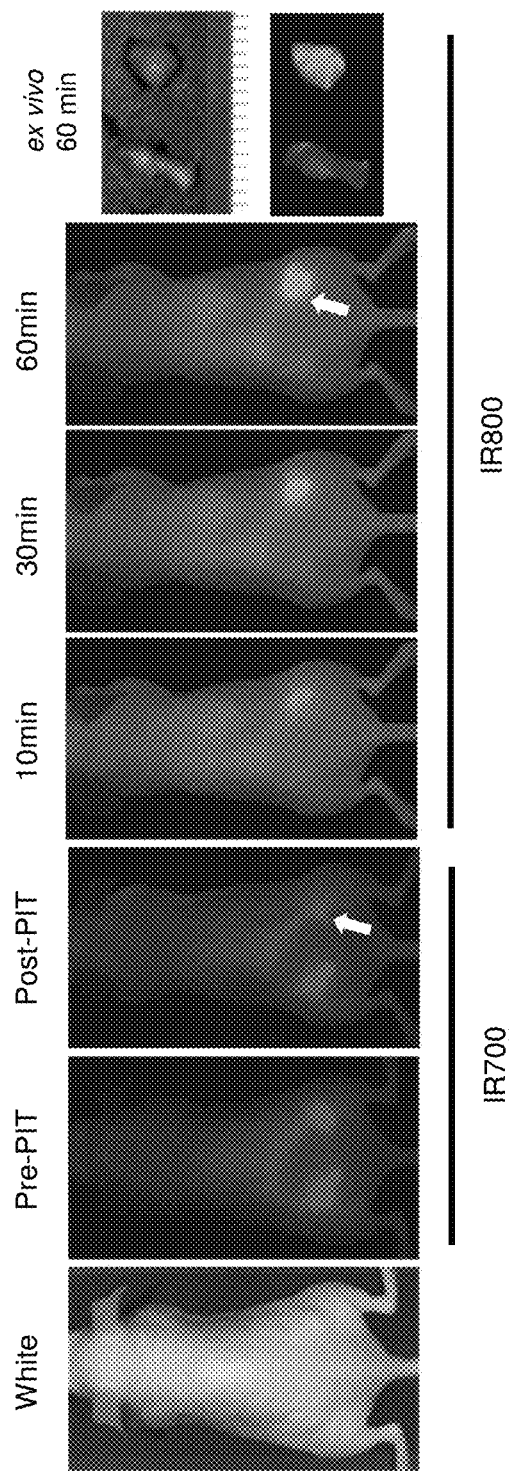
Figure 19B:
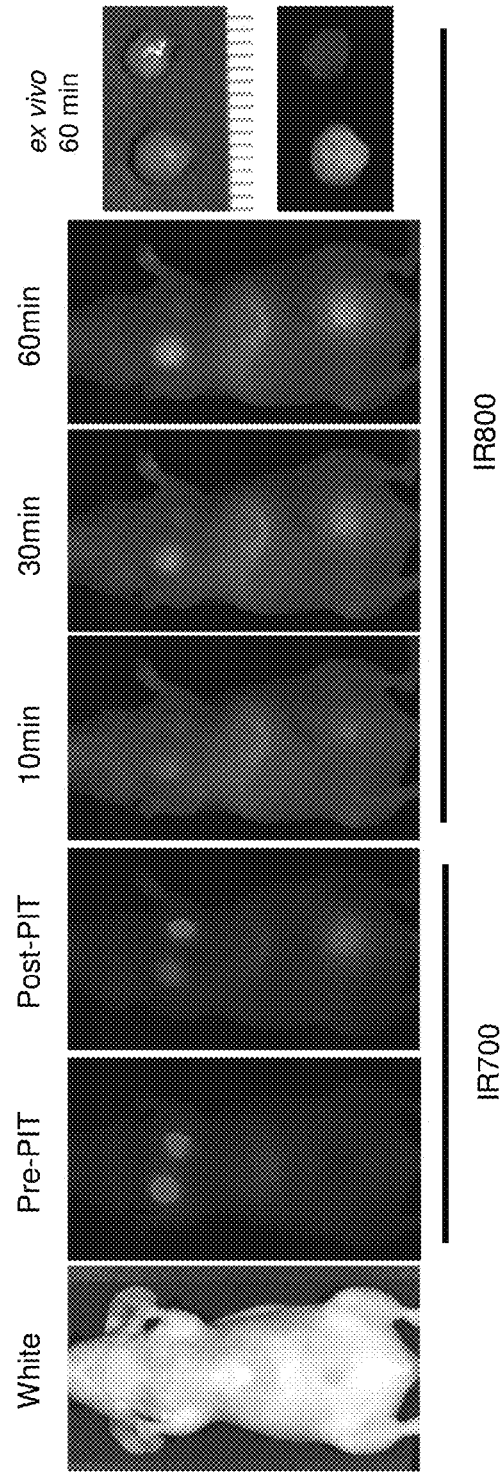

FIGS. 19A-19B. A. The dynamic images of Tra-IR800 after PIT. 3T3/HER2 mice were injected with Tra-IR800, and 24 h later, NIR light (50 J/cm2) were irradiated to the right side tumor. Tra-IR800 was administered 1 h after PIT treatment. Only the right sided tumor was clearly shown up within 10 min. White arrows show the site where light was insufficiently irradiated to the 3T3HER2 tumors. Tra-IR800 can be accumulated in only the regions where the tumor was exposed to NIR light. B. The dynamic images of Pan-IR800 after PIT. MDA-MB-468 bearing mice were injected with Pan-IR700, and 24 h later, NIR light (50 J/cm2) were irradiated to the right side tumor. Pan-IR800 was administered 1 h after PIT treatment. Only the right sided tumor was clearly shown up within 10 min.

Figure 20A:
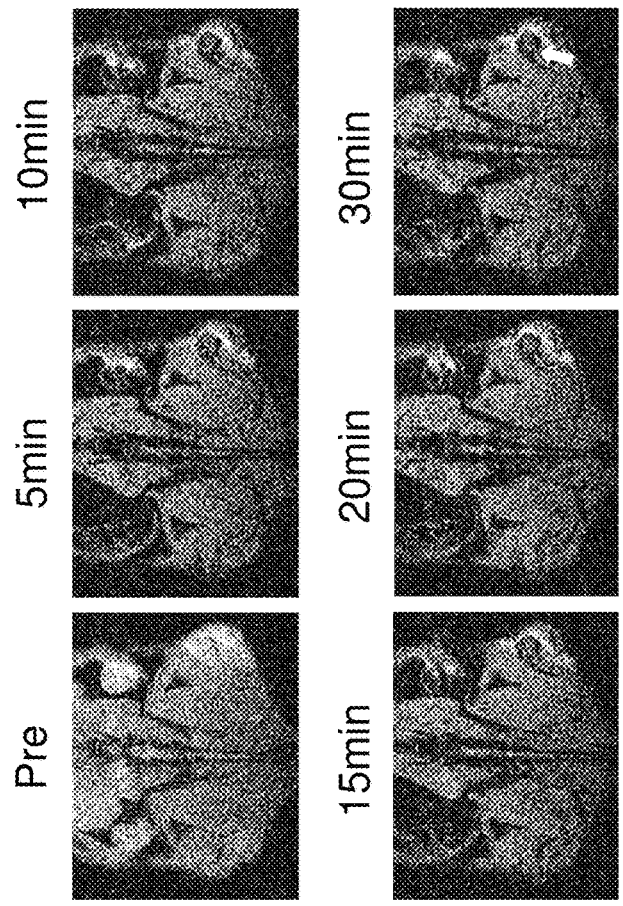
Figure 20C:
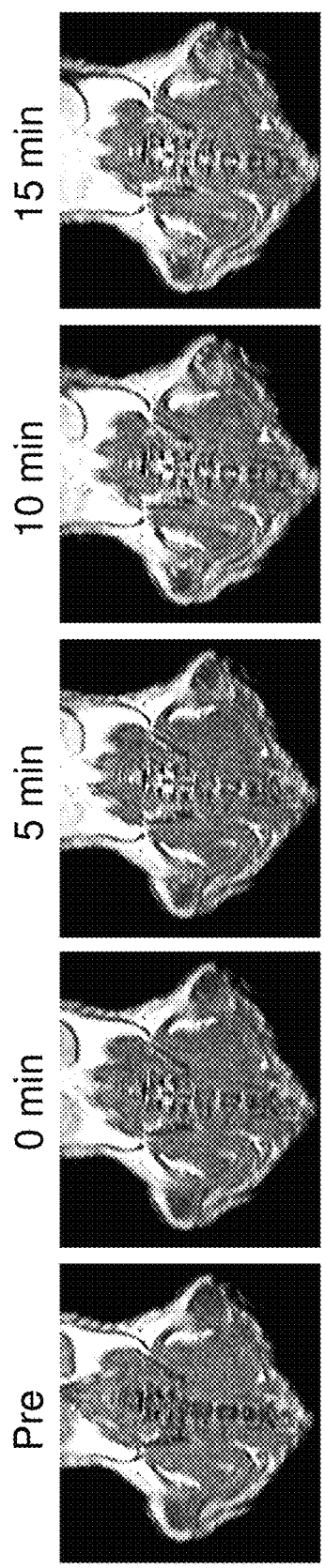
Figure 20B:
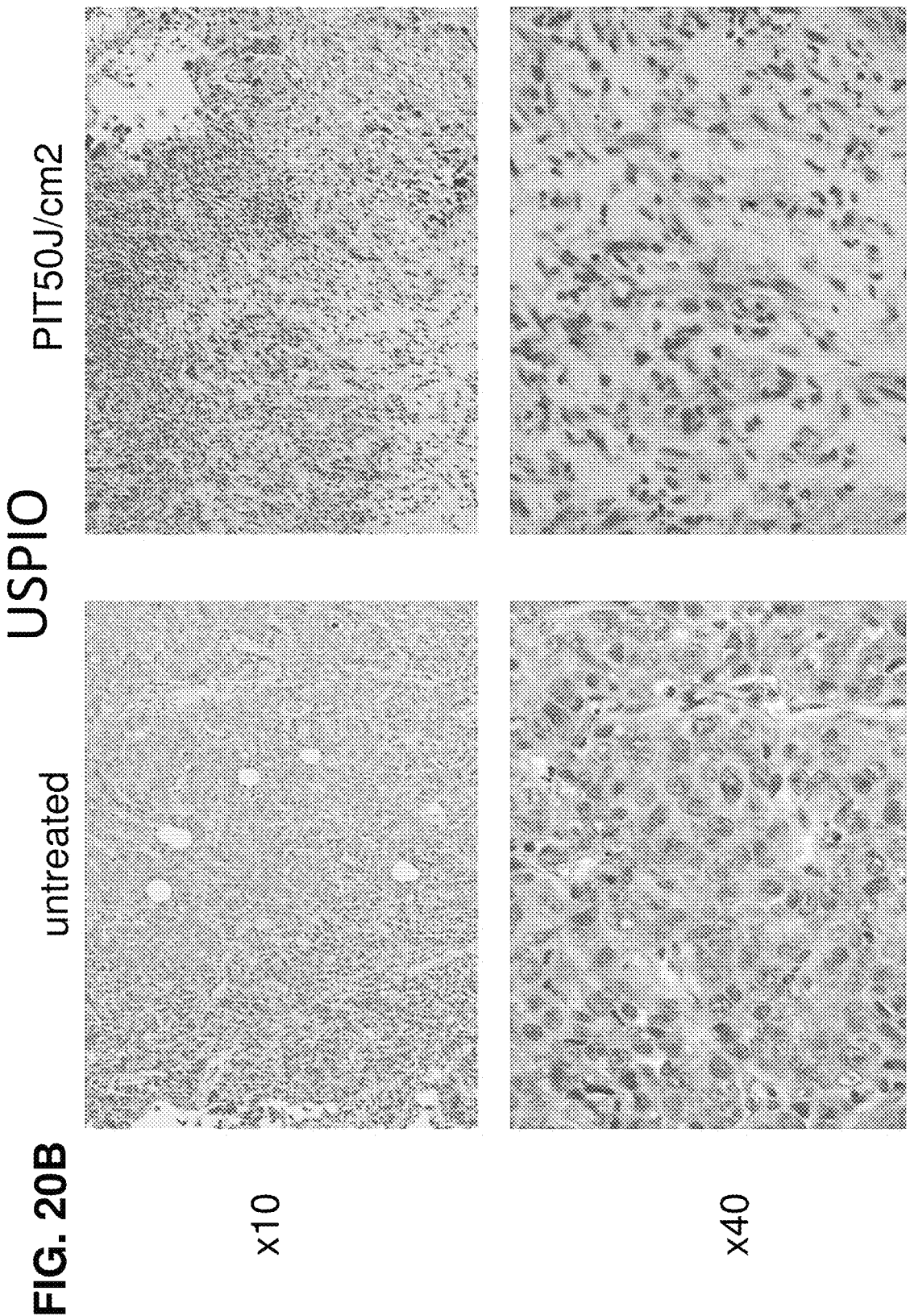

FIGS. 20A-20C. A. The dynamic images of USPIO after PIT. A431 mice were injected with Pan-IR700, and 24 h later, NIR light (50 J/cm2) were irradiated to the right side tumor. USPIO was administered 1 h after PIT treatment. Only the right sided tumor was clearly shown up within 5 min. B. Prucian blue staining and HE staining. C. The dynamic images of G6-Gd after PIT. A431 mice were injected with Pan-IR700, and 24 h later, NIR light (50 J/cm2) were irradiated to the right side tumor. G6-Gd was administered 1 h after PIT treatment. Only the right sided tumor was clearly shown up within 5 min.

Figure 21B:
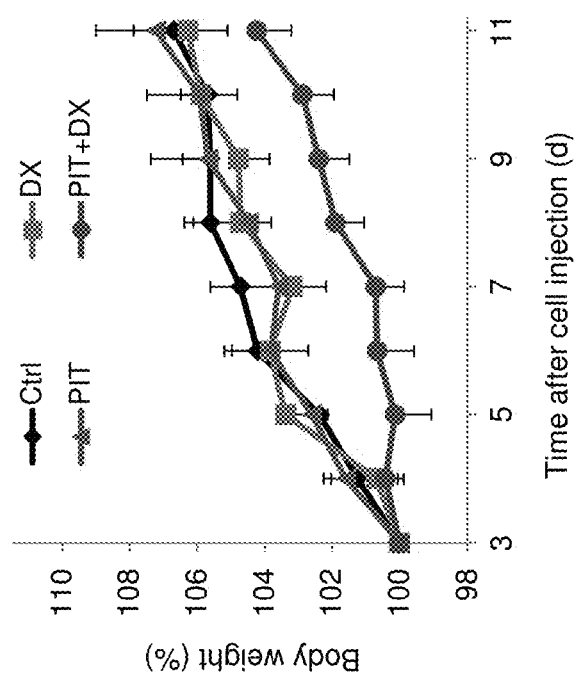
Figure 21A:
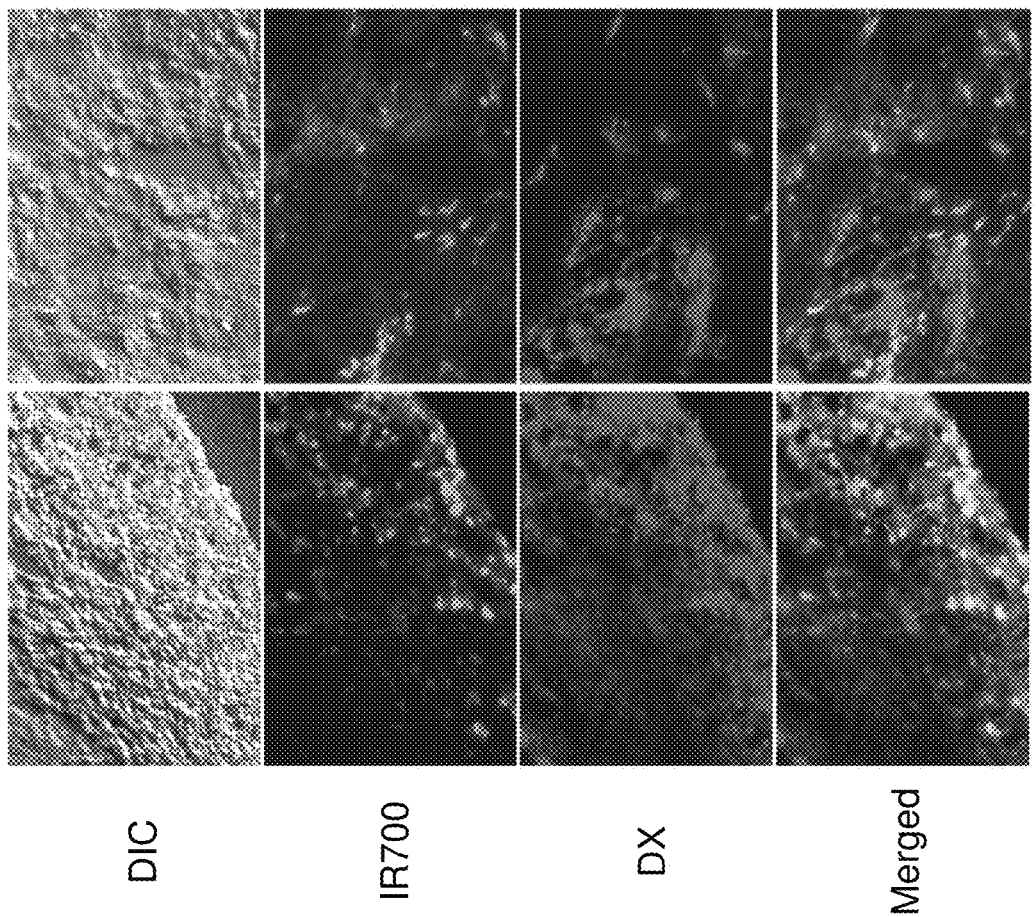

FIGS. 21A-21B. A. Fluorescence microscopic studies in the margin and core regions of tumors. IR700 signal shows the survived A431 cells. Daunorubicin containing liposome was broadly distributed in the PIT-treated tumor tissues and co-localization of IR700 and Daunorubicin containing liposome was partially observed. Especially in the core regions, DX can be taken up in the locally necrotic regions. B. The change of body weight after therapy. There was no obvious difference between groups.

DETAILED DESCRIPTION OF SEVERAL EMBODIMENTS

Unless otherwise explained, all technical and scientific terms used herein have the same meaning as commonly understood by one of ordinary skill in the art to which a disclosed invention belongs. The singular terms "a," "an," and "the" include plural referents unless context clearly indicates otherwise. Similarly, the word "or" is intended to include "and" unless the context clearly indicates otherwise. "Comprising" means "including." Hence "comprising A or B" means "including A" or "including B" or "including A and B."

Suitable methods and materials for the practice and/or testing of embodiments of the disclosure are described below. Such methods and materials are illustrative only and are not intended to be limiting. Other methods and materials similar or equivalent to those described herein can be used. For example, conventional methods well known in the art to which a disclosed invention pertains are described in various general and more specific references, including, for example, Sambrook et al., *Molecular Cloning: A Laboratory Manual*, 2d ed., Cold Spring Harbor Laboratory Press, 1989; Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2000); Ausubel et al., *Short Protocols in Molecular Biology: A Compendium of Methods from Current Protocols in Molecular Biology*, 4th ed., Wiley & Sons, 1999; Harlow and Lane, *Antibodies: A Laboratory Manual*, Cold Spring Harbor Laboratory Press, 1990; and *Harlow and Lane, Using Antibodies: A Laboratory Manual*, Cold Spring Harbor Laboratory Press, 1999.

The sequences associated with all GenBank Accession numbers referenced herein are incorporated by reference for the sequence available on Jul. 9, 2010.

In order to facilitate review of the various embodiments of the disclosure, the following explanations of specific terms are provided:

Administration: To provide or give a subject an agent, such as an antibody-IR700 molecule, by any effective route. Exemplary routes of administration include, but are not limited to, topical, injection (such as subcutaneous, intramuscular, intradermal, intraperitoneal, intratumoral, and intravenous), oral, ocular, sublingual, rectal, transdermal, intranasal, vaginal and inhalation routes.

Antibody: A polypeptide ligand comprising at least a light chain or heavy chain immunoglobulin variable region which specifically recognizes and binds an epitope of an antigen, such as a tumor-specific protein. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody.

Antibodies include intact immunoglobulins and the variants and portions of antibodies well known in the art, such as Fab fragments, Fab' fragments, F(ab)'$_2$ fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (for example, humanized murine antibodies), heteroconjugate antibodies (such as, bispecific antibodies). See also, *Pierce Catalog and Handbook,* 1994-1995 (Pierce Chemical Co., Rockford, Ill.); Kuby, J., *Immunology,* 3$^{rd}$ Ed., W. H. Freeman & Co., New York, 1997

Typically, a naturally occurring immunoglobulin has heavy (H) chains and light (L) chains interconnected by disulfide bonds. There are two types of light chain, lambda (λ) and kappa (κ). There are five main heavy chain classes (or isotypes) which determine the functional activity of an antibody molecule: IgM, IgD, IgG, IgA and IgE.

Each heavy and light chain contains a constant region and a variable region (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs." The extent of the framework region and CDRs have been defined (see, Kabat et al., *Sequences of Proteins of Immunological Interest*, U.S. Department of Health and Human Services, 1991, which is hereby incorporated by reference). The Kabat database is now maintained online. The sequences of the framework regions of different light or heavy chains are relatively conserved within a species, such as humans. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

A "monoclonal antibody" is an antibody produced by a single clone of B lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "chimeric antibody" has framework residues from one species, such as human, and CDRs (which generally confer antigen binding) from another species, such as a murine antibody that specifically binds mesothelin.

A "humanized" immunoglobulin is an immunoglobulin including a human framework region and one or more CDRs from a non-human (for example a mouse, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (see for example, U.S. Pat. No. 5,585,089).

A "human" antibody (also called a "fully human" antibody) is an antibody that includes human framework regions and all of the CDRs from a human immunoglobulin. In one example, the framework and the CDRs are from the same originating human heavy and/or light chain amino acid sequence. However, frameworks from one human antibody can be engineered to include CDRs from a different human antibody. All parts of a human immunoglobulin are substantially identical to corresponding parts of natural human immunoglobulin sequences.

"Specifically binds" refers to the ability of individual antibodies to specifically immunoreact with an antigen, such as a tumor-specific antigen, relative to binding to unrelated proteins, such as non-tumor proteins, for example β-actin. For example, a HER2-specific binding agent binds substantially only the HER-2 protein in vitro or in vivo. As used herein, the term "tumor-specific binding agent" includes tumor-specific antibodies and other agents that bind substantially only to a tumor-specific protein in that preparation.

The binding is a non-random binding reaction between an antibody molecule and an antigenic determinant of the T cell surface molecule. The desired binding specificity is typically determined from the reference point of the ability of the antibody to differentially bind the T cell surface molecule and an unrelated antigen, and therefore distinguish between two different antigens, particularly where the two antigens have unique epitopes. An antibody that specifically binds to a particular epitope is referred to as a "specific antibody".

In some examples, an antibody (such as an antibody-IR700 molecule) specifically binds to a target (such as a cell surface protein) with a binding constant that is at least $10^3$ $M^{-1}$ greater, $10^4$ $M^-$ greater or $10^5$ $M^{-1}$ greater than a binding constant for other molecules in a sample or subject. In some examples, an antibody (e.g., monoclonal antibody) or fragments thereof, has an equilibrium constant (Kd) of 1 nM or less. For example, an antibody binds to a target, such as tumor-specific protein with a binding affinity of at least about $0.1\times10^{-8}$ M, at least about $0.3\times10^{-8}$ M, at least about $0.5\times10^{-8}$ M, at least about $0.75\times10^{-8}$ M, at least about $1.0\times10$ M, at least about $1.3\times10^{-8}$ M at least about $1.5\times10^{-8}$ M, or at least about $2.0\times10$ M. Kd values can, for example, be determined by competitive ELISA (enzyme-linked immunosorbent assay) or using a surface-plasmon resonance device such as the Biacore T100, which is available from Biacore, Inc., Piscataway, N.J.

Antibody-IR700 molecule or antibody-IR700 conjugate: A molecule that includes both an antibody, such as a tumor-specific antibody, conjugated to IR700. In some examples the antibody is a humanized antibody (such as a humanized monoclonal antibody) that specifically binds to a surface protein on a cancer cell.

Antigen (Ag): A compound, composition, or substance that can stimulate the production of antibodies or a T cell response in an animal, including compositions (such as one that includes a tumor-specific protein) that are injected or absorbed into an animal. An antigen reacts with the products of specific humoral or cellular immunity, including those induced by heterologous antigens, such as the disclosed antigens. "Epitope" or "antigenic determinant" refers to the region of an antigen to which B and/or T cells respond. In one embodiment, T cells respond to the epitope, when the epitope is presented in conjunction with an MHC molecule. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or about 8-10 amino acids in a unique spatial conformation. Methods of determining spatial conformation of epitopes include, for example, x-ray crystallography and nuclear magnetic resonance.

Examples of antigens include, but are not limited to, peptides, lipids, polysaccharides, and nucleic acids containing antigenic determinants, such as those recognized by an immune cell. In some examples, an antigen includes a tumor-specific peptide (such as one found on the surface of a cancer cell) or immunogenic fragment thereof.

Cancer: A malignant tumor characterized by abnormal or uncontrolled cell growth. Other features often associated with cancer include metastasis, interference with the normal functioning of neighboring cells, release of cytokines or other secretory products at abnormal levels and suppression or aggravation of inflammatory or immunological response, invasion of surrounding or distant tissues or organs, such as lymph nodes, etc. "Metastatic disease" refers to cancer cells that have left the original tumor site and migrate to other parts of the body for example via the bloodstream or lymph system. In one example, the cell killed by the disclosed methods is a cancer cell.

Contacting: Placement in direct physical association, including both a solid and liquid form. Contacting can occur in vitro, for example, with isolated cells, such as tumor cells, or in vivo by administering to a subject (such as a subject with a tumor).

Decrease: To reduce the quality, amount, or strength of something. In one example, a therapeutic composition that includes one or more antibody-IR700 molecules decreases the viability of cells to which the antibody-IR700 molecule specifically binds, following irradiation of the cells with NIR (for example at a wavelength of about 680 nm) at a dose of at least 1 J cm$^{2-}$, for example as compared to the response in the absence of the antibody-IR700 molecule. In some examples such a decrease is evidenced by the killing of the cells. In some examples, the decrease in the viability of cells is at least 20%, at least 50%, at least 75%, or even at least 90%, relative to the viability observed with a composition that does not include an antibody-IR700 molecule. In other examples, decreases are expressed as a fold change, such as a decrease in the cell viability by at least 2-fold, at least 3-fold, at least 4-fold, at least 5-fold, at least 8-fold, at least 10-fold, or even at least 15 or 20-fold, relative to the viability observed with a composition that does not include an antibody-IR700 molecule. Such decreases can be measured using the methods disclosed herein.

IR700 (IRDye® 700DX): A dye having the following formula:

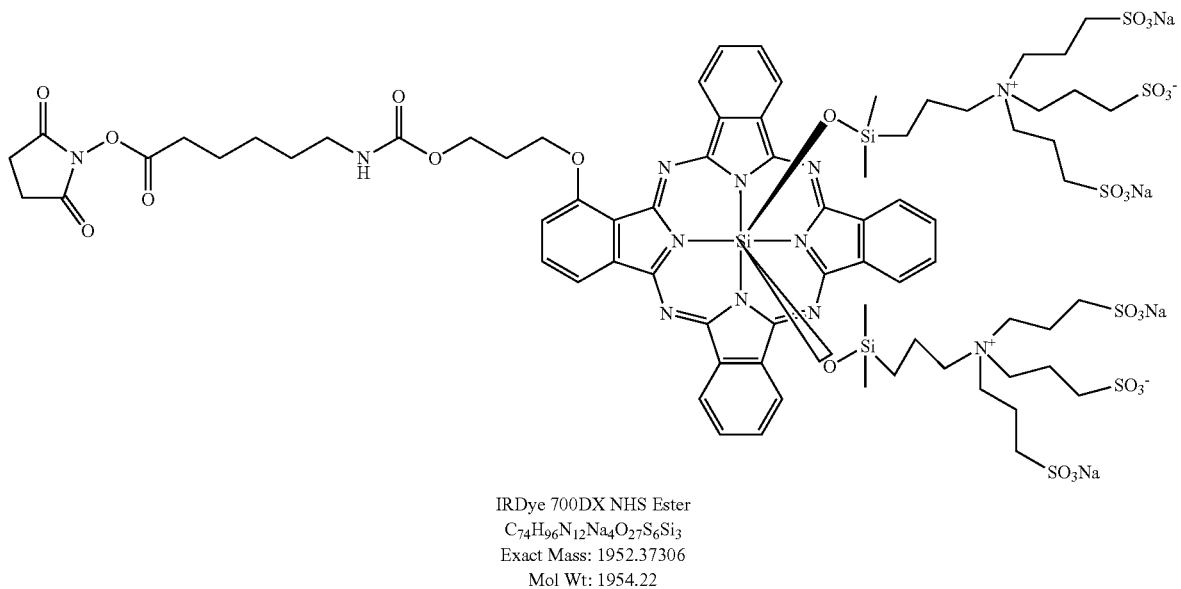

IRDye 700DX NHS Ester
$C_{74}H_{96}N_{12}Na_4O_{27}S_6Si_3$
Exact Mass: 1952.37306
Mol Wt: 1954.22

Currently commercially available from LI-COR (Lincoln, Nebr.). IR700 has several favorable chemical properties. Amino-reactive IR700 is a relatively hydrophilic dye and can be covalently conjugated with an antibody using the NHS ester of IR700. IR700 also has more than 5-fold higher extinction coefficient ($2.1 \times 10$ M$^{-1}$ cm$^{-1}$ at the absorption maximum of 689 nm), than conventional photosensitizers such as the hematoporphyrin derivative Photofrin® ($1.2 \times 10^3$ M$^{-1}$ cm$^{-1}$ at 630 nm), meta-tetrahydroxyphenylchlorin; Foscan® ($2.2 \times 10^4$ M$^{-1}$ cm$^{-1}$ at 652 nm), and mono-L-aspartylchlorin e6; NPe6/Laserphyrin® ($4.0 \times 10^4$ M$^{-1}$ cm$^{-1}$ at 654 nm).

Pharmaceutical composition: A chemical compound or composition capable of inducing a desired therapeutic or prophylactic effect when properly administered to a subject. A pharmaceutical composition can include a therapeutic agent, such as one or more antibody-IR700 molecules. A therapeutic or pharmaceutical agent is one that alone or together with an additional compound induces the desired response (such as inducing a therapeutic or prophylactic effect when administered to a subject). In a particular example, a pharmaceutical composition includes a therapeutically effective amount of at least one antibody-IR700 molecule.

Pharmaceutically acceptable vehicles: The pharmaceutically acceptable carriers (vehicles) useful in this disclosure are conventional. *Remington's Pharmaceutical Sciences*, by E. W. Martin, Mack Publishing Co., Easton, Pa., 19th Edition (1995), describes compositions and formulations suitable for pharmaceutical delivery of one or more therapeutic compounds, such as one or more antibody-IR700 molecules.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Photoimmunotherapy (PIT): A molecular targeted therapeutic that utilizes a target-specific photosensitizer based on a near infrared (NIR) phthalocyanine dye, IR700, conjugated to monoclonal antibodies (MAb) targeting cell surface receptors. In one example the cell surface receptor is one found specifically on cancer cells, such as HER1, HER2 or PSMA, and thus PIT can be used to kill such cells. Cell death of the cells occurs when the antibody-IR700 molecule binds to the cells and the cells are irradiated with NIR, while cells that do not express the cell surface receptor recognized by the antibody-IR700 molecule are not killed in significant numbers.

Subject or patient: A term that includes human and non-human mammals. In one example, the subject is a human or veterinary subject, such as a mouse. In some examples, the subject is a mammal (such as a human) who has cancer, or is being treated for cancer.

Therapeutically effective amount: An amount of a composition that alone, or together with an additional therapeutic agent(s) (such as a chemotherapeutic agent) sufficient to achieve a desired effect in a subject, or in a cell, being treated with the agent. The effective amount of the agent (such as an antibody-IR700 molecule) can be dependent on several factors, including, but not limited to the subject or cells being treated, the particular therapeutic agent, and the manner of administration of the therapeutic composition. In one example, a therapeutically effective amount or concentration is one that is sufficient to prevent advancement (such as metastasis), delay progression, or to cause regression of a disease, or which is capable of reducing symptoms caused by the disease, such as cancer. In one example, a therapeutically effective amount or concentration is one that is sufficient to increase the survival time of a patient with a tumor.

In one example, a desired response is to reduce or inhibit one or more symptoms associated with cancer. The one or more symptoms do not have to be completely eliminated for the composition to be effective. For example, administration of a composition containing an antibody-IR700 molecule followed by irradiation can decrease the size of a tumor (such as the volume or weight of a tumor, or metastasis of a tumor), for example by at least 20%, at least 50%, at least 80%, at least 90%, at least 95%, at least 98%, or even at least 100%, as compared to the tumor size in the absence of the antibody-IR700 molecule. In one particular example, a desired response is to kill a population of cells by a desired amount, for example by killing at least 20%, at least 50%, at least 60%, at least 70%, at least 80%, at least 90%, at least 95%, at least 98%, or even at least 100% of the cells, as compared to the cell killing in the absence of the antibody-IR700 molecule and irradiation. In one particular example, a desired response is to increase the survival time of a patient with a tumor (or who has had a tumor recently removed) by a desired amount, for example increase survival by at least 20%, at least 50%, at least 60%, at least 70%, at least 80%, at least 90%, at least 95%, at least 98%, or even at least 100%, as compared to the survival time in the absence of the antibody-IR700 molecule and irradiation.

The effective amount of an agent that includes one of the disclosed antibody-IR700 molecules, that is administered to a human or veterinary subject will vary depending upon a number of factors associated with that subject, for example the overall health of the subject. An effective amount of an agent can be determined by varying the dosage of the product and measuring the resulting therapeutic response, such as the regression of a tumor. Effective amounts also can be determined through various in vitro, in vivo or in situ immunoassays. The disclosed agents can be administered in a single dose, or in several doses, as needed to obtain the desired response. However, the effective amount of an agent can be dependent on the source applied, the subject being treated, the severity and type of the condition being treated, and the manner of administration.

In particular examples, a therapeutically effective dose of an antibody-IR700 molecule is at least 0.5 milligram per 60 kilogram (mg/kg), at least 5 mg/60 kg, at least 10 mg/60 kg, at least 20 mg/60 kg, at least 30 mg/60 kg, at least 50 mg/60 kg, for example 0.5 to 50 mg/60 kg, such as a dose of 1 mg/60 kg, 2 mg/60 kg, 5 mg/60 kg, 20 mg/60 kg, or 50 mg/60 kg, for example when administered iv. In another example, a therapeutically effective dose of an antibody-IR700 molecule is at least 10 µg/kg, such as at least 100 µg/kg, at least 500 µg/kg, or at least 500 µg/kg, for example 10 µg/kg to 1000 µg/kg, such as a dose of 100 µg/kg, 250 µg/kg, about 500 µg/kg, 750 µg/kg, or 1000 µg/kg, for example when administered intratumorally or ip. In one example, a therapeutically effective dose is at least 1 µg/ml, such as at least 500 µg/ml, such as between 20 µg/ml to 100 µg/ml, such as 10 µg/ml, 20 µg/ml, 30 µg/ml, 40 µg/ml, 50 µg/ml, 60 µg/ml, 70 µg/ml, 80 µg/ml, 90 µg/ml or 100 µg/ml administered in topical solution. However, one skilled in the art will recognize that higher or lower dosages also could be used, for example depending on the particular antibody-IR700 molecule. In particular examples, such daily dosages are administered in one or more divided doses (such as 2, 3, or 4 doses) or in a single formulation. The disclosed antibody-IR700 molecules can be administered alone, in the presence of a pharmaceutically acceptable carrier, in the presence of other therapeutic agents (such as other antineoplastic agents).

Generally a suitable dose of irradiation following administration of the antibody-IR700 is at least 1 J cm$^{-2}$ at a wavelength of 660-740 nm, for example, at least 10 J cm$^{-2}$ at a wavelength of 660-740 nm, at least 50 J cm$^{-2}$ at a wavelength of 660-740 nm, or at least 100 J cm$^{-2}$ at a wavelength of 660-740 nm, for example 1 to 500 J cm$^{-2}$ at a wavelength of 660-740 nm. In some examples the wavelength is 660-710 nm. In specific examples, a suitable dose of irradiation following administration of the antibody-IR700 molecule is at least 1.0 J cm$^{-2}$ at a wavelength of 680 nm for example, at least 10 J cm$^{-2}$ at a wavelength of 680 nm, at least 50 J cm$^{-2}$ at a wavelength of 680 nm, or at least 100 J cm$^{-2}$ at a wavelength of 680 nm, for example 1 to 500 1.0 J cm$^{-2}$ at a wavelength of 680 nm. In particular examples, multiple irradiations are performed (such as at least 2, at least 3, or at least 4 irradiations, such as 2, 3, 4, 5, 6, 7, 8, 9 or 10 separate administrations), following administration of the antibody-IR700 molecule.

Treating: A term when used to refer to the treatment of a cell or tissue with a therapeutic agent, includes contacting or incubating an agent (such as an antibody-IR700 molecule) with the cell or tissue. A treated cell is a cell that has been contacted with a desired composition in an amount and under conditions sufficient for the desired response. In one example, a treated cell is a cell that has been exposed to an antibody-IR700 molecule under conditions sufficient for the antibody to bind to a surface protein on the cell, followed by irradiation, until sufficient cell killing is achieved.

Tumor, neoplasia, malignancy or cancer: A neoplasm is an abnormal growth of tissue or cells which results from excessive cell division. Neoplastic growth can produce a tumor. The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant." A "non-cancerous tissue" is a tissue from the same organ wherein the malignant neoplasm formed, but does not have the characteristic pathology of the neoplasm. Generally, noncancerous tissue appears histologically normal. A "normal tissue" is tissue from an organ, wherein the organ is not affected by cancer or another disease or disorder of that organ. A "cancer-free" subject has not been diagnosed with a cancer of that organ and does not have detectable cancer.

Exemplary tumors, such as cancers, that can be treated with the claimed methods include solid tumors, such as breast carcinomas (e.g. lobular and duct carcinomas), sarcomas, carcinomas of the lung (e.g., non-small cell carcinoma, large cell carcinoma, squamous carcinoma, and adenocarcinoma), mesothelioma of the lung, colorectal adenocarcinoma, stomach carcinoma, prostatic adenocarcinoma, ovarian carcinoma (such as serous cystadenocarcinoma and mucinous cystadenocarcinoma), ovarian germ cell tumors, testicular carcinomas and germ cell tumors, pancreatic adenocarcinoma, biliary adenocarcinoma, hepatocellular carcinoma, bladder carcinoma (including, for instance, transitional cell carcinoma, adenocarcinoma, and squamous carcinoma), renal cell adenocarcinoma, endometrial carcinomas (including, e.g., adenocarcinomas and mixed Mullerian tumors (carcinosarcomas)), carcinomas of the endocervix, ectocervix, and vagina (such as adenocarcinoma and squamous carcinoma of each of same), tumors of the skin (e.g., squamous cell carcinoma, basal cell carcinoma, malignant melanoma, skin appendage tumors, Kaposi sarcoma, cutaneous lymphoma, skin adnexal tumors and various types of sarcomas and Merkel cell carcinoma), esophageal carcinoma, carcinomas of the nasopharynx and oropharynx (including squamous carcinoma and adenocarcinomas of same), salivary gland carcinomas, brain and central nervous system tumors (including, for example, tumors of glial, neuronal, and meningeal origin), tumors of peripheral nerve, soft tissue sarcomas and sarcomas of bone and cartilage, and lymphatic tumors (including B-cell and T-cell malignant lymphoma). In one example, the tumor is an adenocarcinoma.

The methods can also be used to treat liquid tumors, such as a lymphatic, white blood cell, or other type of leukemia. In a specific example, the tumor treated is a tumor of the blood, such as a leukemia (for example acute lymphoblastic leukemia (ALL), chronic lymphocytic leukemia (CLL), acute myelogenous leukemia (AML), chronic myelogenous leukemia (CML), hairy cell leukemia (HCL), T-cell prolymphocytic leukemia (T-PLL), large granular lymphocytic leukemia, and adult T-cell leukemia), lymphomas (such as Hodgkin's lymphoma and non-Hodgkin's lymphoma), and myelomas).

Under conditions sufficient for: A phrase that is used to describe any environment that permits the desired activity. In one example, "under conditions sufficient for" includes administering an antibody-IR700 molecule to a subject sufficient to allow the antibody-IR700 molecule to bind to cell surface proteins. In particular examples, the desired activity is killing the cells to which the antibody-IR700 molecule is bound, following therapeutic irradiation of the cells.

Untreated cell: A cell that has not been contacted with a desired agent, such as an antibody-IR700 molecule. In an example, an untreated cell is a cell that receives the vehicle in which the desired agent was delivered.

Disclosure of certain specific examples is not meant to exclude other embodiments. In addition, any treatments described herein are not necessarily exclusive of other treatment, but can be combined with other bioactive agents or treatment modalities.

Overview of Technology

Conventional photodynamic therapy (PDT) for cancer therapy is based on the preferential accumulation of a photosensitizer in tumor to produce phototoxicity with minimal damage to surrounding tissue (Dougherty et al. *J Natl Cancer Inst* 90:889-905, 1998). Traditionally, PDT is thought to be mediated by the generation of ROS, especially singlet oxygen, in the presence of oxygen (Dougherty et al. *J Natl Cancer Inst* 90:889-905, 1998). However, to the extent that existing photosensitizers lack tumor selectivity, considerable damage can be seen in normal tissues leading to dose limiting toxicity. Thus, current methods of PDT would be improved if more selective targeting of the photosensitizer and more efficient phototoxicity per photon absorbed was possible.

Disclosed herein are highly targeted photosensitizers, referred to as antibody-IR700 molecules. The photosensitizer, IR700, is excited in the NIR range leading to deeper tissue penetration resulting in successful eradication of subcutaneously xenografted tumors after only a single dose of external NIR light irradiation. Targeted phototoxicity appears to be primarily dependent on binding of the antibody-1R700 molecules to the cell membrane and to a lesser extent on internalization and ROS formation. The fluorescence induced by the conjugate can be used to non-invasively guide both PIT and monitor the results of therapy.

Although a targeted photosensitizer can distribute throughout the body, it is only active where intense light is applied, reducing the likelihood of off-target effects. In contrast, existing photosensitizers are poorly selective small molecules which bind not only to cancer cells but also to normal cells, including the skin and other epithelial surfaces, resulting in unwanted phototoxicity. In addition, target specific delivery of conventional photosensitizers is theoretically difficult because, after reaching the cell, the agent must still be internalized into organelles, such as mitochondria, to be most effective. Various combinations of conventional photosensitizers and MAbs have been tested to improve selectivity (Mew et al., *J Immunol* 130:1473-1477, 1983; Sobolev et al., *Prog Biophys Mol Biol* 73:51-90, 2000; Carcenac et al., *Br J Cancer* 85:1787-93, 2001; Vrouenraets et al., *Cancer Res* 59:1505-13, 1999; Vrouenraets et al., *Cancer Res* 61:1970-1975, 2001; Hamblin et al., *Cancer Res* 56:5205-10, 1996; Mew et al., *Cancer Res* 45:4380-6, 1985). However, these have had limited success especially when measured by in vivo therapeutic effects, for example because conventional photosensitizers have low extinction coefficients that require conjugation of large numbers of photosensitizers to a single antibody molecule thus, potentially decreasing binding affinity, because conventional photosensitizers are mostly hydrophobic leading to difficulties in conjugating photosensitizers to antibodies without compromising the immunoreactivity and in vivo target accumulation, and because conventional photosensitizers generally absorb light in the visible range reducing tissue penetration.

It is shown herein that antibody-based photosensitizers (such as mAb-based photosensitizers), which are activated by NIR light for targeted photoimmunotherapy (PIT) only when bound to the target molecule on the cancer cellular membrane. The fluorophore IR700 (Licor Co. Lincoln, Nebr.) can become a photosensitizer when conjugated to an antibody specific for a cell surface receptor and can thus be used for target specific photodynamic therapy of undesired cells, such as tumor or cancer cells. Further, because these agents also emit a diagnostic fluorescence, they can be used to direct the application of light to minimize light exposure to non-relevant tissues and non-invasively monitor therapeutic effects. Based on the similarity of the phototoxicity induced with three different MAbs against several different cells expressing various numbers of respective target molecules and considering the potentially additive benefits from immunotherapy this method can be generally applicable to other mAbs (such as those disclosed in Nanus et al., *J. Urology* 170:S84-S88, 2003 and van Dongen et al., *Adv Drug Deliv Rev* 56:31-52, 2004).

When IR700 was conjugated with an anti-EGFR antibody (HER1 or HER2) or a PSMA antibody, cells that selectively bound the conjugate were killed upon exposure to 680 nm near-infrared (NIR) light. Based on this novel observation patient therapies are provided. Since this antibody-dependent target-cell specific photodynamic therapy is achieved with NIR light (e.g., 680 nm) excitation and showed highly selectively cytotoxic effects only upon antibody binding, this new antibody-dependent target-cell specific photodynamic therapy using IR700 can be used in cancer patients as a way to personalize cancer therapy with minimal side effects.

The selectivity of the antibody-IR700 conjugate is derived from its activation after binding to the cell membrane of target cells; unbound conjugate does not contribute to phototoxicity. Short term viability assays, as well as long term proliferation assays, demonstrated that the conjugate was capable of inducing specific cell death. When co-cultures of receptor-positive and -negative cells were treated, only the receptor-positive cells were killed despite the presence of unbound antibody—1R700 in the culture medium. This selective cell killing minimizes damage to normal cells.

The antibody-1R700 molecule must be bound to the cellular membrane to be active. For instance, the rupture of endolysosome occurred within a second of light exposure. Cell death induced by singlet oxygen generally induces a slower apoptotic cell death. Since cell membrane damage was so quickly induced even at 4° C. by this method, it is hypothesized that cell death is caused by the rapid expansion of locally heated water with relatively minor effects due to singlet oxygen effects.

Treatment with sodium azide, a redox and singlet oxygen scavenger, only partially reduced the phototoxicity but did not totally eliminate the effectiveness of the conjugate. This indicates that ROS generation is a minor part of the phototoxic effect. The observation that phototoxicity was induced after incubation with antibody-1R700 after only 1 hour at 4° C. indicates that internalization of the conjugate is not required for activity. This differs from current PDT agents that require intracellular localization to be effective. Video microscopy demonstrated rapid visible damage to the membrane and lysosomes after exposure to light, following incubation for more than 6 hours at 37° C., when the antibody-conjugate was internalized.

The disclosed antibody-1R700 conjugates permitted detection of targeted tissue. This can permit specific lesions to be identified with PIT rather than irradiating the entire field. Doses required for diagnosis (50 µg) were significantly lower than those required for therapy (300 µg). Improved intratumoral distribution of antibody occurred with the therapeutic dose. Because both bound and unbound agent fluoresces, there is relatively high background signal at therapeutic doses. Nevertheless, after PIT, the fluorescence of the treated tumors decreased and eventually disappeared, providing a means of monitoring the treatment Free IR700 and catabolized IR700, are readily excreted into urine within 1 hour without accumulation in any specific organ. The other component of PIT, light irradiation with NIR (e.g., at 690 nm) is unlikely to be toxic except at thermal doses. There should be no limitations on the cumulative irradiation dose of NIR light, unlike ionizing radiation such as x-ray or gamma-ray (FIG. 9). Therefore, repeated PIT can be used for long term management of cancer patients. It was observed that repeated PIT with 3 different regimens (3 or 4 fractionated NIR irradiations at a single dose of antibody-IR700 conjugate and 4 cycles of PIT every 2 weeks after multiple doses of antibody) controlled tumor regrowth, resulting in tumor free survival of more than 4 months.

It is also shown herein that use of antibody-1R700 conjugates with PIT enhances delivery of nano-sized agents to the tumor, for example for about 8 hours following PIT. Nano-sized agents can target vascular endothelial cells by activating with humeral factor including depletion of vascular endothelial growth factor (VEGF) or damaging cells using vascular toxic agents. Based on these observations, methods are provided for enhancing delivery of other anti-neoplastic therapies to the tumor following PIT. In one example, delivery of the anti-neoplastic therapy to the tumor (or effectiveness of the anti-neoplastic therapy) is increased by at least 20/%, at least 25%, at least 30%, at least 40%, at least 50%, at least 75%, at least 80%, at least 90%, or even at least 95%, for example as compared to delivery of the anti-neoplastic therapy to the tumor (or effectiveness of the anti-neoplastic therapy) in the absence of administration of the antibody-1R700 conjugates and PIT.

Methods for Killing Cells and Treating Tumors

The present disclosure provides methods for killing a cell, such as a target cell. The cell expresses a protein on its surface, such as a tumor specific antigen, that can specifically bind to an antibody that is conjugated to the dye IR700 (referred to herein as an antibody-IR700 molecule). The cell is contacted with a therapeutically effective amount of one or more antibody-IR700 molecules (for example in the presence of a pharmaceutically acceptable carrier, such as a pharmaceutically and physiologically acceptable fluid), under conditions that permit the antibody to specifically bind to the cell surface protein. For example, the antibody-IR700 molecule can be present in a pharmaceutically effective carrier, such as water, physiological saline, balanced salt solutions (such as PBS/EDTA), aqueous dextrose, sesame oil, glycerol, ethanol, combinations thereof, or the like, as a vehicle. The carrier and composition can be sterile, and the formulation suits the mode of administration.

After contacting or administering the one or more antibody-IR700 molecules under conditions that allow the one or more antibody-IR700 molecules to bind to their target on a cell surface, the cell is then irradiated under conditions that permit killing of the cells, for example irradiation at a wavelength of 660 to 710 nm at a dose of at least 1 J cm$^{-2}$. In one example, there is at least 10 minutes, at least 30 minutes, at least 1 hour, at least 4 hours, at least 8 hours, at least 12 hours, or at least 24 hours (such as 1 to 4 hours, 30 minutes to 1 hour, 10 minutes to 60 minutes, or 30 minutes to 8 hours) in between contacting the cell with the antibody-IR700 molecules and the irradiation. The NIR excitation light wavelength allows penetration of at least several centimeters into tissues. For example, by using fiber-coupled laser diodes with diffuser tips, NIR light can be delivered within several centimeters of otherwise inaccessible tumors located deep to the body surface. In addition to treating solid cancers, circulating tumor cells can be targeted since they can be excited when they traverse superficial vessels (for example using the NIR LED wearable devices disclosed herein). The disclosed methods can also be used as a therapy for transplant rejection.

The method also includes contacting the cell with one or more additional therapeutic agents. The inventors have determined that there is about an 8 hour window following irradiation (for example irradiation at a wavelength of 660 to 710 nm at a dose of at least 10 J cm$^{-2}$, at least 20 J cm$^{-2}$, at least 30 J cm$^{-2}$, at least 40 J cm$^{-2}$, at least 50 J cm$^{-2}$, at least 70 J cm$^{-2}$, at least 80 J cm$^{-2}$ or at least 100 J cm$^{-2}$, such as at least 10 to 100 J cm$^{-2}$), during which uptake of additional agents (e.g., nano-sized agents, such as those about at least 1 nm in diameter, at least 10 nm in diameter, at least 100 nm in diameter, or at least 200 nm in diameter, such as 1 to 500 nm in diameter) by the PIT-treated cells is unexpectedly and superiorly enhanced. Thus, one or more additional therapeutic agents can be contacted with the cell contemporaneously or sequentially with the PIT. In one example, the additional therapeutic agents are administered after the irradiation, for example, about 0 to 8 hours after irradiating the cell (such as at least 10 minutes, at least 30 minutes, at least 60 minutes, at least 2 hours, at least 3 hours, at least 4, hours, at least 5 hours, at least 6 hours, or at least 7 hours after the irradiation, for example no more than 10 hours, no more than 9 hours, or no more than 8 hours, such as 1 hour to 10 hours, 1 hour to 9 hours 1 hour to 8 hours, 2 hours to 8 hours, or 4 hours to 8 hours after irradiation). In another example, the additional therapeutic agents are administered just before the irradiation (such as about 10 minutes to 120 minutes before irradiation, such as 10 minutes to 60 minutes or 10 minutes to 30 minutes before irradiation).

In some examples, combining the antibody-IR700 molecules/PIT with the additional therapy (such as anti-neoplastic agents), enhances the effectiveness of the treatment of the tumor. For example, combining the antibody-IR700 molecules/PIT with the additional therapy (such as anti-neoplastic agents) can result in a tumor volume that is less than the tumor volume would be if it were treated with either the antibody-IR700 molecules/PIT alone or the additional therapy alone, that is, there is a synergistic effect. In one example, the volume of a tumor treated with the combination therapy is at least 2-fold, at least 3-fold, at least 4-fold, or even at least 5-fold smaller than the volume of a tumor treated with either the antibody-IR700 molecules/PIT alone or the additional therapy alone (for example after at least 7 days, at least 10 days, at least 14 days, at least 30 days, at least 60 days, at least 90 days, or at least 120 days after the treatment). In one example, the volume of a tumor treated with the combination therapy is at least 5-fold, at least 6-fold, at least 7-fold, or even at least 10-fold smaller than the volume of a control untreated tumor (for example after at least 7 days, at least 10 days, at least 14 days, at least 30 days, at least 60 days, at least 90 days, or at least 120 days after the treatment). In another or additional example, combining the antibody-IR700 molecules/PIT with the additional therapy (such as anti-neoplastic agents) can increase the survival time of a subject having a tumor relative to the survival time of the subject if the tumor was treated with either the antibody-IR700 molecules/PIT alone or the additional therapy alone, that is, there is a synergistic effect. In one example, the survival time of a subject having a tumor treated with the combination therapy is at least 2-fold, at least 3-fold, at least 4-fold, at least 5-fold, at least 6-fold, at least 7-fold, or at least 10-fold longer than survival time of a subject having a tumor treated with either the antibody-IR700 molecules/PIT alone or the additional therapy alone (for example after a specified period of time, such as at least 14 days, at least 30 days, at least 60 days, at least 90 days, at least 120 days, at least 6 months, at least 12 months, at least 24 months, or at least 5 years after the treatment, more subjects treated with the combination therapy will be alive than if treated with either therapy alone). In one example, the survival time of a subject having a tumor treated with the combination therapy is at least 5-fold, at least 10-fold, at least 15-fold, or even at least 20-fold greater than the survival time of a subject having an untreated tumor (for example after at least 7 days, at least 10 days, at least 14 days, at least 30 days, at least 60 days, at least 90 days, at least 120 days after the treatment at least 6 months, at least 12 months, at least 24 months, or at least 5 years after the treatment, more subjects treated with the combination therapy will be alive than if untreated).

Exemplary additional therapeutic agents include antineoplastic agents, such as chemotherapeutic and anti-angiogenic agents or therapies, such as radiation therapy. In one example the agent is a chemotherapy immunosuppressant (such as Rituximab, steroids) or a cytokine (such as GM-CSF). Chemotherapeutic agents are known in the art (see for example, Slapak and Kufe, Principles of Cancer Therapy, Chapter 86 in Harrison's Principles of Internal Medicine, 14th edition; Perry et al., Chemotherapy, Ch. 17 in Abeloff, Clinical Oncology 2nd ed., 2000 Churchill Livingstone, Inc; Baltzer and Berkery. (eds): Oncology Pocket Guide to Chemotherapy, 2nd ed. St. Louis, Mosby-Year Book, 1995; Fischer Knobf, and Durivage (eds): The Cancer Chemotherapy Handbook, 4th ed. St. Louis, Mosby-Year Book, 1993). Exemplary chemotherapeutic agents that can be used with the methods provided herein include but are not limited to, carboplatin, cisplatin, paclitaxel, docetaxel, doxorubicin, epirubicin, topotecan, irinotecan, gemcitabine, iazofurine, gemcitabine, etoposide, vinorelbine, tamoxifen, valspodar, cyclophosphamide, methotrexate, fluorouracil, mitoxantrone, Doxil (liposome encapculated doxiorubicine) and vinorelbine. In some examples, the additional therapeutic agent is conjugated to (or otherwise associated with) a nanoparticle, such as one at least 1 nm in diameter (for example at least 10 nm in diameter, at least 30 nm in diameter, at least 100 nm in diameter, at least 200 nm in diameter, at least 300 nm in diameter, at least 500 nm in diameter, or at least 750 nm in diameter, such as 1 nm to 500 nm, 1 nm to 300 nm, 1 nm to 100 nm, 10 nm to 500 nm, or 10 nm to 300 nm in diameter).

The methods can be used to kill cells in vitro, for example by incubating the cells with the antibody-IR700 molecules and one or more therapeutic agents in culture, or in vivo, for example, by administering one or more antibody-IR700 molecules and one or more therapeutic agents to the subject. For example, a subject to be treated can be administered a therapeutically effective amount of one or more antibody-IR700 molecules, followed by irradiating the subject (or a tumor or tumor cell in the subject) with a therapeutic dose of irradiation and administration of one or more additional therapeutic agents (such as within about 8 hours of the irradiation).

In one example, contacting target cells with one or more antibody-IR700 molecules followed by irradiation and administration of an additional therapeutic agent kills the target cells that express a cell surface protein that specifically binds to the antibody. For example, the disclosed methods can kill at least 10%, for example at least 20%, at least 40%, at least 50%, at least 80%, at least 90%, or more of the treated cells relative to the absence of treatment with one or more antibody-IR700 molecules followed by irradiation and administration of one or more therapeutic agents.

In one example, administration of one or more antibody-IR700 molecules to a subject having a tumor, in combination with irradiation and administration of one or more therapeutic agents, kills the cells that express a cell surface protein that can specifically bind to the antibody, thereby treating the tumor. For example, the disclosed methods can decrease the size or volume of a tumor, slow the growth of a tumor, decrease or slow metastasis of the tumor (for example by reducing the number of metastases or decreasing the volume or size of a metastasis), or combinations thereof. For example, the disclosed methods can reduce tumor cell size or volume and/or a metastatic tumor cell volume (or number of metastatic tumors), such as by at least 10%, for example by at least 20%, at least 40%, at least 50%, at least 80%, at least 90%, or more, relative to the absence of administration of one or more antibody-IR700 molecules followed by irradiation. In addition, the disclosed methods can result in a decrease in the symptoms associated with a tumor and/or a metastatic tumor. In one example, administration of the disclosed compositions slows the growth of a tumor, such as by at least 10%, for example by at least 20%, at least 40%, at least 50%, at least 80%, at least 90%, or more, relative to the absence of administration of the antibody-IR700 molecules followed by irradiation. Methods of monitoring tumor volume/size/metastasis are routine in the art. In some examples, the disclosed methods can increase a subject's (such as a subject with a tumor or who has had a tumor previously removed) survival time, for example relative the absence of administration of one or more antibody-IR700 molecules, irradiation, and administration of one or more therapeutic agents, such as an increase of at least 20%, at least 40%, at least 50%, at least 80%, at least 90%, or more. For example, the disclosed methods can increase a subject's survival time by at least 3 months, at least 6 months, at least 12 months, at least 18 months, at least 24 months, at least 36 months or more, relative to average survival time in the absence of administration of an anti-body-IR700 molecule, irradiation, and administration of one or more therapeutic agents.

Administration of therapeutically effective amounts of antibody-IR700 molecules followed by therapeutically effective doses of irradiation and administration of one or more therapeutic agents are capable of selectively killing tumor cells in vivo, and are capable of decreasing the weight or volume of a tumor in vivo. By selective killing of tumor cells relative to normal cells is meant that the methods are capable of killing tumor cells more effectively than normal cells such as, for example, cells not expressing the cell surface protein that specifically binds to the antibody administered.

The disclosed methods can be used to treat fixed tumors in the body as well as tumors in the circulation (e.g., leukemia cells, metastases, circulating tumor cells). However, circulating cells, by their nature, cannot be exposed to light for very long. Thus, if the cell to be killed is one that is circulating throughout the body, the methods can be accomplished by using a device that can be worn, or that covers parts of the body. For example, such a device can be worn for extended time periods. Everyday wearable items (e.g., wristwatches, jewelry (such as a necklace or bracelet), blankets, clothing (e.g., underwear, socks, and shoe inserts) and other everyday wearable items) which incorporate NIR emitting light emitting diodes (LEDs) and a battery pack, can be used. Such devices produce light on the skin underlying the device over long periods leading to continual exposure of light to superficial vessels over prolonged periods. Circulating tumor cells are exposed to the light as they transit thru the area underlying the device. As an example, a wristwatch or bracelet version of this device can include a series of NIR LEDs with battery power pack to be worn for most of the day.

After administration of the one or more antibody-IR700 molecules (e.g., intravenously), circulating cells bind the antibody-IR700 conjugate and become susceptible to killing by PIT. As these cells flow within the vessels adjacent to the LED present in the everyday wearable item (e.g., bracelet or wristwatch), they would be exposed to NIR light rendering them susceptible to cell killing. The dose of light may be adjustable according to diagnosis and cell type.

In some examples, the method further includes monitoring the therapy, such as killing of tumor cells. In such examples, the antibody-IR700 conjugate is contacted with the cells and the cells irradiated as described above. However, a lower dose of the antibody-IR700 conjugate and NIR light can be used (as cell killing may not be required, just monitoring of the therapy). In one example, the amount of antibody-IR700 conjugate administered for monitoring is at least 2-fold less (such as at least 3-, 4-, 5-, 6-, 7-, 8-, 9-, or 10-fold less than the therapeutic dose). In one example, the amount of antibody-IR700 conjugate administered for monitoring is at least 20% or at least 25% less than the therapeutic dose. In one example, the amount of NIR light used for monitoring is at least $1/1000$ or at least $1/10,000$ of the therapeutic dose. This permits detection of the cells being treated. For example, by using such methods, the size of the tumor and metastases can be monitored.

In some examples, the method is useful during surgery, such as endoscopic procedures. For example, after the antibody-IR700 conjugate is contacted with the cells and the cells irradiated as described above, this not only results in cell killing, but permits a surgeon or other medical care provider to visualize the margins of a tumor, and help ensure that resection of the tumor (such as a tumor of the skin, breast, lung, colon, or prostate) is complete and that the margins are clear. In some examples, a lower dose of the antibody-IR700 conjugate can be used for visualization, such as at least 2-fold less (such as at least 3-, 4-, 5-, 6-, 7-, 8-, 9-, or 10-fold less than the therapeutic dose).

Methods are provided that permit detection or monitoring of cell killing in real-time. Such methods are useful for example, to ensure sufficient amounts of antibody-IR700 molecules and/or one or more therapeutic agents, or sufficient amounts of irradiation, were delivered to the cell or tumor promote cell killing. These methods permit detection of cell killing before morphological changes become evident. In one example, the methods include contacting a cell having a cell surface protein with a therapeutically effective amount of one or more antibody-IR700 molecules (such as at least 0.01 nM, at least 0.1 nM, at least 1 nM, or at least 10 nM, such as 0.1 to 2 nM, 0.5 to 1.5 nM, such as 1 nM of the of one or more antibody-IR700 molecules), wherein the antibody specifically binds to the cell surface protein; irradiating the cell at a wavelength of 660 to 740 nm and at a dose of at least 20 J cm$^{-2}$; and detecting the cell with fluorescence lifetime imaging about 0 to 48 hours after irradiating the cell (such as at least 1 hour, at least 2 hours, at least 4 hours, at least 6 hours, at least 12 hours, at least 18 hours, at least 24 hours, at least 36 hours, at least 48 hours, or at least 72 hours after irradiating the cell, for example 1 minute to 30 minutes, 10 minutes to 30 minutes, 10 minutes to 1 hour, 1 hour to 8 hours, 6 hours to 24 hours, or 6 hours to 48 hours after irradiating the cell), thereby detecting the cell killing in real-time. Shortening FLT serves as an indicator of acute membrane damage induced by PIT. Thus, the cell is irradiated under conditions sufficient to shorten IR700 FLT by at least 25%, such as at least 40%, at least 50%, at least 60% or at least 75%. In one example, the cell is irradiated at a wavelength of 660 nm to 740 nm (such as 680 nm to 700 nm) and at a dose of at least 20 J cm$^{-2}$ or at least 30 J cm$^{-2}$, such as at least 40 J cm$^{-2}$ or at least 50$^{-2}$ J cm$^{-2}$ or at least 60 J cm$^{-2}$, such as 30 to 50 J cm$^{-2}$.

In some examples, methods of detecting cell killing in real time includes contacting the cell with one or more additional therapeutic agents, for example about 0 to 8 hours after irradiating the cell. The real-time imaging can occur before or after contacting the cell with one or more additional therapeutic agents. For example, if insufficient cell killing occurs after administration of the one or more antibody-IR700 molecules as determined by the real-timing imaging, then the cell can be contacted with one or more additional therapeutic agents. However, in some examples, the cell is contacted with the antibody-IR700 molecules and additional therapeutic agents prior to detecting the cell killing in real-time.

Exemplary Cells

The target cell can be a cell that is not desired or whose growth is not desired, such as a tumor cell. The cells can be growing in culture, or present in a mammal to be treated, such as a patient with cancer. Any target cell can be treated with the claimed methods. In one example, the target cell expresses a cell surface protein that is not substantially found on the surface of other normal (desired) cells, an antibody can be selected that specifically binds to such protein, and an antibody-IR700 molecule generated for that protein. In one example, the cell surface protein is a tumor-specific protein. In one example, the cell surface protein is CD25, which can be used to target cells associated with undesired transplant rejection.

In one example, the tumor cell is a cancer cell, such as a cell in a patient with cancer. Exemplary cells that can be killed with the disclosed methods include cells of the following tumors: a liquid tumor such as a leukemia, including acute leukemia (such as acute lymphocytic leukemia, acute myelocytic leukemia, and myeloblastic, promyelocytic, myelomonocytic, monocytic and erythroleukemia), chronic leukemias (such as chronic myelocytic (granulocytic) leukemia and chronic lymphocytic leukemia), polycythemia vera, lymphoma, Hodgkin's disease, non-Hodgkin's lymphoma, multiple myeloma, Waldenstrdm's macroglobulinemia, heavy chain disease). In another example the cell is a solid tumor cell, such as sarcomas and carcinomas, fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, pancreatic cancer, breast cancer, ovarian cancer, prostate cancer, hepatocellular carcinomna, lung cancer, colorectal cancer, squamous cell carcinoma, basal cell carcinoma, adenocarcinoma (for example adenocarcinoma of the pancreas, colon, ovary, lung, breast, stomach, prostate, cervix, or esophagus), sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, bladder carcinoma, CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma).

Exemplary Subjects

In some examples the disclosed methods are used to treat a subject who has a tumor, such as a tumor described herein. In some examples, the tumor has been previously treated, such as surgically or chemically removed, and the disclosed methods are used subsequently to kill any remaining undesired tumor cells that may remain in the patient.

The disclosed methods can be used to treat any mammalian subject, such as a human, who has a tumor, such as a cancer, or has had such previously removed or treated. Subjects in need of the disclosed therapies can include human subjects having cancer, wherein the cancer cells express a tumor-specific protein on their surface that can specifically bind to the antibody-IR700 molecule. For example, the disclosed methods can be used as initial treatment for cancer either alone, or in combination with radiation or other chemotherapy. The disclosed methods can also be used in patients who have failed previous radiation or chemotherapy. Thus, in some examples, the subject is one who has received other therapies, but those other therapies have not provided a desired therapeutic response. The disclosed methods can also be used in patients with localized and/or metastatic cancer.

In some examples the method includes selecting a subject that will benefit from the disclosed therapies, such as selecting a subject having a tumor that expresses a cell surface protein (such as a tumor-specific protein) that can specifically bind to an antibody-IR700 molecule. For example, if the subject is determined to have a breast cancer that expresses HER2, the subject can be selected to be treated with an anti-HER2-IR700 molecule, such as Tra-IR700 described in Example 1, and the subject subsequently irradiated as described herein.

Exemplary Cell Surface Proteins

In one example, the protein on the cell surface of the target cell to be killed is not present in significant amounts on other cells. For example, the cell surface protein can be a receptor that is only found on the target cell type.

In a specific example, the cell surface protein is a tumor-specific protein (also known in the art as a tumor-specific antigen), such as members of the EGF receptor family (e.g., HER1, 2, 3, and 4) and cytokine receptors (e.g., CD20, CD25, IL-13R, CD5, CD52, etc.). Tumor specific proteins are those proteins that are unique to cancer cells or are much more abundant on them, as compared to other cells, such as normal cells. For example HER2 is primarily found in breast cancers, while HER1 is primarily found in adenocarcinomas, which can be found in many organs, such as the pancreas, breast, prostate and colon.

Exemplary tumor-specific proteins that can be found on a target cell (and to which an antibody specific for that protein can be used to formulate an antibody-IR700 molecule), include but are not limited to: any of the various MAGEs (Melanoma-Associated Antigen E), including MAGE 1 (e.g., GenBank Accession Nos. M77481 and AAA03229), MAGE 2 (e.g., GenBank Accession Nos. L18920 and AAA17729), MAGE 3 (e.g., GenBank Accession Nos. U03735 and AAA17446), MAGE 4 (e.g., GenBank Accession Nos. D32075 and A06841.1), etc.; any of the various tyrosinases (e.g., GenBank Accession Nos. U01873 and AAB60319); mutant ras; mutant p53 (e.g., GenBank Accession Nos. X54156, CAA38095 and AA494311); p97 melanoma antigen (e.g., GenBank Accession Nos. M12154 and AAA59992); human milk fat globule (HMFG) associated with breast tumors (e.g., GenBank Accession Nos. S56151 and AAB19771); any of the various BAGEs (Human B melanoma-Associated Antigen E), including BAGE1 (e.g., GenBank Accession No. Q13072) and BAGE2 (e.g., GenBank Accession Nos. NM_182482 and NP_872288), any of the various GAGEs (G antigen), including GAGE1 (e.g., GenBank Accession No. Q13065) or any of GAGE2-6; various gangliosides, CD25 (e.g., GenBank Accession Nos. NP_000408.1 and NM_000417.2).

Other tumor-specific antigens include the HPV 16/18 and E6/E7 antigens associated with cervical cancers (e.g., GenBank Accession Nos. NC_001526, FJ952142.1, ADB94605, ADB94606, and U89349), mucin (MUC 1)-KLH antigen associated with breast carcinoma (e.g., GenBank Accession Nos. J03651 and AAA35756), CEA (carcinoembryonic antigen) associated with colorectal cancer (e.g., GenBank Accession Nos. X98311 and CAA66955), gp100 (e.g., GenBank Accession Nos. S73003 and AAC60634) associated with for example melanoma, MARTI antigens associated with melanoma (e.g., GenBank Accession No. NP_005502), cancer antigen 125 (CA125, also known as mucin 16 or MUC16) associated with ovarian and other cancers (e.g., GenBank Accession Nos. NM_024690 and NP_078966); alpha-fetoprotein (AFP) associated with liver cancer (e.g., GenBank Accession Nos. NM_001134 and NP_001125); Lewis Y antigen associated with colorectal, biliary, breast, small-cell lung, and other cancers; tumor-associated glycoprotein 72 (TAG72) associated with adenocarcinomas; and the PSA antigen associated with prostate cancer (e.g., GenBank Accession Nos. X14810 and CAA32915).

Other exemplary tumor-specific proteins further include, but are not limited to, PMSA (prostate membrane specific antigen; e.g., GenBank Accession Nos. AAA60209 and AAB81971.1) associated with solid tumor neovasculature, as well prostate cancer, HER-2 (human epidermal growth factor receptor 2, e.g., GenBank Accession Nos. M16789.1, M16790.1, M16791.1, M16792.1 and AAA58637) associated with breast cancer, ovarian cancer, stomach cancer and uterine cancer, HER-1 (e.g., GenBank Accession Nos. NM_005228 and NP_005219) associated with lung cancer, anal cancer, and glioblastoma as well as adenocarcinomas; NY-ESO-1 (e.g. GenBank Accession Nos. U87459 and AAB49693) associated with melanoma, sarcomas, testicular carcinomas, and other cancers, hTERT (aka telomerase) (e.g., GenBank Accession. Nos. NM_198253 and NP_937983 (variant 1), NM_198255 and NP_937986 (variant 2)); proteinase 3 (e.g., GenBank Accession Nos. M29142, M75154, M96839, X55668, NM 00277, M96628, X56606, CAA39943 and AAA36342), and Wilms tumor 1 (WT-1, e.g. GenBank Accession Nos. NM_000378 and NP_000369 (variant A), NM_024424 and NP_077742 (variant B), NM_024425 and NP_077743 (variant C), and NM_024426 and NP_077744 (variant D)).

In one example the tumor-specific protein is CD52 (e.g., GenBank Accession. Nos. AAH27495.1 and CAI15846.1) associated with chronic lymphocytic leukemia; CD33 (e.g., GenBank Accession. Nos. NM_023068 and CAD36509.1) associated with acute myelogenous leukemia; and CD20 (e.g., GenBank Accession. Nos. NP_068769 NP_031667) associated with Non-Hodgkin lymphoma.

Thus, the disclosed methods can be used to treat any cancer that expresses a tumor-specific protein.

Exemplary Antibody-IR700 Molecules

One skilled in the art will recognize that because cell surface protein sequences are publically available (as for example shown above), that making or purchasing antibodies (or other small molecules that can be conjugated to IR700) specific for such proteins is routine. For example, if the tumor-specific protein HER2 is selected as a target, antibodies specific for HER2 (such as Trastuzumab) can be purchased or generated and attached to the IR700 dye. In one example, a patient is treated with at least two different antibody-IR700 molecules. In one example, the two different antibody-IR700 molecules are specific for the same protein (such as HER-2), but are specific for different epitopes of the protein (such as epitope 1 and epitope 2 of HER-2). In another example, the two different antibody-IR700 molecules are specific for two different proteins or antigens, such as one antibody specific for CD4, and another antibody specific for CD25, which could be used for example to treat a T cell leukemia. For example, antiHER1-IR700 and antiHER2-IR700 could be injected together as a cocktail to facilitate killing of cells bearing either HER1 or HER2. Other specific examples are provided in the table below. In one example, the antibody is a humanized monoclonal antibody. Antibody-IR700 molecules can be generated using routine methods, such as those described in Example 1 below. Thus, the disclosure also provides antibody-IR700 molecules, compositions that include such molecules, and kits that include such molecules (for example a kit that includes one or more antibody-IR700 molecules and a chemotherapeutic agent, or a molecular targeting agent, or combinations thereof).

| Tumor-Specific Antigen | Exemplary Tumors | Exemplary Antibody/Small Molecules |
|---|---|---|
| HER1 | Adenocarcinoma (e.g., colorectal cancer, head and neck cancer) | Cetuximab, panitumamab, zalutumumab, nimotuzumab, matuzumab. Small molecule inhibitors gefitinib, erlotinib, and lapatinib can also be used. |

| Tumor-Specific Antigen | Exemplary Tumors | Exemplary Antibody/Small Molecules |
|---|---|---|
| HER2 | breast cancer, ovarian cancer, stomach cancer, uterine cancer | Trastuzumab (Herceptin ®), pertuzumab |
| CD20 | Non-Hodgkin lymphoma | Tositumomab (Bexxar ®); Rituximab (Rituxan, Mabthera); or Ibritumomab tiuxetan (Zevalin, for example in combination with yttrium-90 or indium-111 therapy) |
| CD25 | T-cell lymphoma | Daclizumab (Zenapax) |
| CD33 | Acute myelogenous leukemia | Gemtuzumab (Mylotarg, for example in combination with calicheamicin therapy) |
| CD52 | chronic lymphocytic leukemia | Alemtuzumab (Campath) |
| CEA | colorectal cancer, some gastric cancers, biliary cancer | CEA-scan (Fab fragment, approved by FDA), colo101 |
| Cancer antigen 125 (CA125) | ovarian cancer, mesothelioma, breast cancer | OC125 monoclonal antibody |
| Alpha-fetoprotein (AFP) | hepatocellular carcinoma | ab75705 (available from Abcam) and other commercially available AFP antibodies |
| Lewis Y | colorectal cancer, biliary cancer | B3 (Humanized) |
| TAG72 | adenocarcinomas including colorectal, pancreatic, gastric, ovarian, endometrial, mammary, and non-small cell lung cancer | B72.3 (FDA-approved monoclonal antibody) |
| Vascular endothelial growth factor | Colorectal cancer | Bevacizumab (Avastin ®) |

Antibody-IR700 molecules for treating transplant rejection can also be generated using Basiliximab or Daclizumab which target IL-2Rα receptor (CD25)

Administration of Antibody-IR700 Molecules and Additional Therapeutic Agents

Antibody-IR700 molecules and additional therapeutic agents (such as anti-neoplastic agents) can be contacted with a cell in vitro, for example by adding the antibody-IR700 molecules and additional therapeutic to growth media in which the cells or growing, or can be contacted with a cell in vivo, for example by administering the antibody-IR700 molecules and additional therapeutic agents to the subject to be treated.

The antibody-IR700 molecules and additional therapeutic agents can be administered locally or systemically using any method known in the art, for example to subjects having a tumor, such as a cancer, or who has had a tumor previously removed (for example via surgery). Although specific examples are provided, one skilled in the art will appreciate that alternative methods of administration of the disclosed antibody-IR700 molecules and additional therapeutic agents can be used. Such methods may include for example, the use of catheters or implantable pumps to provide continuous infusion over a period of several hours to several days into the subject in need of treatment.

In one example, the antibody-IR700 molecules and additional therapeutic agents are administered by parenteral means, including direct injection or infusion into a tumor (intratumorally). In some examples, the antibody-IR700 molecules and additional therapeutic agents are administered to the tumor by applying the antibody-IR700 molecules and additional therapeutic agents to the tumor, for example by bathing the tumor in a solution containing the antibody-IR700 molecules and additional therapeutic agents or by pouring the antibody-IR700 molecules and additional therapeutic agents onto the tumor.

In addition, or alternatively, the disclosed compositions can be administered systemically, for example intravenously, intramuscularly, subcutaneously, intradermally, intraperitoneally, subcutaneously, or orally, to a subject having a tumor (such as cancer).

The dosages of the antibody-IR700 molecules (and additional therapeutic agents) to be administered to a subject are not subject to absolute limits, but will depend on the nature of the composition and its active ingredients and its unwanted side effects (e.g., immune response against the antibody), the subject being treated and the type of condition being treated and the manner of administration. Generally the dose will be a therapeutically effective amount, such as an amount sufficient to achieve a desired biological effect, for example an amount that is effective to decrease the size (e.g., volume and/or weight) of the tumor, or attenuate further growth of the tumor, or decrease undesired symptoms of the tumor. Dosages of additional therapeutic agents are known in the art.

For intravenous administration of the antibody-IR700 molecules, exemplary dosages for administration to a subject for a single treatment can range from 0.5 to 100 mg/60 kg of body weight, 1 to 100 mg/60 kg of body weight, 1 to 50 mg/60 kg of body weight, 1 to 20 mg/60 kg of body weight, for example about 1 or 2 mg/60 kg of body weight. In yet another example, a therapeutically effective amount of ip or intratumoral administered antibody-IR700 molecules can vary from 10 µg to 5000 µg of antibody-IR700 molecule to 1 kg of body weight, such as 10 µg/kg to 1000 µg/kg, 10 µg/kg to 500 µg/kg, or 100 µg/kg to 1000 µg/kg.

In one example, the dose of antibody-IR700 molecule administered to a human patient is at least 50 mg, such as at least 100 mg, at least 300 mg, at least 500 mg, at least 750 mg, or even 1 g.

Treatments with disclosed antibody-IR700 molecules (and additional therapeutic agents) can be completed in a single day, or may be done repeatedly on multiple days with the same or a different dosage. Repeated treatments may be done on the same day, on successive days, or every 1-3 days, every 3-7 days, every 1-2 weeks, every 2-4 weeks, every 1-2 months, or at even longer intervals.

Irradiation of Cells

After the cells are contacted with one or more antibody-IR700 molecules, they are irradiated. Methods of irradiation are well known in the art. As only cells expressing the cell surface protein will be recognized by the antibody, only those cells will have sufficient amounts of the antibody-IR700 molecules bound to it. This decreases the likelihood of undesired side effects, such as killing of normal cells, as the irradiation will only kill the cells to which the antibody-IR700 molecules are bound, not the other cells.

In some examples, cells are irradiated in vitro, such as in a tissue culture dish. In other examples, a cell is irradiated in vivo, for example irradiating a subject who has previously been administered antibody-IR700 molecules. In some examples, the subject is irradiated, for example a tumor in the subject can be irradiated.

The cells are irradiated with a therapeutic dose of radiation at a wavelength of 660-710 nm, such as 660-700 nm, 680-7000 nm, 670-690 nm, for example, 680 nm. In particular examples, the cells are irradiated at a dose of at least 1 J cm$^{-2}$, such as at least 10 J cm$^{-2}$, at least 30 J cm$^{-2}$, at least 50 J cm$^{-2}$, at least 100 J cm$^{-2}$, or at least 500 J cm$^{-2}$, for example, 1-1000 J cm$^{-2}$, 1-500 J cm$^{-2}$, 30 to 50 J cm$^{-2}$, 10-100 J cm$^{-2}$, or 10-50 J cm$^{-2}$.

Cells (or patients) can be irradiated one or more times. Thus, irradiation can be completed in a single day, or may be done repeatedly on multiple days with the same or a different dosage (such as irradiation at least 2 different times, 3 different times, 4 different times 5 different times or 10 different times). Repeated irradiations may be done on the same day, on successive days, or every 1-3 days, every 3-7 days, every 1-2 weeks, every 2-4 weeks, every 1-2 months, or at even longer intervals.

Exemplary Devices Containing NIR LEDs

Any type of item that can be worn or placed on the body, and is amenable to the incorporation of NIR LEDs, can be used. In one example, the device is a chamber into which the patient is inserted. Such devices can be used in the treatment of tumor cells circulating in the blood or lymph, such as leukemias, lymphomas, as well as metastatic cells present in the blood or lymph. In some examples, such devices can be used in the treatment of tumor cells present on the skin, such as a melanoma.

To kill all the cells circulating in the body it may be necessary to wear the devices for an extended period of time, such as several weeks or months. Thus, these devices can be incorporated into every day clothing, jewelry and nightwear such as blankets. These devices make it possible to expose the patient to NIR light using portable everyday articles of clothing and jewelry so that treatment remains private and does not interfere with everyday activities. For instance, a necklace incorporating NIR LEDs can be customizable to the patient's tastes, and worn discreetly during the day for PIT therapy (for example by killing tumor cells that pass through the carotid artery and other vasculature in the neck). Multiple devices of a similar "everyday" nature (blankets, bracelets, necklaces, underwear, socks, shoe inserts and the like) could be worn by the same patient during the treatment period. For example while sleeping, a patient could use the NIR blanket. The devices can also include a power supply, such as a battery, and a cooling element to prevent overheating for such devices as blankets.

In one example, the device is jewelry, such as a ring, watch, bracelet, or necklace. In another example, the item is an article of clothing or accessory, such as a shirt, belt, pants, underwear, socks, coat, shoe insert, scarf, hat, wrist guard, gloves, and the like. In another example, the device is an article that can cover the body, such as a blanket or towel. In another example, the device is a whole body light chamber that exposes the skin directly (such a device could also include a power supply and/or cooling supply).

By wearing the device that incorporates one or more NIR LEDs (such as at least 2, at least 3, at least 4, at least 5, at least 10, at least 20, or at least 50 NIR LEDs), tumor cells or other cells to be killed that are present in the blood or lymph become exposed to the light generated by the NIR LEDs (such as an NIR LED that emits at 660 to 740 nm, such as 670 to 700 nm or 680 to 720 nm). The light emitted from the NIR LED can penetrate the skin and blood vessels (such as the carotid artery or microvasculature in the skin), thus allowing the light to activate the antibody-IR700 molecule bound to the target cells, thus killing the cells to which the antibody-IR700 molecule is bound. The NIR LEDs can be arranged in the device to ensure that the skin or the blood vessels or lymphatic system are targeted.

NIR LED devices that can be used in the methods provided herein are commercially available. The applicable products from one manufacturer, Marubeni America, are listed below. The first product, a molded LED, has low power but it could be used over a longer exposure time. The other options have higher power and thus may benefit from provisions for additional cooling. Except for the last one, which is packaged in a 25 mm×18 mm metal case, the others are applicable to wearable devices such as bracelets, necklace, underwear, socks, gloves, hats and other wearable items. All are usable in blankets, handheld devices or chambers.

For example, Marubeni America Corporation provides the following NIR LEDs with lens options to set the irradiation pattern: Molded LED which is 5 mm in diameter, has a total radiated power of 4 mW, calculated power density of 5 mW cm$^{-2}$ and a power requirement of 1.8V 20 mA; Surface Mount LED which is 3.5 mm×2.7 mm, has a total radiated power of 3 mW, calculated power density of 32 mW cm$^{-2}$, and a power requirement of 1.9V 50 mA; Super Beam which is 7.6 mm×7.6 mm, has a total radiated power of 20-52 mW, calculated power density of 34-90 mW cm$^{-2}$, and a power requirement of 1.65V 100 mA; High Power Surface Mount which is 5 mm×5 mm or 7 mm diameter, has a total radiated power of 90 mW, calculated power density of 360 mW cm$^{-2}$ and a power requirement of 2.4V 500 mA; and High Power Illuminators which is 25 mm×18 mm, has a total radiated power of 150 mW, a calculated power density of 33 mW cm$^{-2}$ and a power requirement of 10V 120 mA. Alternatively, such devices can be made that emit light at 690 nm with a similar power with short strong intermittent pulse.

During in vitro experimentation, NIR light with a power density of 2.2 mW cm$^{-2}$ (or 2.2 mJ s$^{-1}$ cm$^{-2}$) induced cell death. Assuming an attenuation coefficient for tissue of 4 cm$^{-1}$, the intensity of the light would be down to 10% at 5.8 mm and 1% at 12 mm. This indicates that for in vivo applications, the power density required needs to be 10-100 times larger. That is, the dose of light emitted by the NIR LED device in some examples is at least 20 mW cm$^{-2}$, such as at least 50 mW cm$^{-2}$, at least 100 mW cm$^{-2}$, at least 150 mW cm$^{-2}$, at least 200 mW cm$^{-2}$ or, at least 300 mW cm$^{-2}$. Multiple NIR LEDs can be arranged in a two-dimensional array to cover larger areas. In one example, a laser is used as the NIR light source as an alternative to an LED.

The NIR LEDs can be powered by using a power supply (which may be directly or indirectly part of the device). The power supply requirement would depend on the number of LEDs in the device. For example, one or more batteries can be used to power the NIR LED. For some LEDs, 4 AA batteries can power 3 LEDs in series. An alkaline AA battery is rated at a maximum of 3000 mAh so this configuration provide powers for up to 150, 60, and 30 hr at 20, 50 and 100 mA.

In some examples, the device further includes a cooling device (which may be directly or indirectly part of the device). For example, heat sinks can be used for passive or active cooling. Another alternative is a thermoelectric effect (Peltier). This would draw additional power but it can be used in applications where the power requirements would need a plug-in AC adapter.

Another type of device that can be used with the disclosed methods is a flashlight-like device with NIR LEDs. Such a device can be used for focal therapy of lesions during surgery, or incorporated into endoscopes to apply NIR light to body surfaces after the administration of PIT agent. Such devices can be used by physicians or qualified health personnel to direct treatment to particular targets on the body.

Treatment Using Wearable NIR LEDs

As described herein, the disclosed methods are highly specific for cancer cells. However, in order to kill the cells circulating in the body or present on the skin, the patient can wear a device that incorporates an NIR LED. In some example the patient uses at least two devices, for example an article of clothing or jewelry during the day, and a blanket at night. In some example the patient uses at least two devices at the same time, for example two articles of clothing. These devices make it possible to expose the patient to NIR light using portable everyday articles of clothing and jewelry so that treatment remains private and does not interfere with everyday activities. In some examples, the device can be worn discreetly during the day for PIT therapy.

In one example, the patient is administered one or more antibody-IR700 molecules, using the methods described herein. The patient then wears a device that incorporates an NIR LED, permitting long-term therapy and treatment of tumor cells that are present in the blood or lymph or on the skin. In some examples, the dose is at least at least 1 J cm$^{-2}$, at least 10 J cm$^{-2}$, at least 20 J cm$^{-2}$, or at least 30 J cm$^{-2}$, such as 20 J cm$^{-2}$ or 30 J/cm$^2$. In some examples, administration of the antibody-IR700 molecule is repeated over a period of time (such as bi-weekly or monthly, to ensure therapeutic levels are present in the body.

In some examples, the patient wears or uses the device, or combination of devices, for at least 1 week, such as at least 2 weeks, at least 4 weeks, at least 8 weeks, at least 12 weeks, at least 4 months, at least 6 months, or even at least 1 year. In some examples, the patient wears or uses the device, or combination of devices, for at least 4 hours a day, such as at least 12 hours a day, at least 16 hours a day, at least 18 hours a day, or 24 hours a day. It is quite possible that multiple devices of a similar "everyday" nature (blankets, bracelets, necklaces, underwear, socks, shoe inserts) could be worn by the same patient during the treatment period. At night the patient can use the NIR LED blanket or other covering.

Additional Treatments

As discussed above, prior to, during, or following administration of one or more antibody-IR700 molecules, the subject can receive one or more other therapies. In one example, the subject receives one or more treatments to remove or reduce the tumor prior to administration of the antibody-IR700 molecules.

Examples of such therapies that can be used in combination with the disclosed PIT methods, which enhance accessibility of the tumor to additional therapeutic agents for about 8 hours after the PIT, but are not limited to, surgical treatment for removal or reduction of the tumor (such as surgical resection, cryotherapy, or chemoembolization), as well as anti-tumor pharmaceutical treatments which can include radiotherapeutic agents, anti-neoplastic chemotherapeutic agents, antibiotics, alkylating agents and antioxidants, kinase inhibitors, and other agents. In some examples, the additional therapeutic agent is conjugated to a nanoparticle. Particular examples of additional therapeutic agents that can be used include microtubule binding agents, DNA intercalators or cross-linkers, DNA synthesis inhibitors, DNA and/or RNA transcription inhibitors, antibodies, enzymes, enzyme inhibitors, and gene regulators. These agents (which are administered at a therapeutically effective amount) and treatments can be used alone or in combination. Methods and therapeutic dosages of such agents are known to those skilled in the art, and can be determined by a skilled clinician.

"Microtubule binding agent" refers to an agent that interacts with tubulin to stabilize or destabilize microtubule formation thereby inhibiting cell division. Examples of microtubule binding agents that can be used in conjunction with the disclosed antibody-IR700 molecule therapies include, without limitation, paclitaxel, docetaxel, vinblastine, vindesine, vinorelbine (navelbine), the epothilones, colchicine, dolastatin 15, nocodazole, podophyllotoxin and rhizoxin. Analogs and derivatives of such compounds also can be used and are known to those of ordinary skill in the art. For example, suitable epothilones and epothilone analogs are described in International Publication No. WO 2004/018478. Taxoids, such as paclitaxel and docetaxel, as well as the analogs of paclitaxel taught by U.S. Pat. Nos. 6,610,860; 5,530,020; and 5,912,264 can be used.

The following classes of compounds can be used with the PIT methods disclosed herein: suitable DNA and/or RNA transcription regulators, including, without limitation, actinomycin D, daunorubicin, doxorubicin and derivatives and analogs thereof also are suitable for use in combination with the disclosed therapies. DNA intercalators and cross-linking agents that can be administered to a subject include, without limitation, cisplatin, carboplatin, oxaliplatin, mitomycins, such as mitomycin C, bleomycin, chlorambucil, cyclophosphamide and derivatives and analogs thereof. DNA synthesis inhibitors suitable for use as therapeutic agents include, without limitation, methotrexate, 5-fluoro-5'-deoxyuridine, 5-fluorouracil and analogs thereof. Examples of suitable enzyme inhibitors include, without limitation, camptothecin, etoposide, formestane, trichostatin and derivatives and analogs thereof. Suitable compounds that affect gene regulation include agents that result in increased or decreased expression of one or more genes, such as raloxifene, 5-azacytidine, 5-aza-2'-deoxycytidine, tamoxifen, 4-hydroxytamoxifen, mifepristone and derivatives and analogs thereof. Kinase inhibitors include Gleevc® imatinib mesylate, Iressa® gefitinib, and Tarceva® erlotinib that prevent phosphorylation and activation of growth factors.

Other therapeutic agents, for example anti-tumor agents, that may or may not fall under one or more of the classifications above, also are suitable for administration in combination with the disclosed PIT therapies. By way of example, such agents include adriamycin, apigenin, rapamycin, zebularine, cimetidine, and derivatives and analogs thereof.

In some examples, the subject receiving the therapeutic antibody-IR700 molecule composition is also administered interleukin-2 (IL-2), for example via intravenous administration. In particular examples, IL-2 (Chiron Corp., Emeryville, Calif.) is administered at a dose of at least 500,000 IU/kg as an intravenous bolus over a 15 minute period every eight hours beginning on the day after administration of the peptides and continuing for up to 5 days. Doses can be skipped depending on subject tolerance.

In some examples, the disclosed antibody-IR700 molecules can be co-administered (or administered shortly before or after the irradiation) with a fully human antibody to cytotoxic T-lymphocyte antigen-4 (anti-CTLA-4). In some example subjects receive at least 1 mg/kg anti-CTLA-4 (such as 3 mg/kg every 3 weeks or 3 mg/kg as the initial dose with subsequent doses reduced to 1 mg/kg every 3 weeks).

In one example, at least a portion of the tumor (such as a metastatic tumor) is surgically removed (for example via cryotherapy), irradiated, chemically treated (for example via chemoembolization) or combinations thereof, prior to administration of the disclosed therapies (such as administration of antibody-IR700 molecules). For example, a subject having a metastatic tumor can have all or part of the tumor surgically excised prior to administration of the disclosed therapies. In an example, one or more chemotherapeutic agents are administered following treatment with antibody-IR700 molecules and irradiation. In another particular example, the subject has a metastatic tumor and is administered radiation therapy, chemoembolization therapy, or both concurrently with the administration of the disclosed therapies.

Example 1

Synthesis of IRDye 700-Conjugated Trastuzumab (Anti-Her2)

This example describes methods used to conjugate the monoclonal antibody Trastuzumab to the IRDye 700DX NHS Ester. On skilled in the art will recognize that any antibody, such as any monoclonal antibody specific for a target cell surface protein, can be conjugated to IRDye 700DX NHS Ester using similar methods.

Humanized anti-HER2 antibody, Trastuzumab (Tra; Genentech, San Francisco, Calif.) (1 mg, 6.8 nmol) was incubated with IRDye 700DX NHS Ester (IR700; LI-COR Bioscience, Lincoln, Nebr.) (66.8 µg, 34.2 nmol, 5 mmol/L in DMSO) in 0.1 mol/L $Na_2HPO_4$ (pH 8.5) at room temperature for 30 to 120 min. Trastuzumab is a recombinant humanized monoclonal antibody (mAb) directed against the extracellular domain of the human epidermal growth factor receptor (EGFR) 2 (HER2) tyrosine kinase receptor. The mixture was purified with a Sephadex G50 column (PD-10; GE Healthcare, Piscataway, N.J.). The protein concentration was determined with Coomassie Plus protein assay kit (Pierce Biotechnology, Rockford, Ill.) by measuring the absorption at 595 nm with a UV-Vis system (8453 Value System; Agilent Technologies, Palo Alto, Calif.). The concentration of IR700 was measured by absorption with the UV-Vis system to confirm the number of fluorophore molecules conjugated to each Trastuzumab molecule. The number of IR700 per Trastuzumab was about 3.

The purity of the Tra-IR700 conjugate was confirmed by analytical size-exclusion HPLC (SE-HPLC) and sodium dodecyl sulfate polyacrylamidegel elctrophoresis (SDS-PAGE). SE-HPLC was performed using a Beckman System Gold (Fullerton, Calif.) equipped with model 126 solvent delivery module, a model 168 UV detector, and a JASCO fluorescence detector (excitation 689 nm and emission at 700 nm) controlled by 32 Karat software. SE chromatography was performed on a TSKgel G2000SWx1 (Tosoh Bioscience LLC, Montgomeryville, Pa.) eluted for 45 minutes using phosphate buffered saline (PBS) at 0.5 mL/min. SDS-PAGE was performed with a 4% to 20% gradient polyacrylamide gel (Invitrogen, Carlsbad, Calif.). Just after separating the proteins, fluorescence intensity was analyzed with a Fujifilm FLA-5100 fluorescence scanner (Valhalla, N.Y.) with an internal laser of 670 nm for excitation and 705 nm long pass filter for emission. The fluorescence intensity of each band was analyzed with Multigage software (Fujifilm). The gels were then stained with Colloidal Blue Staining Kit (Invitrogen), and digitally scanned. The protein concentration in each band was analyzed with ImageJ software. The trastuzumab-1R700 (Tra-1R700) and panitumumab-1R700 (Pan-1R700; see Example 8) preparations demonstrated strong association and contained no detectable MAb aggregates as determined by high performance liquid chromatography (HPLC) and sodium dodecyl sulfate polyacrylamide-gel electrophoresis SDS-PAGE.

To determine the in vitro binding characteristics of IR700 conjugates $^{125}$I labeling of the conjugates using the Indo-Gen procedure was performed. The specific activities of the radiolabeled antibodies were 8.52 mCi/mg for Trastuzumab and 7.84 mCi/mg for panitumumab (see Example 8 below). It was observed that 73.38±0.39% ($^{125}$I-Tra-IR700) and 78.61±0.89% ($^{125}$I-Pan-IR700) of binding was achieved with each MAb conjugate respectively and the specificity of binding was confirmed by blocking with excess native unconjugated MAb (less than 1.4%). Since immunoreactivity of $^{125}$I-Tra and $^{125}$I-Pan measured with the same method were 78±2%, and 82±3%, respectively, minimal loss of MAbs with IR700 conjugation was confirmed. Immunoreactivity assay was performed as described previously. Briefly, after trypsinization, $2\times10^6$ of 3T3/HER2 or A431 cells were resuspended in PBS containing 1% bovine serum albumin (BSA). $^{125}$I-Tra-IR700 or $^{125}$I-Pan-IR700 (1 mCi, 0.2 µg) was added and incubated for 1 h on ice. Cells were washed, pelleted, the supernatant decanted, and counted in a 2470 Wizard$^2$ γ-counter (Perkin Elmer, Shelton, Conn.). Nonspecific binding to the cells was examined under conditions of antibody excess (200 µg of nonlabeled trastuzumab or panitumumab).

Example 2

Selective Killing of HER2+ Cells

This example describes methods used to show that the Trastuzumab-IR700 compound described in Example 1 (referred to herein as Tra-IR700) can be used to selectively kill cells that express HER2 (HER2+), but has minimal negative effects on HER2 negative (HER2−) cells.

HER2 gene-transfected NIH3T3 (3T3/HER2+) cells were used for target photodynamic therapy (PDT). As a control, Balb/3T3 cells which express DsRed fluorescent protein but not HER2 (Balb/3T3/DsRed) were employed. Cells were grown in RPMI 1640 supplemented with 10% fetal bovine serum and 1% penicillin/streptomycin in tissue culture flasks in a humidified incubator at 37° C. in an atmosphere of 95% air and 5% carbon dioxide.

Fluorescence microscopy was performed with a BX51 or IX81 microscope (Olympus America, Melville, N.Y.). The filter was set to detect IR700 and consisted of a 590-650 nm excitation filter, and a 665-740 nm band pass emission filter. To detect DsRed protein, a filter set consisting of a 480-550 nm excitation filter, and a 590 nm long pass emission filter was employed.

Fluorescence microscopy was performed to test the subcellular localization of IR700 in 3T3/HER2+ cells. Cells were seeded on cover glass-bottomed dishes and incubated for 24 hours. Tra-IR700 was added to the culture medium at 10 µg/mL. As shown in FIG. 1A, Tra-IR700 was detected on the cell surface after 1 hour incubation on ice, and was mainly localized to the lysosome 6 hours after incubation at 37° C., indicating gradual internalization. Co-staining with LysoTracker Green (Invitrogen, Carlsbad, Calif.), which was detected by a filter set consisting of a 420-480 nm excitation filter, and a 520 nm long pass emission filter, revealed co-localization of IR700 with the endolysosomal compartment (FIG. 1B). After 1 h and 6 h of incubation with Tra-1R700, excitation light (fluorescence microscope; power density of 2.2 mW cm-2) induced fluorescence as well as cellular swelling, bleb formation, and rupture of vesicles representing necrotic cell death (FIG. 1C).

For photoimmunotherapy (PIT), cells were seeded on 35 mm cover glass-bottomed dishes and incubated 24 hours. Medium was replaced with fresh culture medium containing Tra-IR700 at 10 µg/mL and incubated for 6 hours at 37° C. Culture medium was replaced with phenol red-free medium after washing with phosphate buffered saline (PBS). Cells were irradiated with light at 670 nm to 690 nm using a red light emitting diode (LED; FluorVivo; INDEC Systems Inc., Capitola, Calif.) with a power density of 2.6 mW cm$^{-2}$ as measured with optical power meter (PM 100, Thorlabs, Newton, N.J.). Cell viability was assessed 1 hour after treatment with LIVE/DEAD® Fixable Green Dead Cell Stain Kit (Invitrogen). After the treatment, cells were trypsinized and washed with PBS. Green fluorescent reactive dye was added in the cell suspension and incubated at room temperature for 30 minutes. Cells were then analyzed on flow cytometer (FACS Calibur, BD BioSciences, San Jose, Calif.).

As shown in FIG. 1C, irradiation at 1.0 J cm-2 for 3T3/HER2+ cells resulted in rapid necrotic cell death, representing budding and swelling of the cell membrane.

Example 3

Identification of Irradiation Dose

To determine the phototoxicity in response to different doses of light irradiation, PDT-treated 3T3/HER2+ cells were assayed by flow cytometry using the LIVE/DEAD® Fixable Green Dead Cell Stain Kit. The LIVE/DEAD assay, which can detect the cells with damaged membranes, was performed within 1 h after the treatment. As shown in FIG. 1D, cell death in response to Tra-IR700-mediated PDT was light dose dependent 1 hour after PIT. Cells without PIT or Tra-IR700 did not show significant phototoxicity.

Example 4

Measurement of Cell Viability Over Time

To monitor cell viability over time, cells were labeled and irradiated as described in Example 2, then were monitored subsequently over time (5 days) using microscopy as described in Example 2.

As shown in FIG. 1F, phototoxic cell death was observed only in the treated 3T3/HER2+ cells with Tra-IR700, but not in the un-irradiated group (no PIT) or the group irradiated but did not receive Tra-IR700 (No Tra-IR700).

Example 5

Target Specific Phototoxicity of Tra-IR700

Figure 2A:
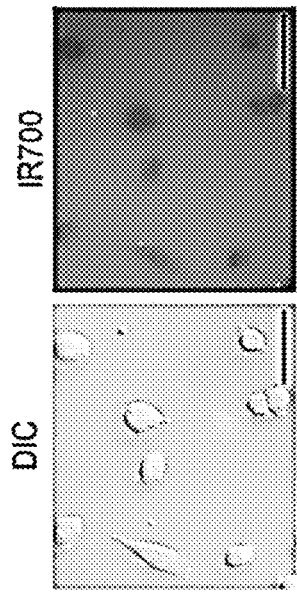
FIG. 2A is a graph showing that long term growth inhibition was not observed in Balb/3T3 (HER2 negative) cells treated with Tra-1R700 (TraIR) and exposed to light. Data are means±s.e.m. (n=3).
Figure 2B:
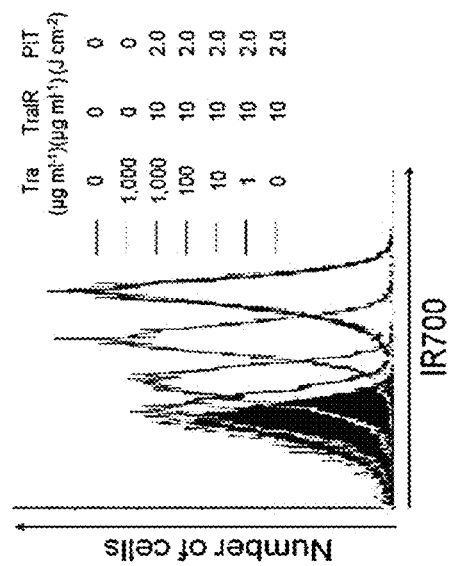
FIG. 2B is a digital image showing that Free IR700 dye did not incorporate into 3T3/HER2 cells. Fluorescence image was taken without washing the cells. Cells were darker than the media containing free IR700 dye. Scale bar, 50 μm.
Figure 2C:
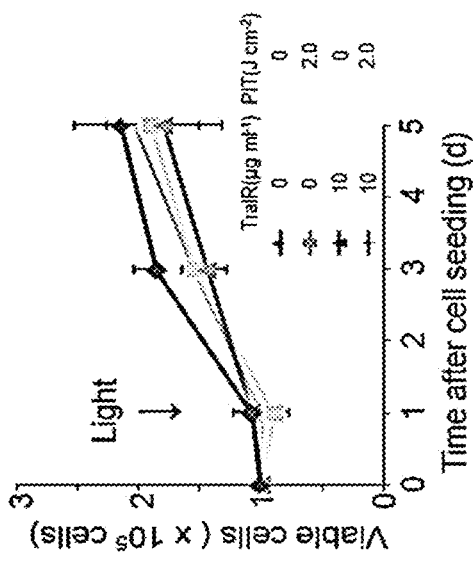
FIG. 2C is a graph showing that TraIR700 mediated phototoxicity was dose-dependently blocked by the excess of unconjugated trastuzumab (Tra). Data are means±s.e.m. (n=3).
Figure 2D:
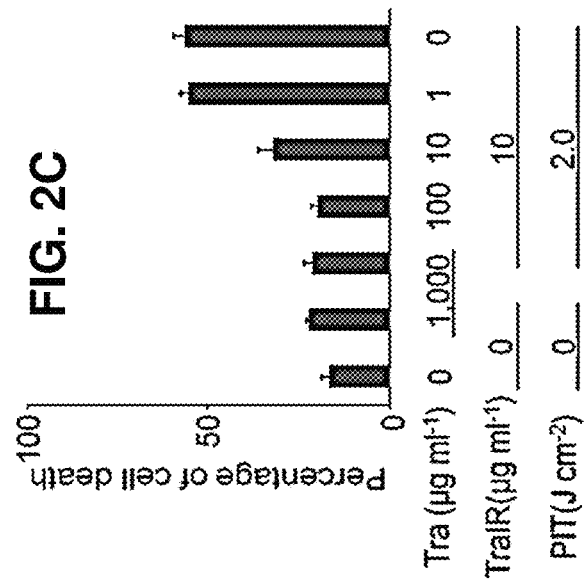
FIG. 2D is a graph showing that Tra-1R700 binding for 3T3/HER2 cells was blocked by unconjugated trastuzumab dose-dependent manner (n=3). DIC: differential interference contrast

PIT was performed as described in Example 2. As shown in FIG. 1G, there was no significant difference in phototoxicity between 1 h and 6 h incubation with Tra-1R700, indicating that membrane binding of Tra-1R700 was sufficient to induce cell death. When Tra-1R700 was localized to the endolysosomal compartment (FIG. 1B), it also induced rupture of the vesicle with cellular swelling and bleb formation after irradiation. However, this did not appear to be a major cause of cell death, since cell death was observed without endolysosomal localization of Tra-1R700 within 1 h of incubation at 4° C. Failure to wash the cells prior to irradiation did not influence the phototoxic effect, indicating that cellular membrane binding was important to the phototoxic effects of the conjugate, not merely the presence of the conjugate. Further, the IR700 dye alone (200 nM; equivalent IR700 concentration of Tra-1R700 conjugates) did not incorporate into the cells or induce phototoxcity in cells (FIG. 1H and FIG. 2B). Additionally, phototoxcity was dose-dependently blocked by the excess unconjugated trastuzumab (FIGS. 2C and 2D). Furthermore, Tra-1R700 did not induce therapeutic effect to A431 cells (FIG. 1I). These results confirm that cell death is dependent on specific membrane binding of Tra-1R700.

Reactive oxygen species (ROS) have been implicated in the cell death associated with conventional PDT. To clarify the role of photon-induced redox reactions (e.g. singlet oxygen ($^1O_2$)) in producing phototoxicity with Tra-1R700, a redox quencher, sodium azide (NaN$_3$), was added to the medium when cells were irradiated. The percentage of cell death was partially decreased in the presence of sodium azide, in a dose dependent manner (FIG. 1J).

Figure 3:
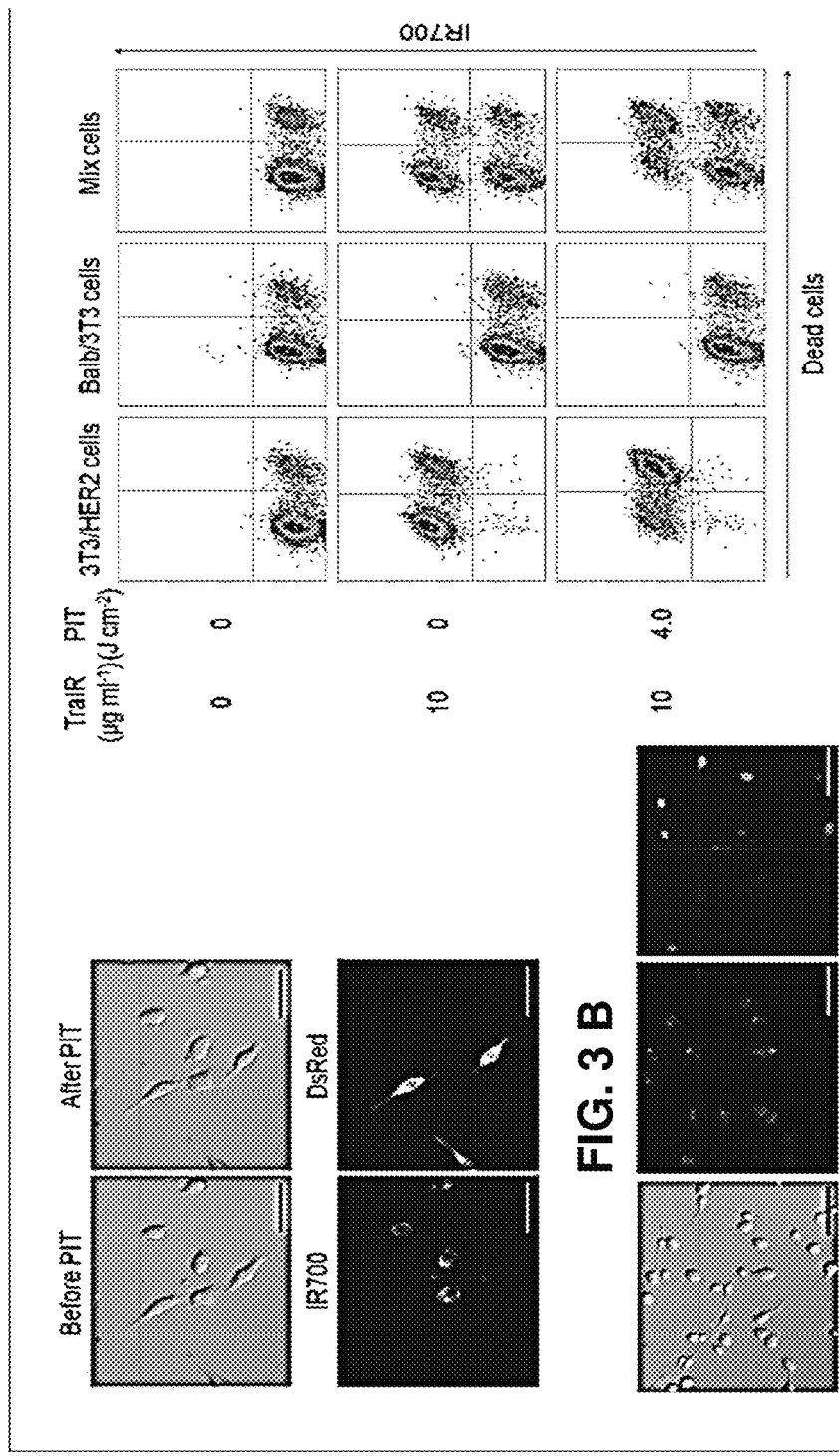
FIG. 3A is a digital image showing that induction of target specific photoimmunotherapy (PIT) lead to HER2 expressing cell specific necrotic cell death. Scale bar, 50 μm.
FIG. 3B is a digital image showing that HER2 specific cell death was confirmed with fluorescence microscopy with LIVE/DEAD Green staining. Scale bar, 100 μm.
FIG. 3C is a plot showing flow cytometric analysis for detecting HER2-specific cell death induced by Tra-1R700 (TraIR) mediated PIT. Upper left quadrant: TraIR700 positive, live cells; upper right quadrant: Tra-1R700 positive, dead cells; lower left quadrant: Tra-1R700 negative, live cells; lower right quadrant: Tra-1R700 negative, dead cells (n=3). DIC: differential interference contrast.

To confirm that the phototoxicity was target specific, 3T3/HER2+ cells and Balb/3T3/DsRed cells (a parental HER2 negative Balb/3T3 transfected with DsRed fluorescent protein) were co-cultured, and irradiated at 1.0 J cm$^{-2}$ after 1 or 6 hours of incubation with Tra-IR700 at 37° C. Tra-1R700 was distributed in a HER2 specific manner while DsRed expressing Balb/3T3 cells did not show phototoxicity upon irradiation (FIG. 3A). In addition, LIVE/DEAD Green staining demonstrated HER2 specific induction of cell death as determined by multi-color fluorescence microscopy (FIG. 3B) and flow cytometry analysis (FIG. 3C).

Example 6

Tra-IR700 Reduces Proliferation of HER2+ Cells

3T3/HER2 cells were seeded into 35 mm cell culture dishes at a density of 1×10$^4$. The next day, cells were incubated with or without Tra-IR700 and irradiated as described in Example 2. Cell viability was determined by trypan blue dye exclusion assay at day 1, 3 and 5 after the cell seeding. Viable cells for treated or untreated controls were counted on a hemacytometer after trypsinization. Cell growth was also photographed under microscope at each time point.

As shown in FIG. 1E, cells treated with Tra-IR700 and then subjected to PDT 2.0 J cm$^{-2}$ had significantly reduced viability as compared to cells only treated with Tra-IR700, only PDT, or no treatment.

Example 7

Tra-IR700 Selectively Kills HER2+ Cells In Vivo

This example describes methods used to show that Tra-IR700 can treat HER2+ tumors in vivo. One skilled in the art will appreciate that similar methods can be used with other tumor/antibody-IR700 combinations.

Six- to eight-week-old female homozygote athymic nude mice (Charles River, NCI-Frederick, Frederick, Md.) were anesthetized with isoflurane. 3T3/HER2+ or Balb/3T3 cells (2 million) were injected subcutaneously in the left dorsum of the mice. Four days after cell injection, either 50 or 300 µg of Tra-IR700 was administered intravenously. Her2-specific Tra-IR700 accumulation in tumor xenografts was confirmed with an in vivo fluorescence imaging system (Pearl Imager, LI-COR Biosciences, Lincoln, Nebr.). 3T3/HER2+ tumor-specific IR700-Tra localization was observed. In contrast, Balb/3T3 tumor did not show Her2-specific IR700 fluorescence.

To evaluate the efficacy of targeted PIT with IR700-Tra in vivo, 1 million 3T3/HER2+ or Balb/3T3 cells were injected subcutaneously into the bilateral dorsum of female nude mice. When the volume of both tumors reached ~70 mm$^3$ (about 4 days), animals were randomized into five groups of at least 12 animals per group for the following treatments: (1) no treatment; (2) 300 µg of trastuzumab injected intravenously, no PIT; (3) 300 µg of Tra-IR700 injected intravenously, no PIT; (4) PIT at 50 J/cm$^2$ for 3T3/HER2 tumor without Tra-IR700; (5) 300 µg of Tra-IR700 injected intravenously, PDT was performed at 50 J/cm$^2$.

Twenty-four hours after administration of Tra-IR700, in mice receiving PIT a 1 cm-diameter area encompassing the right dorsum including the tumor was irradiated (dose level 50 J cm$^{-2}$). The left dorsum of the tumor was covered with black tape to prevent its exposure to light. Effects in response to PIT were monitored daily and tumor volumes were measured with a caliper twice a week until it reached 500-1000 mm$^3$, at which time mice were euthanized with carbon dioxide gas. In order to determine tumor volume, the greatest longitudinal diameter (length) and the greatest transverse diameter (width) were determined with external caliper.

Tumor volume based on caliper measurements were calculated by the following formula; tumor volume=length×width$^2$×0.5. Data are expressed as means±sem from a minimum of three experiments, unless otherwise indicated. Statistical analyses were carried out using a statistics program (GraphPad Prism; GraphPad Software, La Jolla, Calif.). For multiple comparisons, a one-way analysis of variance (ANOVA) with post test (Kruskal-Wallis test with post-test) was used. The cumulative probability of survival, determining herein as the tumor volume failed to reach 500 mm$^3$, were estimated in each group with the use of the Kaplan-Meier survival curve analysis, and the results were compared with use of the log-rank test with Bonferroni's correction for multiplicity. $P<0.05$ was considered to indicate a statistically significant difference.

Figure 4:
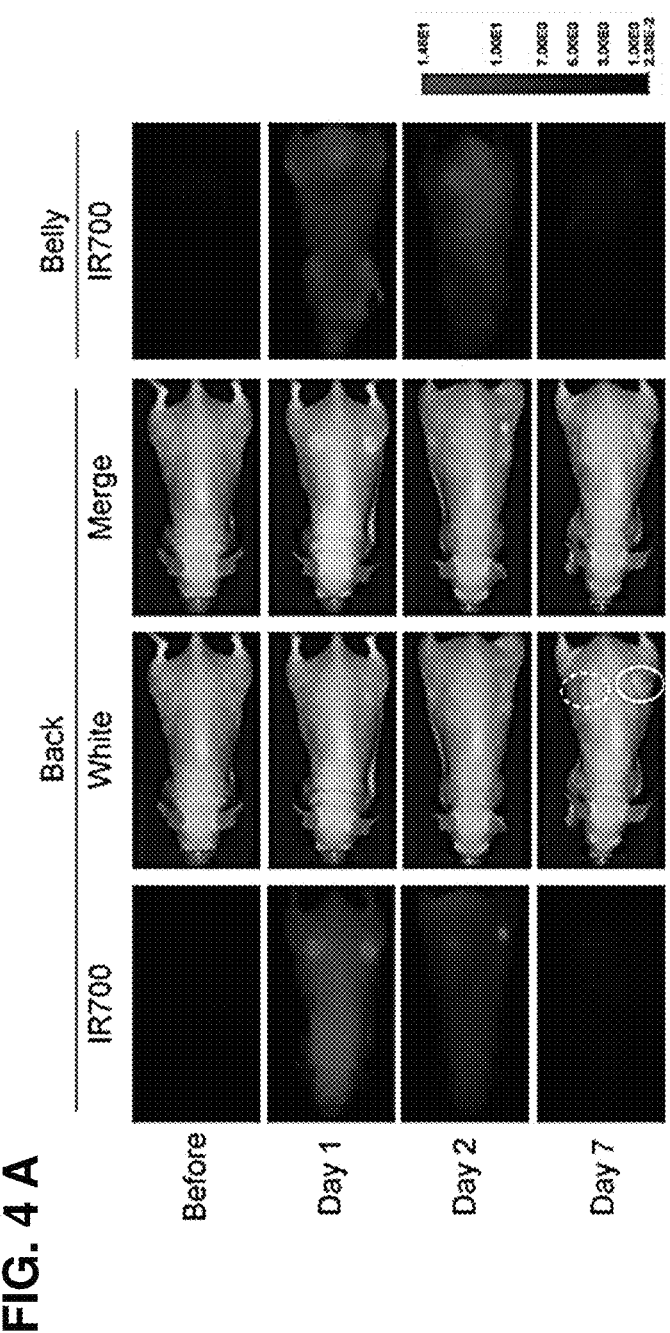
FIG. 4A is a digital image showing the biodistribution of Tra-1R700. 3T3/HER2 tumors (both sides of dorsum) were visualized with IR700 fluorescence as early as 1 day after Tra-1R700 injection (300 μg). Right side of the tumor was irradiated with near infrared (NIR) light on day 1, while left side of the tumor was covered with black tape. Tumor shrinkage was confirmed on day 7. Dashed line: irradiated tumor, solid line: non-irradiated tumor. No other specific localization of IR700 was found except for the bladder accumulation on day 1 due to the excretion of unbound dye (n=5 mice).
FIG. 4B is a graph showing mean tumor volume following administration in vivo of Tra-IR700 or carrier alone followed by PIT (50 J cm$^{-2}$). Data are means±s.e.m. (at least n=12 mice in each group, ***P<0.001," P<0.01 vs. non treatment control, Kruskal-Wallis test with post-test). Tra: trastuzumab.
Figure 4:
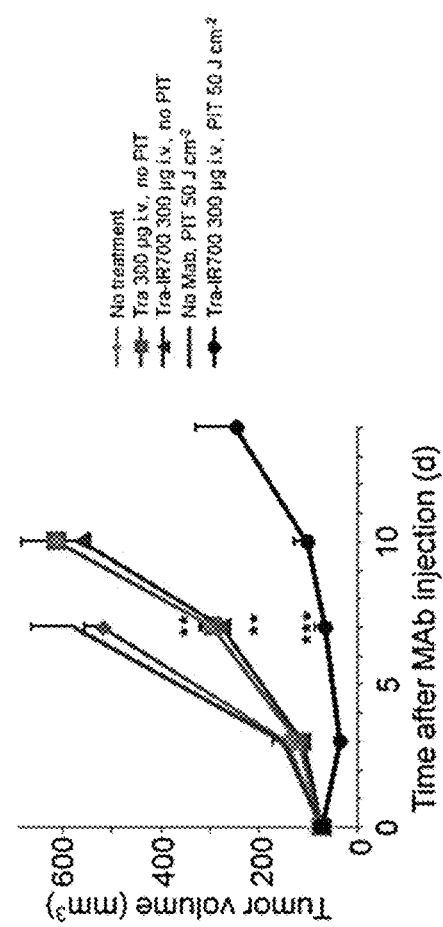

As shown in FIGS. 4A and 4B, whereas 50 J cm$^{-2}$ irradiation resulted in significant tumor growth inhibition in 3T3/HER2+ tumors at day 4, 7, 10 and 14 days after treatment, untreated tumors did not exhibit any detectable effect on tumor growth. In addition, irradiation for Balb/3T3 tumors did not show significant therapeutic effect. Furthermore, no lethal side effects were found during or after the treatment.

Example 8

Synthesis of IRDye 700-Conjugated Vectibix® (Anti-HER1)

Panitumumab (Vectibix®), a fully humanized IgG2 MAb directed against the human EGFR was purchased from Amgen (Thousand Oaks, Calif.) and conjugated to IR700 using the methods described in Example 1. This compound is referred to as Panitumumab-IR700 or Pan-IR700. The number of IR700 per Panitumumab was about 3.

Example 9

Pan-IR700 Selectively Kills HER1+ Cells

This example describes methods used to show that the Pan-IR700 compound described in Example 8 can be used to selectively kill cells that express HER1 (HER1+), but has minimal negative effects on HER1 negative (HER1−) cells.

EGFR-expressing A431 cells were used as the target HER1+ cells. As a control, Balb/3T3 cells which express DsRed fluorescent protein but do not express HER1/EGFR (Balb/3T3/DsRed) were used. Cells were grown in RPMI 1640 supplemented with 10% fetal bovine serum and 1% penicillin/streptomycin in tissue culture flasks in a humidified incubator at 37° C. in an atmosphere of 95% air and 5% carbon dioxide. A431 or Balb/3T3/DsRed cells were seeded on cover glass-bottomed dishes and incubated for 24 hours. Pan-IR700 was added to the culture medium at 10 µg/mL and incubated either for 1 hour on ice or 6 hours at 37° C., then cells were washed with PBS. Culture medium was replaced with phenol red-free medium after washing with phosphate buffered saline (PBS).

Fluorescence microscopy was performed as described in Example 2 to detect the antigen-specific localization of IR700. Pan-IR700 was detected on the cell surface of A431 cells after 1 hour incubation on ice, and was mainly localized to the lysosome 6 hours after incubation at 37° C. No significant IR700 signal was observed with Balb/3T3/DsRed cells.

Figure 5A:
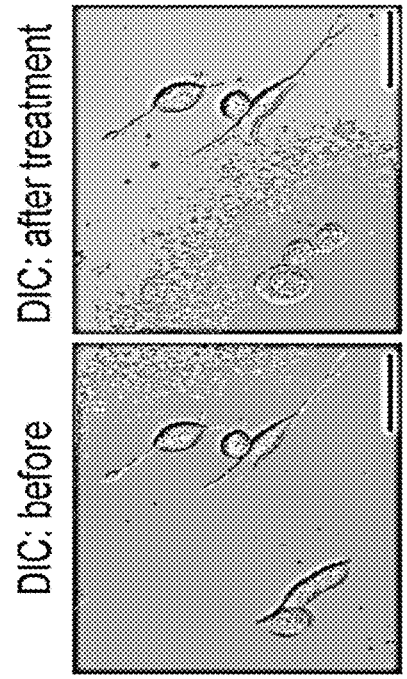
FIG. 5A is a digital image showing a microscopic observation of before and after Pan-1R700 mediated PIT. Scale bar, 50 um.
Figure 5B:
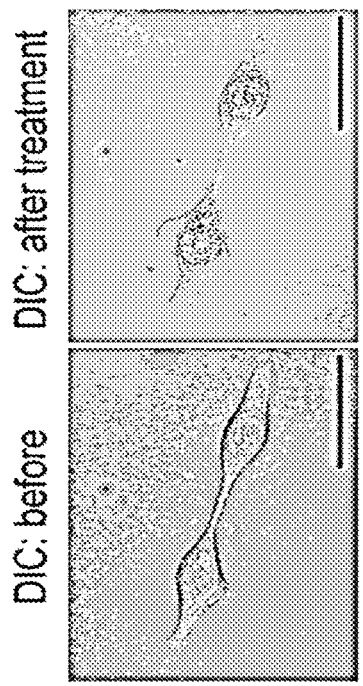
FIG. 5B is a graph showing irradiation dose dependent and target specific cell death in response to Pan-1R700 (PanIR) mediated PIT. Data are means±s.e.m. (n=at least 4, ***P<0.001 vs. non treatment control, Student's t test).

PIT was performed as described in Examples 2 and 3. As shown in FIG. 5A, irradiation of A431 cells at 0.5 to 2 J cm$^{-2}$ resulted in rapid cell death in a dose-dependent manner, representing budding and swelling of the cell membrane. As shown in FIG. 5B, the percentage of cell death in target cells versus untreated control cells was significantly influenced by excitation light dose. In addition, there was no significant cytotoxicity associated with exposure to Pan-1R700 without excitation light or with light exposure without Tra-1R700. However, panitumumab itself had a noticeable treatment effect against A431 cells due to down regulation and signal inhibition of HER1 (Yang et al., *Cancer Res* 59:1236-43, 1999).

Figure 5C:
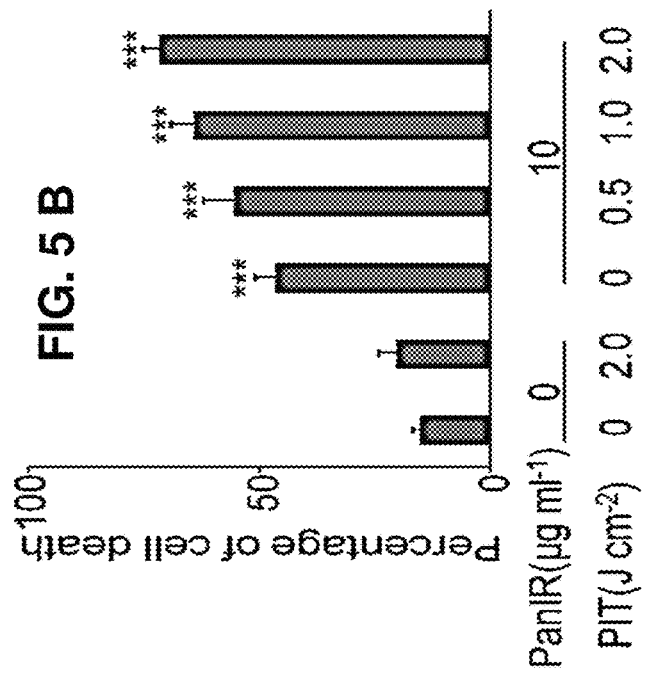
FIG. 5C is a digital image showing EGFR expressing cell specific necrotic cell death was induced by Pan-1R700 mediated PIT. Scale bar, 50 μm. DIC: differential interference contrast

Target-specific phototoxicity was also confirmed with Pan-1R700 mediated PIT in A431 cells and Balb/3T3/DsRed (HER1 negative) co-cultured cells (FIG. 5C). In summary, Tra-1R700 and Pan-1R700 showed identical therapeutic effects to HER2 positive (3T3/HER2) and HER1 positive (A431) cells, respectively, except that unconjugated panitumumab showed noticeable growth inhibition but unconjugated trastuzumab did not reduce growth with the dose used.

Example 10

Pan-IR700 Selectively Kills HER1+ Cells In Vivo

This example describes methods used to show that Pan-IR700 can treat HER1+ tumors in vivo. One skilled in the art will appreciate that similar methods can be used with other tumor/antibody-IR700 combinations.

Six- to eight-week-old female homozygote athymic nude mice (Charles River, NCI-Frederick, Frederick, Md.) were anesthetized with isoflurane. One million A431 cells were injected subcutaneously in the left dorsum of the mice. Four days after cell injection, either 50 or 300 µg of Pan-IR700 was administered intravenously.

To confirm antigen specific localization of Pan-IR700, $1\times10^6$ of 3T3/HER2 cells (HER1 negative) were injected subcutaneously in the right dorsum at the same time of A431 cells injection. Fluorescence images were obtained at indicated time point with Pearl Imager (LI-COR Biosciences) using 700 nm fluorescence channel. Regions of interest (ROI) for both tumor and background were placed for equivalent sized areas containing the same number of pixels. Tumor to background ratio (TBR) was calculated using the following formula: TBR=((mean tumor intensity)−(mean background intensity))/((mean non-tumor intensity)−(mean background intensity)).

Figure 6:
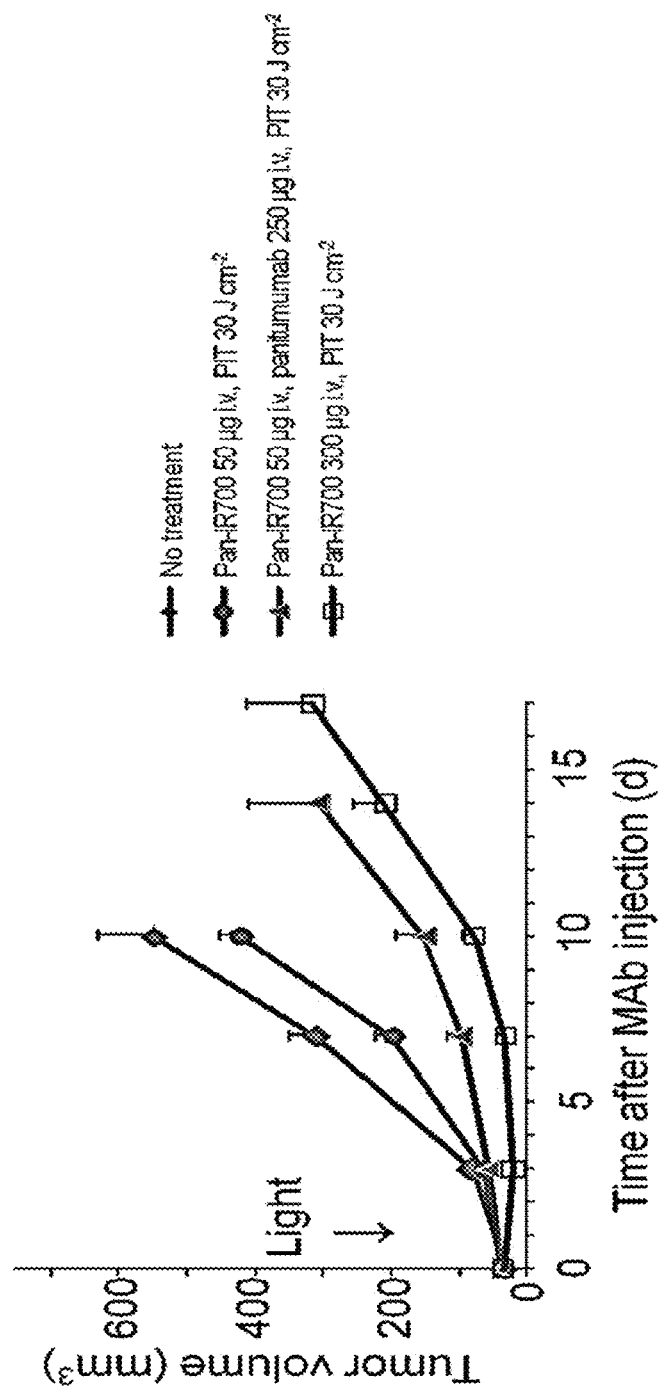
FIG. 6A is a digital image showing specific localization of panitumumab-IR700 conjugate (Pan-IR700) in a mouse previously administered A431 cells. HER1 positive A431 tumor (left dorsum) was selectively visualized as early as 1 d after Pan-IR700 injection (50 μg). HER1 negative 3T3/HER2 tumor (right dorsum) did not show detectable fluorescence (n=5 mice).
FIG. 6B is a graph showing the IR700 signal intensity in A431 tumors over time following injection of two different doses (50 μg and 300 μg) of Pan-IR700. Data are means±s.e.m. (n=4 each mice).
FIG. 6C is a graph showing the tumor to background ratio of IR700 fluorescence intensity in A431 tumors over time following injection of two different doses (50 μg and 300 μg) of Pan-IR700. Data are means±s.e.m. (n=4 each mice).
FIG. 6D is a digital image showing the biodistribution of Pan-1R700. A431 tumors (both sides of dorsum) were selectively visualized with IR700 fluorescence as early as 1 day after Pan-1R700 injection (300 μg). Right side of the tumor was irradiated with near infrared (NIR) light on day 1, while left side of the tumor was covered with black tape. Tumor shrinkage was confirmed on day 7. Dashed line: irradiated tumor, solid line: non-irradiated tumor.
FIG. 6E is a graph showing mean tumor volume following administration in vivo of Pan-IR700 or carrier alone followed by PIT (30 J cm$^{-2}$). PIT was performed on day 1 after Pan-IR700 injection (day 5 after tumor inoculation). Data are means±s.e.m. (at least n=12 mice in each group, ***P<0.001 vs. other control groups, Kruskal-Wallis test with post-test).
FIG. 6F is a graph showing survival time following administration in vivo of Pan-IR700 or carrier alone followed by PIT (30 J cm$^{-2}$) (at least n=12 mice in each group, ***P<0.001 vs. other control groups, log-rank test with Bonferroni's correction for multiplicity.
FIG. 6G is a digital image showing hematoxylin and eosin stained histology images (×40 and ×200) 4 days after PIT treated (right) and untreated (left) tumors. n=5 mice; Scale bar, 100 um. Pan: panitumumab.
FIG. 6H is a graph showing that high-dose administration of Pan-1R700 lead to higher antitumor efficacy of Pan-1R700 mediated PIT for A431 tumors in vivo. Tumor growth inhibition by Pan-1R700 mediated PIT was Pan-1R700 dose-dependently observed. Data are means±s.e.m. (at least n=12 mice in each group).

As shown in FIG. 6A, Pan-IR700 localized to the A431 tumor. The fluorescence intensity of Pan-1R700 in a A431 tumor decreased gradually over days, while tumor to background ratios (TBRs) increased (FIGS. 6B and 6C). The fluorescence intensity of the 3T3/HER2 tumor was the same as that of background (non-tumor lesions). When 300 µg of Pan-1R700 was administered intravenously, fluorescence intensity of the A431 tumor was more than 3 times higher than 50 µg injection at 1 day after injection, however, TBR was lower because of high background signal (FIGS. 6B and 6C). As less antitumor activity was found in mice receiving 50 µg (vs. 300 µg) of Pan-1R700 injection following irradiation the higher injection dose was used (FIG. 6H). Biodistribution of Tra-1R700 was determined with IR700 fluorescence because tissue levels of radioactivity and fluorescence might be different due to their different excretion routes and catabolism when using dual-labeled radiolabeled-Pan-1R70015. There was no other specific localization of IR700 except for bladder accumulation on day 1 probably due to excretion of catabolized and unbound dye (FIG. 6d).

As shown in FIG. 6D, PIT treatment following Pan-IR700 administration began to shrink tumors at day 2, in contrast to non-PIT treated tumors which did not shrink.

To determine the effect of Pan-IR700 or carrier alone followed by PIT, the following methods were used. In order to determine tumor volume, the greatest longitudinal diameter (length) and the greatest transverse diameter (width) were determined with external caliper. Tumor volume based on caliper measurements were calculated by the following formula; tumor volume=length×width$^2$×0.5$^2$. Four days after A431 cell injection as described above, tumor volume reaching around 40 mm$^3$ were selected for the study. Animals were randomized into 8 groups of at least 12 animals per group for the following treatments: (1) no treatment; (2) 300 µg of panitumumab injected intravenously, no PIT; (3) 300 µg Pan-IR700 injected intravenously, no PIT; (4) PIT was performed at 30 J/cm$^2$ without Pan-IR700; (5) Free IR700 dye, dose equivalent to 300 µg of Pan-IR700, was injected intravenously, and PIT was performed at 30 J cm$^{-2}$; (6) 50 µg of Pan-IR700 was injected intravenously, PIT was performed at 30 J cm$^{-2}$; (7) 50 µg of Pan-IR700 and 250 µg of panitumumab was injected intravenously, PIT was performed at 30 J cm$^{-2}$; and (8) 300 µg of Pan-IR700 was injected intravenously, PIT was performed at 30 J cm$^{-2}$. After the treatment mice were monitored daily, and tumor volume was measured twice a week until the tumor volume reached 500 mm$^3$, at which time mice were euthanized with carbon dioxide gas. To test a short-term toxicity, 300 µg of Pan-IR700 was repeatedly administered intravenously for non-tumor-bearing mice, twice a week, for 4 weeks.

As shown in FIG. 6E, whereas treatment with Pan-IR700 and 30 J cm$^{-2}$ irradiation resulted in significant tumor growth inhibition in A431 (HER1+) tumors at day 3, 7, 10, 14 and 17 days after treatment, untreated tumors did not exhibit any detectable effect on tumor growth. In addition, as shown in FIG. 6F, treatment with Pan-IR700 and 30 J cm$^{-2}$ irradiation resulted in significant increases in survival time of mice with A431 (HER1+) tumors. Furthermore, no lethal side effects were found during or after the treatment. FIG. 6G shows microscopic images of cells four days following treatment with Pan-IR700 followed by no PIT therapy or PIT therapy. Pathological analysis revealed that only scant viable A431 tumor cells were present after Pan-IR700 mediated PIT and massive granulation with inflammatory change was observed in the tumor nodule. It was also observed that tissue edema developed superficially. To assess the acute phase toxicity of Pan-1R700, we repeatedly administered 300 µg of Pan-1R700 intravenously twice a week for 4 weeks, but there were no adverse effects observed up to 8 w (n=4) compared with the control group.

Example 11

HuJ591-IR700 Selectively Kills PSMA+ Cells In Vivo

This example describes methods used to show that HuJ591-IR700 can treat prostate-specific membrane antigen (PSMA)+ tumors (such as those found in prostate cancer) in vivo. One skilled in the art will appreciate that similar methods can be used with other tumor/antibody-IR700 combinations.

J591, a fully humanized IgG2 MAb directed against human PSMA was obtained from Prof. Neil Bander, Cornell Univ and conjugated to IR700 using the methods described in Example 1. This compound is referred to as J591-IR700. The number of IR700 per J591 was about 2.

Six- to eight-week-old female homozygote athymic nude mice (Charles River, NCI-Frederick, Frederick, Md.) were anesthetized with isoflurane. On day 0 Two million PC3-PIP cells (PSMA+) were injected subcutaneously in the bottom dorsum of the mice and PC3-FLU cells (PSMA−) were injected subcutaneously in the top dorsum of the mice. On day 3, 100 µg of PSMA-IR700 was administered ip.

To confirm antigen specific localization of J591-IR700, 2×10$^6$ of PC3-FLU cells (PSMA−) were injected subcutaneously in a different area at the same time of PC3-PIP cell injection. Fluorescence images were obtained at indicated time point with Pearl Imager (LI-COR Biosciences) using 700 nm fluorescence channel, as described in Examples 7 and 10.

As shown in FIG. 7, J591-IR700 localized to the PC3-PIP tumor. Nonspecific blood pool and enhanced permeability and retention effects (EPR effect) dimly show PC3-FLU (PSMA−) tumor.

To determine the effect of HuJ591-IR700 in the presence or absence of PIT, the right side of the mouse was irradiated and the left side was not, as described in Examples 7 and 10. Specifically, on day 4, mice received PIT 50 J/cm$^2$ for right tumors, on day 5 PIT 100 J/cm$^2$ for right tumors (and an image obtained), on day 11, J591-IR700 was administered (100 µg ip) and an image obtained, on day 12 PIT 50 J/cm$^2$ for right tumors, on day 13 PIT 100 J/cm$^2$ for right tumors and on day 19 J591-IR700 was administered (100 µg ip). On Day 20, an image was obtained and the tumor excised and imaged. As shown in FIG. 7, PIT treatment following J591-IR700 administration began to shrink tumors at day 5, in contrast to non-PIT treated tumors which did not shrink.

Example 12

Selective Killing In Vitro by Antibody-IR700 Molecules

This example describes additional results showing that the disclosed antibody-IR700 compounds selectively kill cells that express the appropriate protein. The photoimmunotherapy (PIT) methods are described in Example 2.

As shown in FIG. 8, Tra-1R700 specifically killed HER2 expressing 3T3/1-IER2, SHAW, SKOV3 and MDA-MB-453 cells, Pan-1R700 specifically killed HER1 expressing A431 and MDA-MB-468 cells, and huJ591-1R700 specifically killed prostate specific membrane antigen (PSMA) expressing LNCaP cells.

Example 13

Trastuzumab-IR700 Treatment of Metastases

This example describes methods used to show that Tra-IR700 can treat lung metastases.

HER2 expressing 3T3/HER2 cells (0.5 to 2 million cells) were injected intravenously into tail vein of female nude mice. Trastuzumab-IR700 (100 µg) was injected intravenously 5 days after the tumor cell injection. As multiple tiny lung metastases were confirmed with Tra-IR700 localization in ex vivo imaging, the lungs were treated with 30 J/cm2 of NIR light from outside the body 2 days after Trastuzumab-IR700 injection. It was observed that the lung metastases cleared, and there was an observed increase in the overall survival time of the mice as compared to mice that did not receive Tra-IR700.

Example 14

Real-Time Monitoring of In Vivo Acute Necrotic Cancer Cell Death

This example describes methods used to monitor in vivo acute necrotic cancer cell death induced by near infrared photoimmunotherapy in real-time using fluorescence lifetime imaging. Although a specific example of Pan-IR700 is described, one will appreciate that other antibody-IR-700 molecules can be used for other tumors.

As described herein, monoclonal antibody-based, highly specific phototherapy (photoimmunotherapy; PIT) that utilizes a near infrared (NIR) phthalocyanine dye, IRDye700DX (IR700) conjugated with mAbs. NIR light exposure leads to immediate, target-selective necrotic cell death in vitro. Detecting immediate in vivo cell death is more difficult because it takes at least three days for the tumor to begin to shrink in size. In this example, fluorescence lifetime (FLT) was evaluated before and after PIT for monitoring the immediate cytotoxic effects of NIR mediated mAb-1R700 PIT. Anti-EGFR panitumumab-IR700 was used for targeting EGFR-expressing A431 tumor cells. PIT with various doses of NIR light was performed in cell pellets in vitro and in subcutaneously xenografted tumors in mice in vivo. FLT measurements were obtained before and 0, 6, 24 and 48 h after PIT. in vitro, PIT at higher doses of NIR light immediately led to greater FLT shortening in A431 cells. in vivo, PIT induced immediate shortening of FLT in treated tumors after a threshold NIR dose of 30 $J/cm^2$ or greater. In contrast, lower levels of NIR light (10 $J/cm^2$ or smaller) did not induce shortening of FLT. Based on these observations, FLT imaging can be used to monitor the early and massive cytotoxic effects of mAb-1R700-induced PIT even before morphological changes can be seen in the targeted tumors.

Materials and Methods

Reagents.

Panitumumab, a fully humanized IgG2 monoclonal antibody (MAb) directed against the human EGFR, or HER1, was purchased from AMGEN Inc. A water soluble, silicon-phthalocyanine derivative, IRDye 700DX NHS ester (IR700; $C_{74}H_{96}N_{12}Na_{4}O_{27}S_{6}Si_{3}$, molecular weight of 1954.22) was purchased from LI-COR Bioscience. All other chemicals used were of reagent grade.

Synthesis of 1R700-Conjugated Panitumumab.

Panitumumab (1 mg, 6.8 nmol) was incubated with IR700 (66.8 µg, 34.2 nmol, 5 mmol/L in DMSO) in 0.1 mol/L $Na_2HPO_4$ (pH 8.6) at room temperature for 1 h. Then the mixture was purified with a Sephadex G50 column (PD-10; GE Healthcare). The protein concentrations were determined with Coomassie Plus protein assay kit (Pierce Biotechnology) by measuring light absorption at 595 nm (8453 Value System; Agilent Technologies). The concentration of IR700 was measured by absorption with spectroscopy to confirm the average number of fluorophore molecules conjugated to each Panitumumab molecule. The number of IR700 per antibody was approximately 4 for the 1:4.5 reaction conditions. The addition of 0.4% SDS to the sample dissociated the fluorophores from each other, effectively causing dequenching. Quenching efficiency (QE) for a particular conjugation is defined as the fluorescence intensity with SDS divided by fluorescence intensity without SDS. Panitumumab-1R700 conjugate (Pan-1R700) demonstrated a QE of about 4.0 at pH 7.2. Pan-1R700 was kept at 4° C. in the refrigerator as a stock solution.

Fluorescence Lifetime Measurements.

FLT experiments were performed with the eXplore Optix™-MX2 system (ART Advanced Research Technologies, Inc.) (Hutchinson et al., *Biophys J* 68:1574-82, 1995; Ma et al., *Appl Opt* 46:1650-7, 2007). A fixed pulsed laser diode was used as an excitation source at a wavelength of 670 nm. Region of interest (ROI) measurements with a spot size of 1.5 mm were selected at the image plane. The laser power was automatically chosen as the highest power that does not saturate the photon detector. Lifetime analysis was performed by using the ART OptiView (ART Advanced Research Technologies, Inc.). Lifetime values and lifetime mapping were calculated to fit fluorescence temporal point-spread functions (TPSFs) as single-exponential models with the Fit TPSF tool.

Photoimmunotherapy for In Vitro and In Vivo Models.

PIT was performed with a red light-emitting diode (LED) light at 680 to 700 nm wavelength (Tech-LED, Marubeni America Co.) (Mitsunaga et al., *Bioconjug Chem.* 23:604-9, 2012). Power densities were measured with an optical power meter (PM 100, Thorlabs).

Determination of FLT for Pan-IR700.

Samples of Pan-IR700 at concentrations of 2.5, 5, 20, 40 pg/mL were prepared by dilution with PBS. The fluorescence intensities and lifetimes of each sample were determined using the Optix MX2 system at room temperature within a 1.7 ml centrifuge tube. To investigate the effect of PIT using Pan-1R700, the FLT of each sample at the concentration of 50 pg/mL was measured after irradiating the samples at a PIT dose of 0, 2, 4, 8, 15, 30 J/cm2.

Cell Line.

The HER1 positive cell line, A431 was used for HER1 targeting studies with panitumumab conjugates. The cell line was grown in RPMI 1640 (Life Technologies) containing 10% fetal bovine serum (Life Technologies), 0.03% L-glutamine, 100 units/mL penicillin, and 100 pg/mL streptomycin in 5% CO2 at 37° C.

Cell Pellet FLT Studies A431.

Cells were plated on 75 $mm^2$ cell culture flasks and incubated until confluent. Then Pan-IR700 conjugate was added to the media (1 pg/mL), and cells were incubated for 24 h at 37° C. Upon completion of incubation, cells were removed from the flasks, and centrifuged to obtain pellets. The resulting cell pellets were washed with PBS×3 and placed in 1.7 mL centrifuge tubes. The fluorescence intensities and lifetimes of each sample were then obtained. To investigate the effect of cellular internalization with Pan-IR700 conjugates, A431 cells were plated on a 75 $mm^2$ flask and were incubated with Pan-1R700 for 1, 2, 4, 6, 15 and 24 hours. After removing the flasks and obtaining A431 cell pellets, FLT measurements of the A431 pellet was acquired.

After the A431 cell pellets were incubated overnight with Pan-R700, cell pellets were irradiated at doses of 0, 2, 4, 8, 15, 30 J/cm2. After that, these pellets were gently washed with PBS×1 and fluorescence intensity and lifetime images were obtained. To detect the antigen specific localization of IR700 and to confirm the morphological changes of A431 cells before and after PIT, fluorescence microscopy was performed using Olympus BX61 microscope (Olympus America) equipped with the following filters: a 590-650 nm excitation filter, a 665-740 nm band pass emission filter. Transmitted light differential interference contrast images (DIC) were also acquired. A431 cells were plated on a cover glass-bottomed culture well and incubated for 24 hours. Pan-IR700 was added to the medium (10 pg/mL), and the cells were incubated for either 6 or 24 hours. Once complete, the cells were washed once with PBS, and fluorescence microscopy was performed before and after PIT.

Mouse Model.

A431 cells (HER1+, HER2−, 1×106 cells) were injected subcutaneously on both sides of the dorsum of female nude mice (National Cancer Institute Animal Production Facility). The experiments were performed at 6-9 days after cell injection.

In Vivo FLT Imagine Studies after PIT.

Tumor-bearing mice were divided into 3 groups of 5 mice per group for the following irradiation doses of PIT: 10, 30, and 50 J/cm$^2$. As a control, 5 mice were prepared without PIT. One hundred μg of Pan-IR700 were injected intravenously via the tail vein into every mouse 24 hours before PIT. A431 tumors in the right side of the dorsum were treated with PIT while the contralateral control tumors were shielded from light exposure with aluminum foil. After PIT, FLT images were obtained at the following time points: 0, 6, 24 and 48 hours. Zero hours acquisitions were performed immediately after PIT. Maximum spot values of each ROI in the FLT images were calculated for tumors on both sides of the dorsum.

Histological Analysis.

To evaluate serial histological changes immediately (within 5 min) after PIT with various NIR light doses, microscopy was performed (BX51, Olympus America). A431 tumors were harvested in 10% formalin immediately after 0, 10, 30, and 50 J/cm$^2$ of NIR light exposure. Serial 10-μm slice sections were fixed on a glass slide with H-E staining.

Statistical Analysis.

Statistical analyses were carried out using a statistics program (GraphPad Prism; GraphPad Software). Mann-Whitney's U test was used to compare the lifetime value between those of treated tumors and untreated tumors. Student's t test was used to compare with the lifetimes of treated tumors to no treatment control. $P < 0.05$ was considered to indicate a statistically significant difference.

Results

FLT is Independent from the Pan-IR700 Concentration in the Solution.

Figure 10:
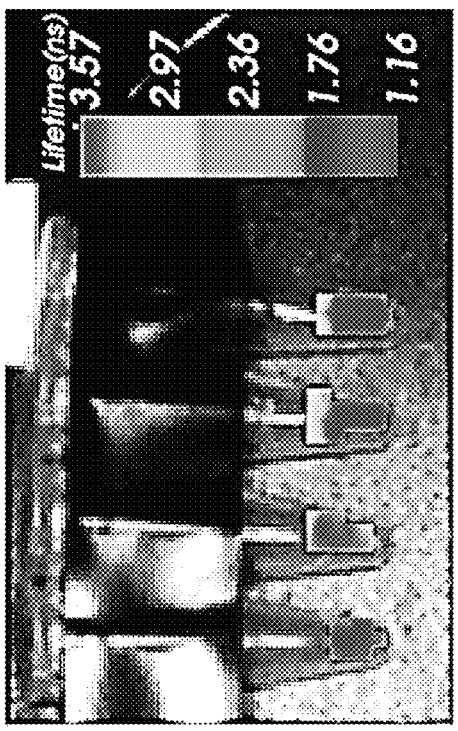
Figure 10:
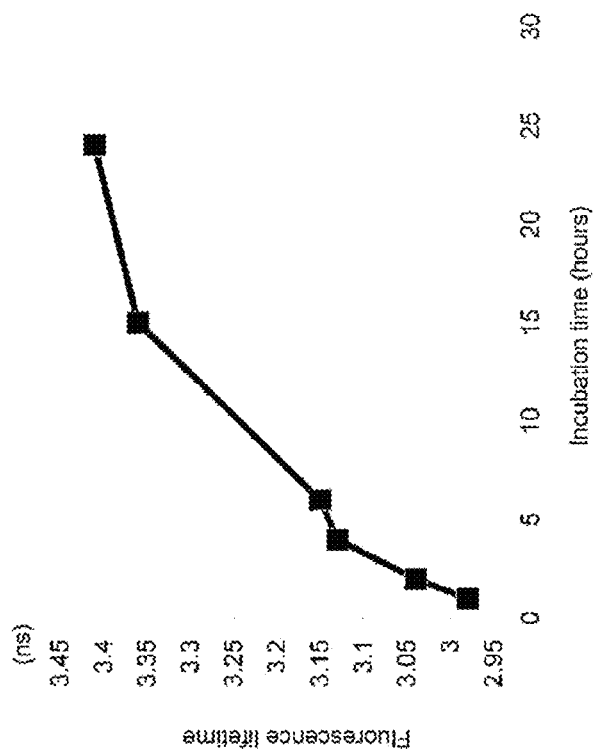
Figure 10:
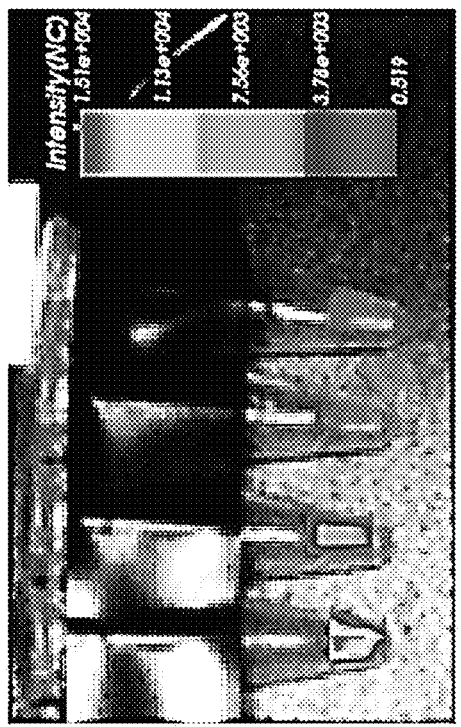
Figure 10:
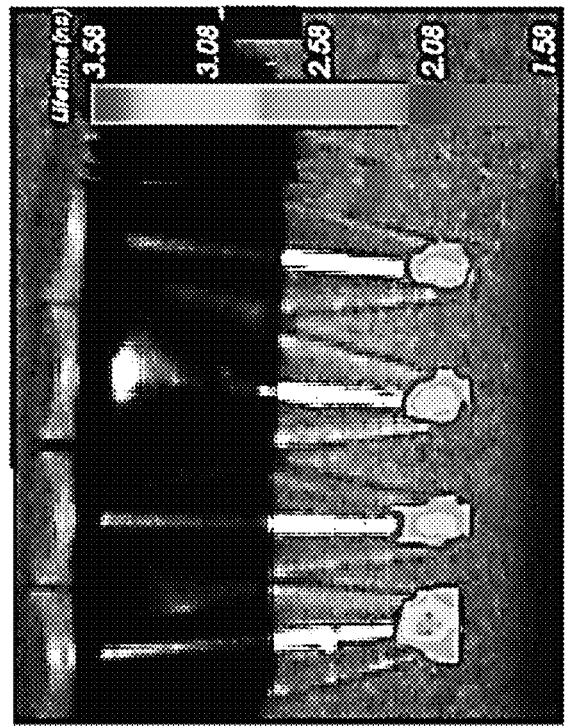

The FLTs of various concentrations of Pan-IR700 were approximately the same, 3.56+/−0.081 ns; 3.62 (2.5 pg/mL), 3.58 (5 pg/mL), 3.44 (20 pg/mL), 3.60 ns (40 pg/mL), whereas the fluorescence intensities were decreased in proportion to the concentration (FIGS. 10A and 10B).

NIR Light Exposure Alone does not Affect the FLT of Pan-IR700.

Pan-IR700 (50 pg/mL) by itself was irradiated and FLT was measured. Both fluorescence intensity and lifetime did not change by irradiation of LED at the dose of 0, 2, 4, 8, 15, 30 J/cm2. The FLT was approximately 3.44+/−0.058 ns.

Internalization of Pan-IR700 Prolonged the IR700 FLT.

FLT of A431 cells increased with the duration of the incubation with Pan-1R700. The FLTs of A431 cell pellet at 1, 2, 4, 6 15 and 24 hours of incubation were 2.98, 3.05, 3.13, 3.15, 3.36 and 3.4 ns, respectively. After 15 hours incubation, FLT of IR700 reached its peak and showed no further prolongation (FIG. 10D).

Greater Exposure of NIR Light Shortened the FLT of IR700 Containing A431 Cells.

PIT with greater NIR light doses induced greater shortening of FLT in A431 cell pellets incubated with Pan-IR700 for 24 hours before exposure to the NIR light (FIG. 10C). PIT shortened the FLT of A431 pellets down to 3.28, 3.09, 2.94 and 2.85 ns at doses of 0, 8, 15 and 30 J/cm2, respectively.

PIT Induced Typical Necrotic Cell Death in A431 Cells as Well as Rupture of Lysosomes.

Under microscopy, Pan-1R700 was seen on the cell membrane and within endolysosomes at 24 hours after incubation. Following exposure to NIR light, immediate damage was induced in the cell membranes and lysosomes. Multifocal bleb formation was seen in the cellular membranes, characteristic of necrotic cell death induced by PIT (FIG. 11).

Effective PIT Induced Immediate Shortening of the FLT of IR700 In Vivo.

The average FLT of A431 tumors 1 day after administration of 100 pg of Pan-IR700 in vivo was 3.27+/−0.46 ns (n=40). Significant shortening of FLT was induced immediately after PIT with NIR light doses of 30 and 50 J/cm$^2$ to experimental tumors (right dorsum, 30 J/cm$^2$; down to 61.5%+/−5.05% of untreated tumors in the same mouse; $p<0.01$, 50 J/cm$^2$; down to 69.0%+110.92% of untreated tumors in the same mouse; $p<0.05$).

Figure 12A:
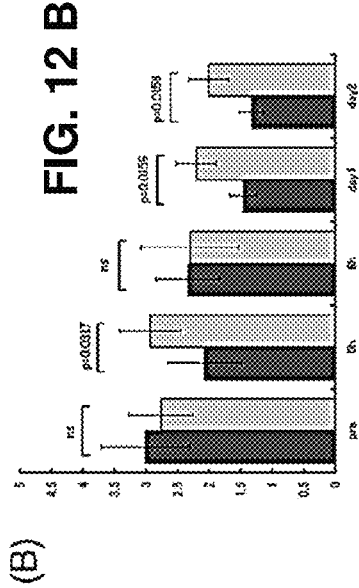

Transient prolongation of IR700 FLT was found in and around PIT treated tumors 6 hours after PIT at NIR light doses of 30 and 50 J/cm2 but continued to shorten at >24 hours after PIT. PIT with 10 J/cm$^2$ did not show this transiently prolonged FLT. IR700 FLT in untreated control tumors also slightly shortened at late time points (FIG. 12A).

Figure 12B:
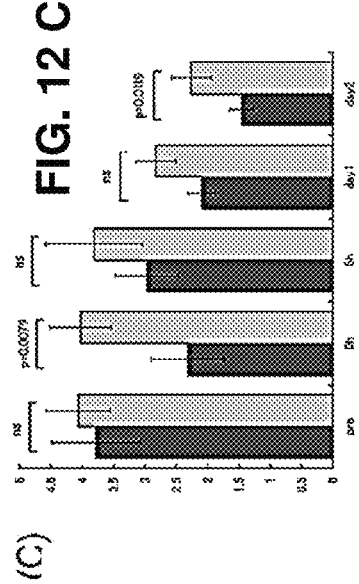
Figure 12C:
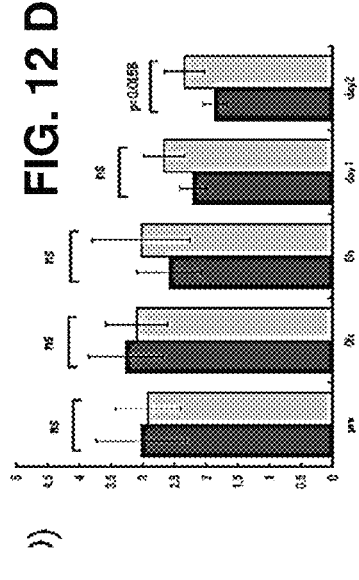
Figure 12D:
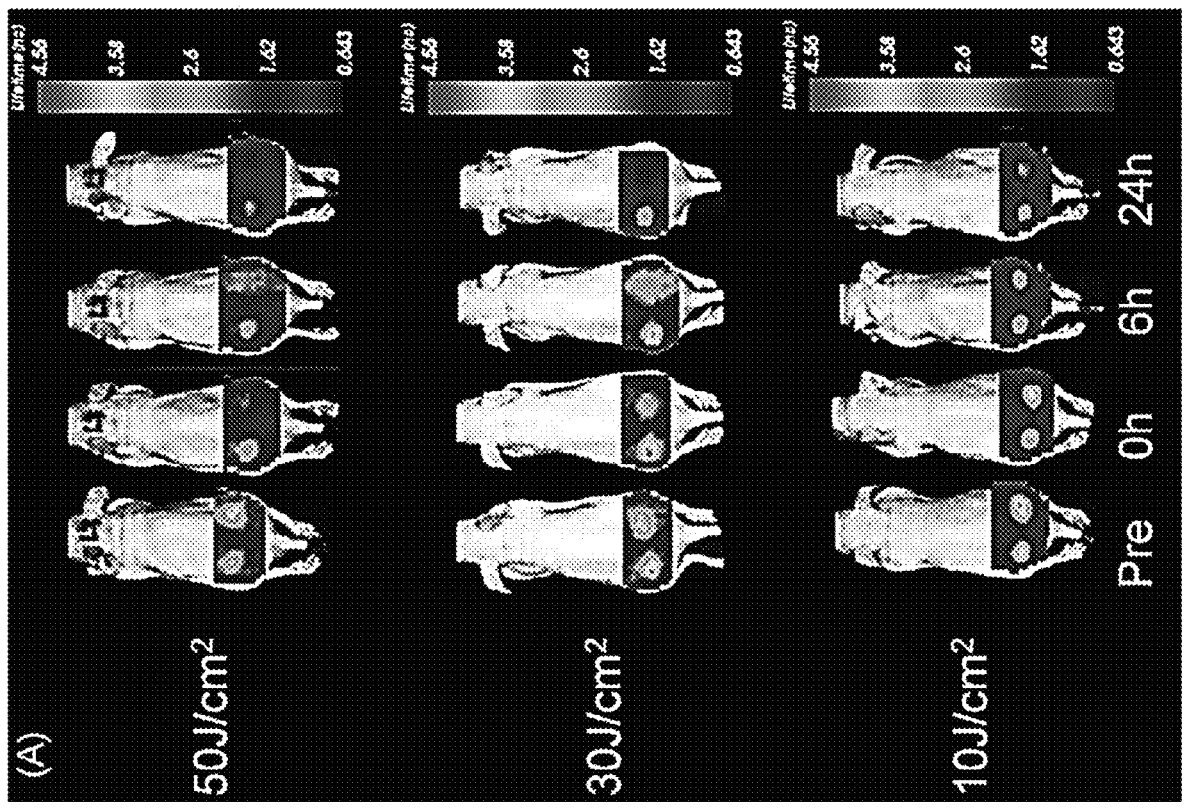

Comparison with IR700 FLT between exposed and non-exposed tumors with NIR light of 30 and 50 J/cm$^2$ in the same mice showed significant differences at 0, 24 and 48 hours after PIT ($p<0.05$; FIGS. 12B and 12C). The differences of IR700 FLT at 6 hours post-PIT were not statistically significant due to the diffuse temporal increase around exposed tumors. IR700 FLTs of exposed and non-exposed tumors with NIR light of 10 J/cm$^2$ did not show significant difference at any time point (FIG. 12D).

FLT in PIT treated tumors with 50 and 30 J/cm$^2$ shortened significantly ($p<0.01$) compared with no treatment controls (0 J/cm$^2$). FLTs were immediately shortened to 69.1+/−10.9% and 61.5+/−5.1% by PIT with 50 and 30 J/cm$^2$, respectively. A431 tumors irradiated with only 10 J/cm$^2$ showed no significant shortening of FLT immediately after PIT. FLT shortened by only 7.7% at 48 hours after PIT compared with the untreated control (FIG. 13A). Interestingly, the FLT of non-irradiated tumors in PIT treated mice shortened slightly more than that in the untreated mice, but these changes were not significant, however, FLT became shorter with larger doses of NIR light to the treated tumors (FIG. 13B). These changes may be caused by small amounts of light diffusing through the soft tissues from the "treated" side to the "untreated" side, thus explaining the dose-dependence of the effect.

Histological Analysis.

Microscopy of treated tumors revealed various degrees of necrosis and micro-hemorrhage with clusters of healthy or damaged but potentially viable tumor cells after PIT. Necrotic damage was diffuse and intense and the amount of surviving tumor cells was reduced when 30 or 50 J/cm$^2$ of NIR light was administered. In contrast, when 10 J/cm$^2$ of NIR light was administered, necrotic cell damage was found in only limited areas with relatively large areas of viable cancer cells accounting for the majority of the tissue (FIG. 13C).

Discussion

Fluorescence microscopy studies showed Pan-IR700 gradually internalized into lysosomes in A431 cells at 37° C. (FIG. 11). As Pan-IR700 internalized (FIG. 10D) IR700 FLT became longer as a function of incubation time. IR700 eventually accumulated in the lysosome. After exposure to a threshold intensity of NIR light, Pan-IR700 induced immediate outer cell membrane damage and damage to lysosomes resulting in accumulation of IR700 within the cytoplasm and into the extracellular space. This damage was associated with a significant reduction in IR700 FLT. This implies that cellular internalization of the Pan-IR700 conjugate by itself prolongs IR700 FLT as it accumulates in the endolysosome. However, by damaging membrane structures, including the lysosomal membrane, PIT induces cell death and releases long FLT IR700, into the cytoplasm whereupon the FLT markedly shortens. Therefore, shortening FLT serves as an indicator of acute membrane damage induced by PIT.

Treatment with PIT with effective therapeutic light dose of NIR leads to shortened IR700 FLT in cancer cells in vitro and in tumors in vivo. The shortening of FLT was dependent on the dose of NIR light exposure in vitro (FIG. 10C). PIT with suboptimal doses of NIR light (10 J/cm$^2$) did not show significant shortening of IR700 FLT in vivo. These differences could be ascribed to the population of cancer cells, which received PIT effects. FIG. 7 demonstrates that PIT with 50 J/cm$^2$ of NIR light exposure or more could eradicate A431 tumors. PIT with 30 J/cm$^2$ was not sufficient to totally eradicate tumors but caused tumor shrinkage and growth delay, indicating while not all cells were killed, most were severely and irreversibly damaged (Mitsunaga et al., Bioconjug. Chem. 23:604-9, 2012).

Shortened FLT of treated tumor in vivo was observed within 30 minutes of a single effective dose of NIR light and indicated a biologic effect several days before tumor size and shape changed. Although size of the lesion is considered a major indicator of cell death, it does not happen fast enough to determine if treatment has been effective. In the specific case of PIT, where light can be reapplied if necessary, a more immediate readout of cell death is needed. Size changes do not occur rapidly enough for monitoring cytotoxic effects. This is especially true of surgical or endoscopic procedures where it is preferable to complete treatments at one setting (Mitsunaga et al., Bioconjug. Chem. 23:604-9, 2012). FLT, because it is an immediate readout of the tumor's condition, can assess the therapeutic effects of PIT to the cancer cells immediately after treatment and aids in deciding whether additional doses of NIR light exposure are necessary or not during the procedure (Kosaka et al., Int J Cancer 129:1671-7, 2011; Longmire et al., Cancer Sci 100:1099-104, 2009).

Interestingly, after an initial shortening of the FLT, it briefly became longer at about 6 hours after PIT. By 24 hours after PIT the FLT was reduced again (FIG. 12). Since prolongation of IR700 FLT as it is being internalized was observed, it is proposed that after cell membrane disruption caused by PIT, the IR700 leaks into the extracellular space where it is internalized by macrophages mobilized to respond to the release of cytokines associated with cell necrosis. This is supported by histologic findings at 6 hr post-PIT that show inflammatory infiltrates composed of macrophages, which are entering the space formerly occupied by viable tumor (Mitsunaga et al., Nat Med 17:1685-91, 2011). This transient prolongation of IR700 FLT may therefore be a sign of effective cell damage followed by initiating tissue repair possibly mediated by the chemokine release or the toll-like receptor system induced by the fragmented DNA and lipid bilayer (Emeagi et al., Cancer Res 72:1342-52, 2012; Shiratsuchi et al., J Immunol 172:2039-47, 2004; Zhu et al., Cell 24:615-29, 2006).

Fluorescent proteins (FPs) are a potential alternative for monitoring tumor growth in vivo (Kimura et al., J Cell Biochem 110:1439-46, 2010; Tsai et al., Anticancer Res 30:3291-4, 2010; Yamamoto et al., Cancer Res 64:4251-6, 2004; Hoffman and Yang, Nat Protoc 1:1429-38, 2006). Fluorescence imaging using FPs is better suited for longitudinal monitoring of the effects of photo-therapy (Jiang et al., Cell Cycle 5:1198-201, 2006; Hoffman and Yang, Nat Protoc 1:775-82, 2006). Acutely, FPs retain their signal regardless of the viability of the cells and even in necrotic cells may be taken up by macrophages. Thus, even though FLT requires post-processing of the fluorescence signal and uses relatively expensive equipment, it is better suited for detecting acute changes than FPs (Hoffman and Yang, Nat Protoc 1:928-35, 2006; Hoffman, Nat Rev Cancer 5:796-806, 2005). Fluorescence imaging with FPs has been used for longitudinal monitoring of the therapeutic effects of PIT (Mitsunaga et al., Bioconjug Chem 23:604-9, 2012). However, PIT-induced acute cell death can only be detected with optical methods such as FLT while longer term changes can be measured with FPs. FLT is clinically translatable while FPs, which require cell transfection, are unlikely to be used clinically.

This data demonstrates that the FLT of Pan-IR700 is a robust measurement that does not depend on the concentration of Pan-IR700 or light exposure in solution. For example, the in vitro Pan-IR700 solution did not change its FLT at varying concentrations or after NIR light exposure with various doses. Therefore, only the surrounding chemical microenvironment seems to affect the IR700 FLT. While IR700 is normally fluorescent and reflects tumor burden, after catabolism in the lysosome and photo-bleaching, fluorescence may be reduced, thus leading to ambiguity regarding tissue viability. However, those photo-chemical and biochemical changes do not affect FLT. Therefore, shortening of FLT is a better biomarker than IR700 fluorescence intensity.

In conclusion, FLT can be used for assessing in near-real-time, the cytotoxic effects of PIT employing a mAb-IR700 conjugate, during surgical or endoscopic procedures. FLT is prolonged during endolysomal internalization but rapidly shortened after cell damage. FLT again is prolonged for a brief period about 6 hours after PIT due to internalization by migrating macrophages. After that there is a steady reduction in FLT. Thus, FLT imaging thus, allows the assessment of the effect of PIT before morphological changes become evident.

Example 15

Combination Photoimmunotherapy and Chemotherapy

This example describes methods used to combine PIT with other therapies for cancer treatment, such as chemotherapy. It is demonstrated that the enhanced permeability generated during PIT enhances delivery of nano-sized agents.

Materials and Methods

Cells.

A431 cells expressing HER1 were used for PIT. Cells were grown in RPMI1640 supplemented with 10% FBS and 1% penicillin-streptomycin in tissue culture flasks in a humidified incubator at 37° C. in an atmosphere of 95% air and 5% carbon dioxide.

Reagents.

IRDye 700DX NHS ester (IR700; $C_{74}H_{96}N_{12}Na_4O_2S_6Si_3$, molecular weight of 1954.22) and IRDye 800CW NHS ester (IR800; $C_{50}H_{54}N_3Na_3O_{17}S_4$, molecular weight of 1166.20) were from LI-COR Bioscience. Panitumumab, a fully humanized IgG2 monoclonal antibody (mAb) directed against the human epidermal growth factor receptor (EGFR; HER1) was from Amgen. Trastuzumab, a recombinant humanized mAb directed against the human EGFR2 (HER2) was from Genentech. Qtracker 800 non-targeted quantum dots was from Invitrogen. All other chemicals used were of reagent grade.

Synthesis of IR700 and IR800-Conjugated mAbs.

Conjugation of dyes with mAbs was performed according to the procedure reported in the examples above. Each mAb (1 mg, 6.8 nmol) was incubated with IR700 (60.2 µg, 30.8 nmol) or IR800 (35.9 µg, 30.8 nmol) in 0.1 mol l$^{-1}$ Na2HPO$_4$ (pH 8.6) at room temperature for 1 h. The mixture was purified with a Sephadex G50 column (PD-10; GE Healthcare). The concentration of dye and protein was measured by absorption with the spectroscopy (8453 Value System; Agilent Technologies) to confirm the number of fluorophore molecules conjugated to each mAb molecule.

In Vivo Nanodrug-Delivery after Photoimmunotherapy.

Six-week-old to 8-week-old female homozygote athymic nude mice were purchased from Charles River (National Cancer Institute Frederick). During treatment, mice were anesthetized with isoflurane. Two million A431 cells were injected subcutaneously in the right and left dorsums of each mouse. Five days after cell injection, 100 µg of Pan-IR700 was administered intravenously, and 1 day later, either side of tumor was irradiated with NIR light from a red-light-emitting diode at wavelengths of 670-690 nm and a power density of 10-100 J cm$^{-2}$, as measured with an optical power meter (PM 100 (Thorlabs)). One hour after PIT, Pan-IR800 (100 µg), Qtracker 800 Non-Targeted Quantum dots (32.5 pmol), or DaunoXome (30 mg kg$^{-1}$) were injected intravenously, and the in vivo fluorescence images were obtained with a Pearl Imager (LI-COR Biosciences) and a Maestro Imager (CRi). For MR imaging, SPIO (Feridex) was administered intravenously 1 h post-PIT and MR images were obtained. The tumors were excised, and frozen or paraffin-embedded for histological study and fluorescence microscopy study after ex vivo imaging.

In Vivo Fluorescence Imaging.

Five days after injection of two million A431 or 3T3-HER2 cells in right and left dorsums, and seven days after MDA-MB-468 cells injection in mammary pads, tumor volumes of approximately 75 mm$^3$ were selected. Signals of IR700 and IR800 was detected with a fluorescence camera (Pearl Imager, LI-COR Biosciences) using the 700 and 800 nm fluorescence channel. Qdot800 was detected with Maestro in vivo Imaging System (CRi) using a band-pass filter, which ranges between 575 to 605 nm (excitation) and a long-pass NIR filter over 800 nm (emission). Fluorescence images of daunorubicin were also obtained with Maestro using a band-pass filter from 503 to 555 nm (excitation) and a long-pass green filter over 580 nm (emission). The tunable emission filter was automatically stepped in 10 nm increments from 650 to 950 nm and from 500 to 800 nm for the NIR and green filter sets at constant exposure. The spectral fluorescence images consist of autofluorescence spectra and the spectra from Qdot800 and daunorubicin, which were then unmixed, based on their spectral patterns using commercial software (Maestro software; CRi). Mice were sacrificed with carbon dioxide immediately after in vivo imaging. The tumors were excised, and frozen or paraffin-embedded for histological study and fluorescence microscopy study after ex vivo imaging.

Therapeutic studies.

To determine the effectiveness of super EPR effect for tumor therapy, whether PIT could enhance the therapeutic effect of DaunoXome was investigated as follows. One million A431 cells were injected subcutaneously in the right dorsum of the mice. To determine the tumor volume, the greatest longitudinal diameter (length) and the greatest transverse diameter (width) were determined with an external caliper. Tumor volume based on caliper measurements was calculated by the following formula; tumor volume=length×width×0.5. Tumors reaching approximately 40 mm$^3$ in volume were selected. Selected mice were randomized into 4 groups of at least 10 mice per group for the following treatments: (1) no treatment; (2) DaunoXome (6 mg kg$^{-1}$); (3) PIT (50 J cm$^{-2}$); (4) PIT (50 J cm$^{-2}$), 1 h later, DaunoXome (6 mg kg$^{-1}$). After treatment, the mice were monitored daily and their tumor volume was measured twice a week until it reached 750 mm$^3$, at which time mice were euthanized with carbon dioxide gas.

Fluorescence Microscopy.

Ten-µm-thick frozen or paraffin sections were prepared and fluorescence in tumor sections was detected using an Olympus BX81 microscope (Olympus America, Inc., Melville, N.Y.) equipped with the following filters: excitation wavelength 590 to 650 nm, and 480 to 550 nm, emission wavelength 662.5 to 747.5 nm, 765 to 855 nm, and 590 nm long pass for IR700, Qdot800, and daunorubicin, respectively. Transmitted light differential interference contrast images were also acquired. H&E staining and Prussian Blue staining were performed according to standard protocol.

Optimal Timing of Second Shot.

To determine the optimal timing of second shot, Pan-IR800 (100 µg) was administered intravenously into A431 bearing mice at 1, 6, and 24 h after PIT treatment, and the dynamic imaging for 1 h was carried out with Pearl Imager according to the protocol described above.

Statistical Analysis.

Data are expressed as means+s.e.m. from a minimum of three experiments, unless otherwise indicated. Statistical analyses were carried out using a statistics program (GraphPad Prism; GraphPad Software). For multiple comparisons, a one-way analysis of variance (ANOVA) with post test (Kruskal-Wallis test with post-test) was used. The cumulative probability of survival, determining herein as the tumor volume was failed to reach 750 mm$^3$, were estimated in each group with the use of the Kaplan-Meier survival curve analysis, and the results were compared with use of the log-rank test with Bonferroni's correction for multiplicity. $P<0.05$ was considered to indicate a statistically significant difference.

Results

Pit Increases the Perfusion in the Tumors

To validate the change of perfusion in the tumors after PIT treatment, dynamic distribution of PEGylated quantum dot 800 (non-targeted Qdot800) was evaluated in A431 (HER1 positive) bearing mice. A431 tumors were treated with a single dose of NIR light (50 J cm$^{-2}$) at 1 d after injection of IR700 conjugated anti-HER 1 mAb (panitumumab) (Pan-IR700). Qdot800 was administered 1 h after light irradiation, and in vivo dynamic imaging studies were carried out. The diameter of Qdot800 was an average of 50 nm, which was determined by size-exclusion HPLC and SDS-PAGE. Rapid accumulation of Qdot800 was observed in the PIT-treated tumors within 1 h, while no significant uptake was detected in the control tumor without exposure to NIR light (FIG. 14A). The increasing rate of signal intensity (SI) between 1 min and 60 min was 25.7-fold higher in the PIT-treated tumor than in control tumor, which was calculated by the following equation as a super EPR index: $[(SI_{PIT\ at\ 60\ min} - SI_{Back\ at\ 60\ min}) - (SI_{PIT\ at\ 1\ min} - SI_{Back\ at\ 1\ min})]/[(SI_{Control\ at\ 60\ min} - SI_{Back\ at\ 60\ min}) - (SI_{Control\ at\ 1\ min} - SI_{Back\ at\ 1\ min})]$ (FIG. 14B). The signals in PIT-treated tumors were highly maintained by 24 h, indicating the long-term retention of Qdot00.

A pathological analyses and fluorescence microscopic studies revealed that PIT resulted in necrotic damages of tumor cells and that Qdot800 was broadly distributed in the necrotic regions and interstitium in the PIT-treated tumors (FIG. 14C). CD31 staining demonstrated that most of blood vessels in the tumors were decrepit and surrounding tumor cells were also severely damaged (FIG. 14C). On the other hand, A431 cells were almost alive in the control tumors and the fluorescence signals of Qdot800 were focal in the vicinity of main blood vessels (FIG. 14C).

Clinical-use magnetic resonance imaging (MRI) contrast agent, super paramagnetic iron oxide (SPIO) (diameter 200 nm), was challenged to determine the breakpoint of permeability. Within 5 min after injection of SPIO, the signal intensity in the PIT-treated tumors was dramatically reduced, while slight decrease in the control tumors were observed (FIG. 15A). The decreasing rate of signal intensities at 60 min was higher in the PIT-treated tumor than in control tumor. SPIO was accumulated in the necrotic regions and interstitium in the PIT-treated tumors, which was confirmed with Prussian Blue staining (FIG. 15B). Similar results were obtained with gadolinium (Gd) labeled polyamidoamine dendrimer (generation 6t) (G6-Gd) and USPIO as T1 and T2 contrast agents, respectively. G6-Gd (diameter 10 nm) was distributed streakly in PIT-treated tumors with time, in contrast, only main vessels on the tumor surfaces were intensely described in the control tumors.

USPIO (diameter 30 nm) was also rapidly taken up by PIT-treated tumors especially in the interstitium and necrotic regions as suggested by Prussian Blue staining. These results demonstrate that nanoparticles with at least 200 nm of diameter exhibit massive and rapid leakage into tumor tissues treated by PIT, and thus this super EPR method can be applied to cancer therapy.

PIT Enhances the Delivery and Efficacy of Anti-Cancer Drugs

The super EPR regimen was tested with second shot of panitumumab (diameter 10 nm) in A431 bearing mice. Panitumumab is a therapeutic monoclonal antibody in clinical use for the treatment of EGRR-expressing, metastatic colorectal carcinoma. The usefulness of panitumumab has also been validated in breast, lung, head, and neck cancers. PIT facilitated the permeability of Pan-IR800 in treated tumors within 10-60 min, while no change on signal intensities were detected in control tumors, consistent with nanoparticles including Qdot800 and G6-Gd (FIG. 16A). The effective light dose needed to achieve sufficient delivery of anti-cancer drugs (Pan-IR800) was determined. Signal intensities of IR800 in PIT-treated tumors increased with time in a light dose-dependent manner (FIG. 16B), and super EPR index of Pan-IR800 in PIT-treated tumors were significantly higher than in control tumors between 1 min and 60 min after probe injection. Slight increase of signal intensity was observed in the control tumor in groups irradiated by high dose of NIR light, probably because scattered NIR light crossed over from the irradiated side (FIG. 16A). A pathological study revealed that necrotic cell death in PIT-treated tumors was more intense when exposed to high dose NIR light. Interestingly, the change of perfusion by PIT was gradually vanished with time after treatment, and was completely stopped within 24 h (FIGS. 16 C and 16D), indicating the repair of the barrier between blood vessels and tumor tissues or the complete blockage of blood flow. These results indicated that optimal timing of second shot is by 6 h. On the basis of the similarity of the change of perfusion in the tumors after PIT induced with two different mAbs (panitumumab and trastzumab) against three different cells (A431 (HER1 positive), 3T3-HER2 (HER2 positive), and MDA-MB-468 (HER1 positive)) expressing various numbers of respective target molecules, thus this super EPR is generally applicable to other mAbs and antigens (FIG. 18).

Figure 17C:
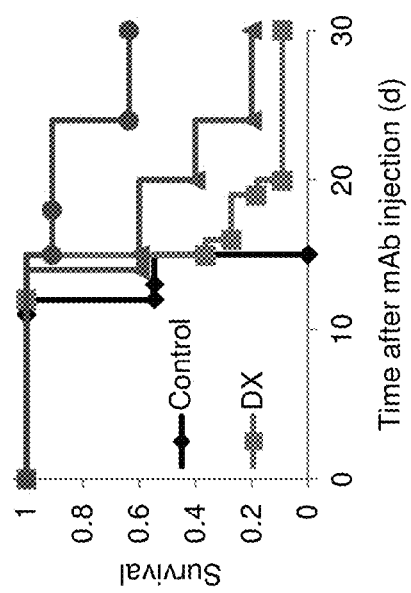
Figure 17B:
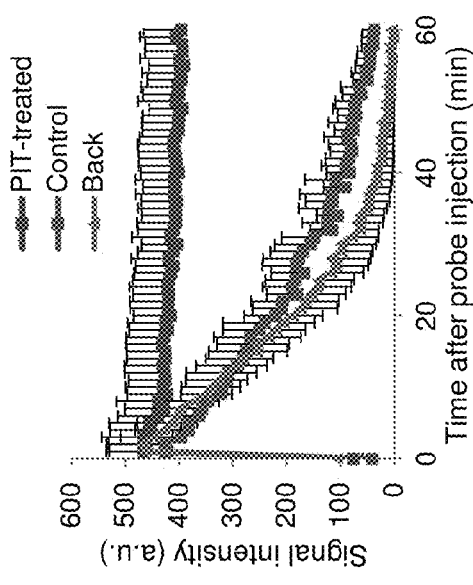
Figure 17A:
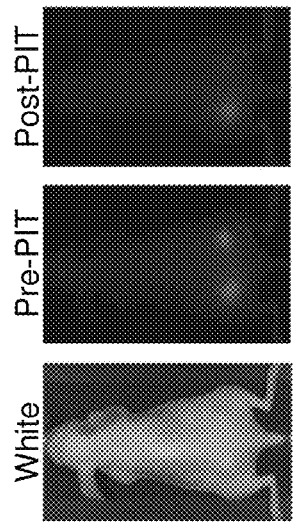
Figure 17F:
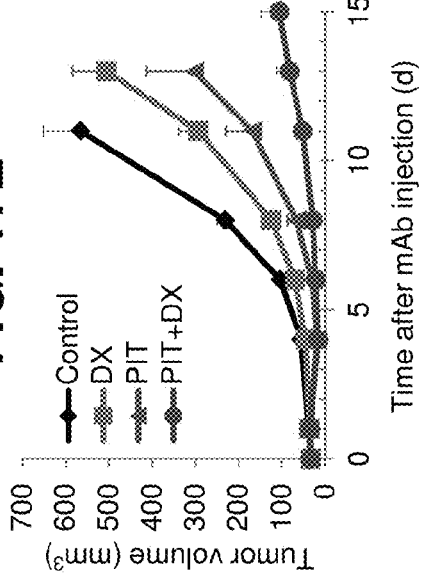
Figure 17E:
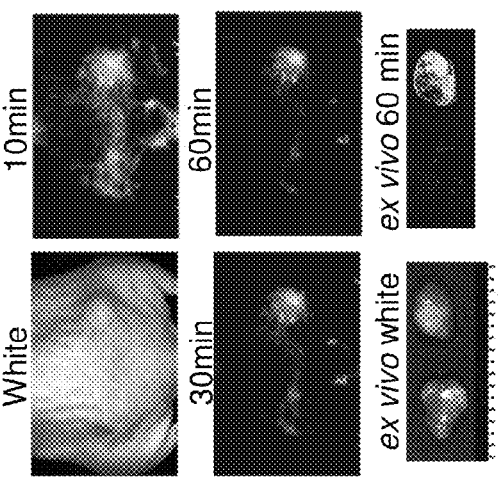
Figure 17D:
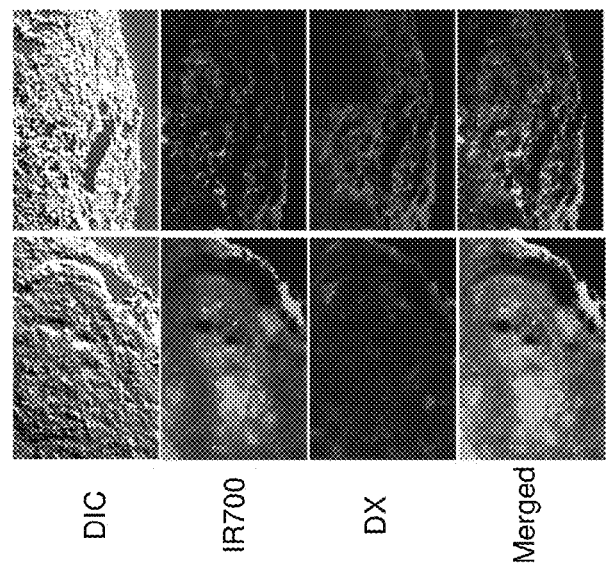

To examine the potential of molecular non-targeted therapeutic agents for efficient cancer therapy based on super EPR effect, liposome containing daunorubicin (DaunoXome; DX) (diameter 50 nm) was scanned and applied therapeutic studies. DX was rapidly accumulated and retained in PIT-treated tumors for 1 h like SPIO and USPIO (FIGS. 17A and 17B). The increasing rate of signal intensities at 60 min was higher in the PIT-treated tumor compared with in control tumor (FIG. 17C). Similar to Qdot800, DX was widely distributed encircling the survived tumor tissues in PIT-treated tumors, and the colocalization of IR700 (indicating survived tumor cells) and DX was partially observed, whereas, the signals of DX in control tumors were localized in the vicinity of main blood vessels (FIG. 17D). This phenomenon was demonstrated both in the margin and core of tumors. A431 tumors were treated with a single dose of light (50 J cm$^{-2}$) at 1 d after injection of Pan-IR700. The efficacy of the methods was determined in four groups of A431 bearing mice (n≥10 in each group). All the tumors we treated had an area of less than 750 mm$^3$, as larger tumors were associated with side effects (subcutaneous bleeding, tumor bleeding, or a weakened state) that, in accordance with our institution's animal care and use guidelines, required that the mice be we euthanized. Tumor volume was significantly reduced in A431 tumors with combination therapy of PIT and DX compared to untreated control mice, mice treated with DX only and PIT only (FIG. 17E), and survival was significantly prolonged in mice with combination therapy of PIT and DX than other groups (FIG. 17F). No obvious loss of body weight was observed in the PIT plus DX group.

In another experiment, 3T3/HER2 mice were injected with Tra-IR700, and 24 h later, NIR light (50 J/cm2) were irradiated to the right side tumor. Tra-IR800 was administered 1 h after PIT treatment. As shown in FIG. 19A, only the right sided tumor was clearly shown up within 10 min. Thus, Tra-IR800 can be accumulated in only the regions where the tumor was exposed to NIR light. In another experiment, MDA-MB-468 bearing mice were injected with Pan-IR700, and 24 h later, NIR light (50 J/cm2) were irradiated to the right side tumor. Pan-IR800 was administered 1 h after PIT treatment. As shown in FIG. 19B, only the right sided tumor was clearly shown up within 10 min.

A431 mice were injected with Pan-IR700, and 24 h later, NIR light (50 J/cm2) were irradiated to the right side tumor. USPIO was administered 1 h after PIT treatment. As shown in FIG. 20A, only the right sided tumor was clearly shown up within 5 min. Prucian blue staining and HE staining is shown in FIG. 20B. The dynamic images of G6-Gd after PIT. A431 mice were injected with Pan-IR700, and 24 h later, NIR light (50 J/cm2) were irradiated to the right side tumor. G6-Gd was administered 1 h after PIT treatment. As shown in FIG. 20C, only the right sided tumor was clearly shown up within 5 min.

Fluorescence microscopic studies in the margin and core regions of tumors was determined. IR700 signal in FIG. 21A shows the A431 cells that survived. Daunorubicin containing liposome was broadly distributed in the PIT-treated tumor tissues and co-localization of IR700 and Daunorubicin containing liposome was partially observed. Especially in the core regions, DX can be taken up in the locally necrotic regions. FIG. 21B shows the change of body weight after therapy. There was no obvious difference between groups.

In conclusion, antibody-IR700 PIT therapy was effective, only when the antibody conjugates were bound to the cell membrane, but showed no phototoxicity when they were not bound or irradiated with NIR light. In addition, PIT induced super enhanced permeability effects (Super-EPR effect) which helped the delivery of nano-sized agents. Thus, PIT using MAb-IR700 combination with nano-sized agents can be used for theranostics for highly selective and effective treatment of cancers.

In view of the many possible embodiments to which the principles of the disclosure may be applied, it should be recognized that illustrated embodiments are only examples of the disclosure and should not be considered a limitation on the scope of the invention. Rather, the scope of the invention is defined by the following claims. We therefore claim as our invention all that comes within the scope and spirit of these claims.

We claim:

1. A phototoxic pharmaceutical composition, comprising:
   a phototoxic conjugate comprising an IR700 molecule conjugated to an antibody that binds to a cell surface protein on a cell, wherein the antibody is pertuzumab or an antigen binding fragment thereof; and
   a pharmaceutically acceptable carrier.

2. The phototoxic pharmaceutical composition of claim 1, wherein the antigen binding fragment is a Fab fragment, a Fab' fragment, a F(ab')$_2$ fragment, a single chain Fv (scFv) or a disulfide stabilized Fv (dsFv).

3. The phototoxic pharmaceutical composition of claim 1, wherein the cell is a tumor cell.

4. A combination, comprising:
   a first pharmaceutical composition comprising a phototoxic conjugate comprising an IR700 molecule conjugated to an antibody that binds to a cell surface protein on a cell, wherein the antibody is pertuzumab or an antigen binding fragment thereof; and
   a second pharmaceutical composition comprising an additional therapeutic agent.

5. The combination of claim 4, wherein the first and/or second composition comprise a pharmaceutically acceptable carrier.

6. The combination of claim 4, wherein the first and second pharmaceutical composition are formulated separately.

7. The combination of claim 4, wherein the additional therapeutic agent is an anti-cancer or anti-neoplastic agent.

8. The combination of claim 4, wherein the additional therapeutic agent is a radiotherapeutic agent, a chemotherapeutic agent, an antibiotic, an alkylating agent, an antioxidant or a kinase inhibitor.

9. The combination of claim 4, wherein the additional therapeutic agent is a microtubule binding agent, a DNA intercalator or cross-linker, a DNA synthesis inhibitor, a DNA or RNA transcription inhibitor, an antibody, an enzyme, an enzyme inhibitor, or a compound that affects gene regulation.

10. The combination of claim 4, wherein the additional therapeutic agent is paclitaxel, docetaxel, vinblastine, vindesine, vinorelbine, an epothilone, colchicine, dolastatin 15, nocodazole, podophyllotoxin, rhizoxin, actinomycin D, daunorubicin, cisplatin, carboplatin, oxaliplatin, mitomycin C, bleomycin, chlorambucil, cyclophosphamide, methotrexate, 5-fluro-5'-deoxyuridine, 5-fluorouracil, camptothecin, etoposide, formestane, trichostatin, raloxifene, 5-azacytidine, 5-aza-2'-deoxycytidine, tamoxifen, 4-hydroxytamoxifen, mifepristone, imatinib, gefitinib, erlotinib, adriamycine, apigenin, rapamycine, zebularine, cimetidine, interleukin-2 (IL-2), or an anti-CTLA4 antibody.

11. The combination of claim 4, wherein the antigen binding fragment is a Fab fragment, a Fab' fragment, a F(ab')$_2$ fragment, a single chain Fv (scFv) or a disulfide stabilized Fv (dsFv).

12. The combination of claim 4, wherein the cell is a tumor cell.

* * * * *